United States Patent
Macko et al.

(10) Patent No.: US 11,337,622 B2
(45) Date of Patent: May 24, 2022

(54) METHOD AND APPARATUS FOR PROVIDING ECONOMICAL, PORTABLE DEFICIT-ADJUSTED ADAPTIVE ASSISTANCE DURING MOVEMENT PHASES OF AN IMPAIRED ANKLE

(71) Applicants: UNIVERSITY OF MARYLAND, BALTIMORE, Baltimore, MD (US); The United States of America as represented by the Department of Veterans Affairs, Washington, DC (US)

(72) Inventors: Richard F. Macko, Ellicott City, MD (US); Anindo Roy, Baltimore, MD (US)

(73) Assignees: UNIVERSITY OF MARYLAND, BALTIMORE, Baltimore, MD (US); The United States of America as represented by the Department of Veterans Affairs, Washington, DC (US)

( * ) Notice: Subject to any disclaimer, the term of this patent is extended or adjusted under 35 U.S.C. 154(b) by 1035 days.

(21) Appl. No.: 15/738,611

(22) PCT Filed: Jun. 20, 2016

(86) PCT No.: PCT/US2016/038370
§ 371 (c)(1),
(2) Date: Dec. 21, 2017

(87) PCT Pub. No.: WO2016/209770
PCT Pub. Date: Dec. 29, 2016

(65) Prior Publication Data
US 2018/0160946 A1    Jun. 14, 2018

Related U.S. Application Data

(60) Provisional application No. 62/182,779, filed on Jun. 22, 2015.

(51) Int. Cl.
*A61H 3/00* (2006.01)
*A61B 5/11* (2006.01)
(Continued)

(52) U.S. Cl.
CPC ............ *A61B 5/1122* (2013.01); *A61B 5/112* (2013.01); *A61B 5/4528* (2013.01);
(Continued)

(58) Field of Classification Search
CPC ...... A61H 3/00; A61H 1/0266; A61B 5/1122; A61B 5/112; A61B 5/4595; A61B 5/4851
See application file for complete search history.

(56) References Cited

U.S. PATENT DOCUMENTS

| 5,716,335 A | 2/1998 | Iglesias et al. |
| 2004/0040180 A1 | 3/2004 | Rennex et al. |

(Continued)

FOREIGN PATENT DOCUMENTS

JP    2007-054086 A    3/2007

OTHER PUBLICATIONS

Extended European Search Report for correspondence EP Application 16815111.6 dated Oct. 22, 2018, pp. 1-11.
(Continued)

*Primary Examiner* — Timothy A Stanis
(74) *Attorney, Agent, or Firm* — Wolter Van Dyke Davis, PLLC; Eugene J. Molinelli; Cian O'Brien

(57) ABSTRACT

A method is described for providing deficit-adjusted adaptive assistance during movement phases of an impaired ankle. The method includes determining, on the processor, a value for a deficit parameter for each movement phase of a compound ankle function based on a difference between a parameter trace for a normal subject and the parameter trace for an impaired subject. The method further includes determining, on the processor, an adaptive magnitude for the
(Continued)

robot-applied torque based on the value for the deficit parameter. The method further includes applying, to the robot joint, the adaptive magnitude for the robot-applied torque in only a first plane for the current movement phase, based on an adaptive timing. An apparatus is also described for providing deficit-adjusted adaptive assistance during movement phases of the impaired ankle.

27 Claims, 44 Drawing Sheets

(51) Int. Cl.
    *A61B 5/00*     (2006.01)
    *A61H 1/02*     (2006.01)
(52) U.S. Cl.
    CPC ......... *A61B 5/4595* (2013.01); *A61H 1/0266* (2013.01); *A61H 3/00* (2013.01); *A61B 5/4851* (2013.01); *A61B 2505/09* (2013.01); *A61H 2201/0157* (2013.01); *A61H 2201/1207* (2013.01); *A61H 2201/1463* (2013.01); *A61H 2201/164* (2013.01); *A61H 2201/165* (2013.01); *A61H 2201/1614* (2013.01); *A61H 2201/1623* (2013.01); *A61H 2201/1676* (2013.01); *A61H 2201/5005* (2013.01); *A61H 2201/5007* (2013.01); *A61H 2201/5012* (2013.01); *A61H 2201/5015* (2013.01); *A61H 2201/5043* (2013.01); *A61H 2201/5058* (2013.01); *A61H 2201/5061* (2013.01); *A61H 2201/5064* (2013.01); *A61H 2201/5069* (2013.01); *A61H 2201/5079* (2013.01); *A61H 2201/5092* (2013.01); *A61H 2201/5097* (2013.01); *A61H 2205/102* (2013.01); *G05B 2219/45108* (2013.01)

(56) References Cited

U.S. PATENT DOCUMENTS

| | | | | |
|---|---|---|---|---|
| 2011/0112447 A1* | 5/2011 | Hsiao-Wecksler | ..... | A61H 3/008 601/33 |
| 2015/0126911 A1 | 5/2015 | Abramowicz et al. | | |
| 2015/0141878 A1 | 5/2015 | Roy et al. | | |
| 2016/0158029 A1* | 6/2016 | Kuiken | ..... | A61F 2/70 623/24 |

OTHER PUBLICATIONS

Roy A, et al, "Measurement of passive ankle stiffness in subjects with chronic hemiparesis using a novel ankle robot", Journal of Neurophysiology, vol. 105, Issue 5, pp. 2132-2149 (2011).
ISA/U.S. International Search Report and Written Opinion, International Patent Application No. PCT/US2016/038370, dated Sep. 13, 2016, pp. 1-13.
Iqbal, K and Roy, A., "Stabilizing PID controllers for a single-link biomechanical model with position, velocity, and force feeback", J. Biomechanical Engineering, vol. 126, pp. 838-843 (2004).
Mathur, K., et al., "Low cost robotics for physical rehabilitative therapy", The A. James Clark School of Engineering, 31 pages (2013).
Roy, A, et al "Anklebot-assisted locomotor training after stroke: A novel deficit-adjusted control approach", IEEE RAS International Conference on Robotics and Automation (ICRA), 8 pages, May 6-10, 2013.
Roy, et al, "Measurement of human ankle stiffness using the Anklebot," ICORR 2007, IEEE 10th International Conference on Rehabilitation Robotics (ICORR), Jun. 2007, pp. 356-363.
Roy, et al, "Robot-aided neurorehabilitation: A novel robot for ankle rehabilitation," IEEE Transactions on Robotics, vol. 25, pp. 569-582, 2009.
Roy, et al, "Facilitating Push-Off Propulsion: A Biomechanical Model of Ankle Robotics Assistance for Plantarflexion Gait Training in Stroke", IEEE RAS & EMBS International Conference on Biorobotics and Biomechatronics (BioRob), 8 pages, Aug. 12-15, 2014.
Roy, et al., "Measurement of Passive Ankle Stiffness in Subjects with Chronic Hemiparesis Using a Novel Ankle Robot." Journal of Neurophysiology 105:2132-2149, 2011.
Extended European Search Report dated Aug. 13, 2021, in corresponding EP20204462.4.
Japanese Office Action issued in corresponding JP2020-129355; dated Jul. 26, 2021. English translation provided.
Japanese Office Action for corresponding JP2017-564398, dated Dec. 6, 2021. English translation provided herewith.

\* cited by examiner

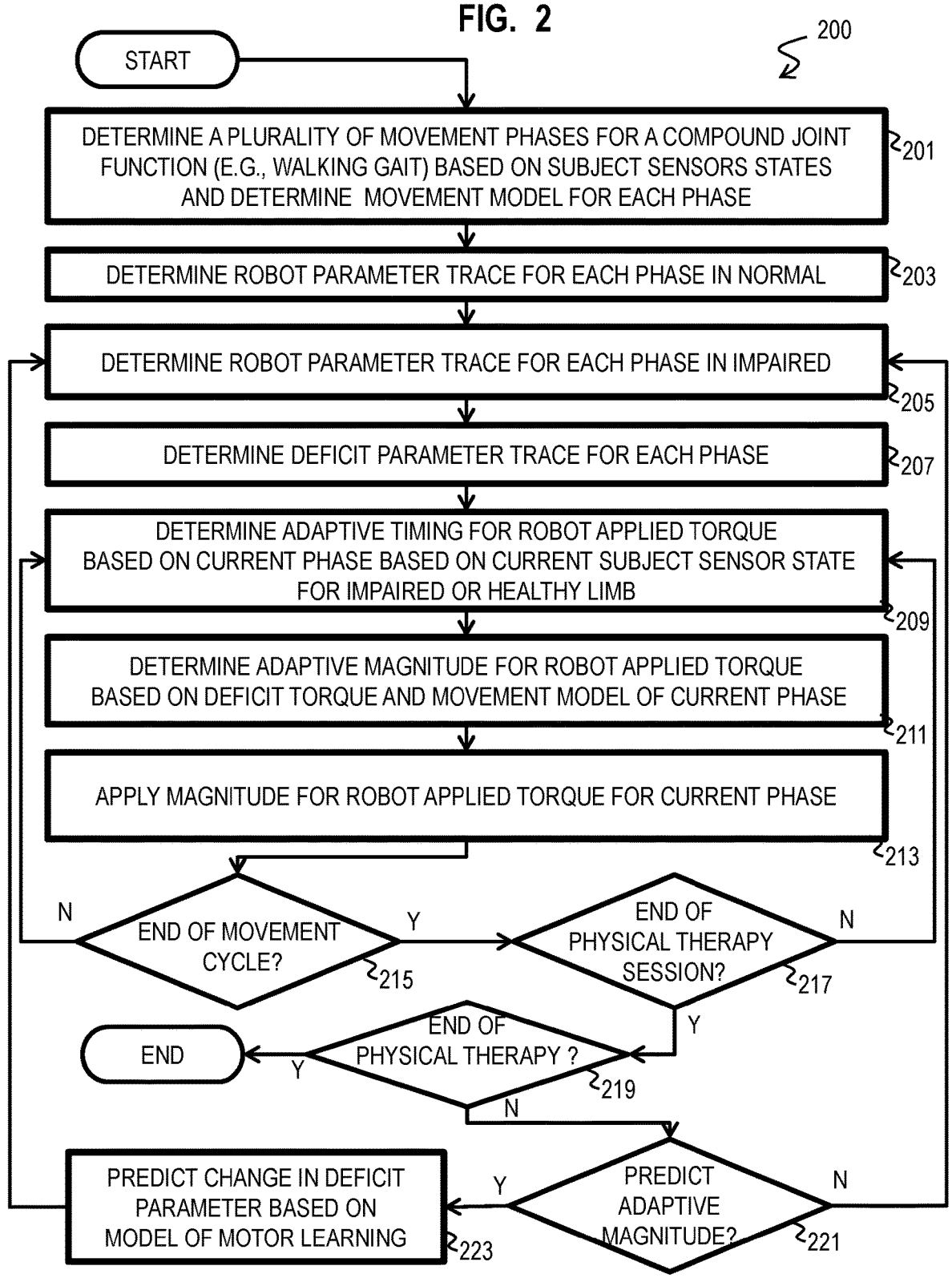

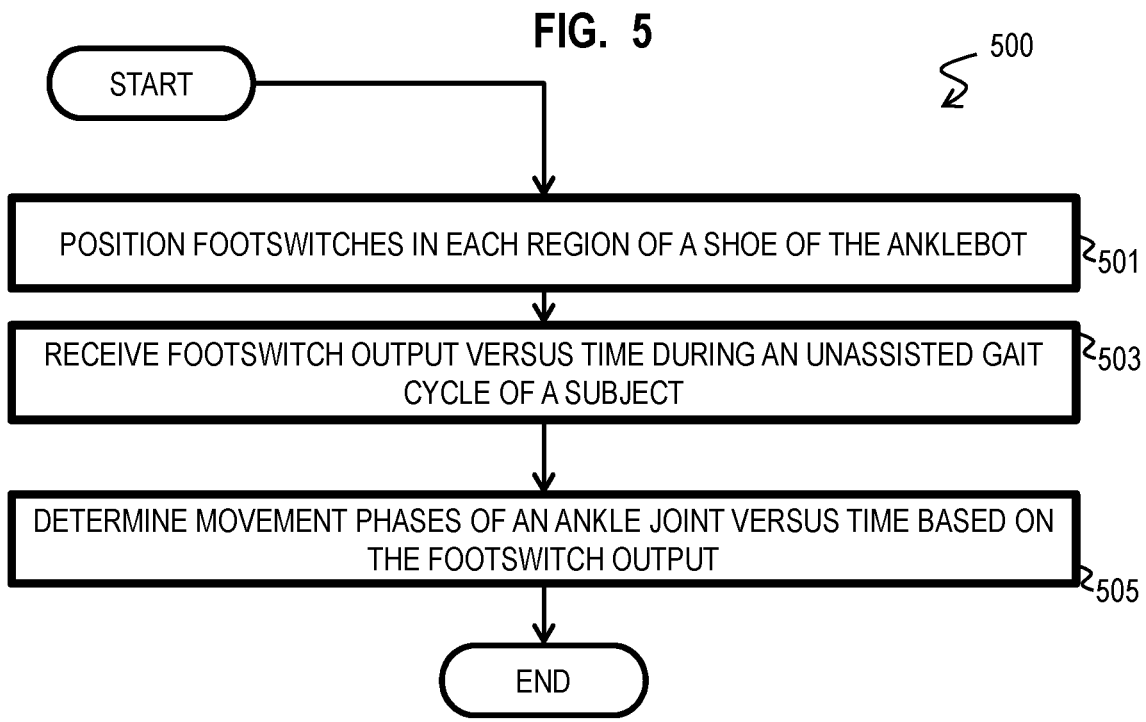

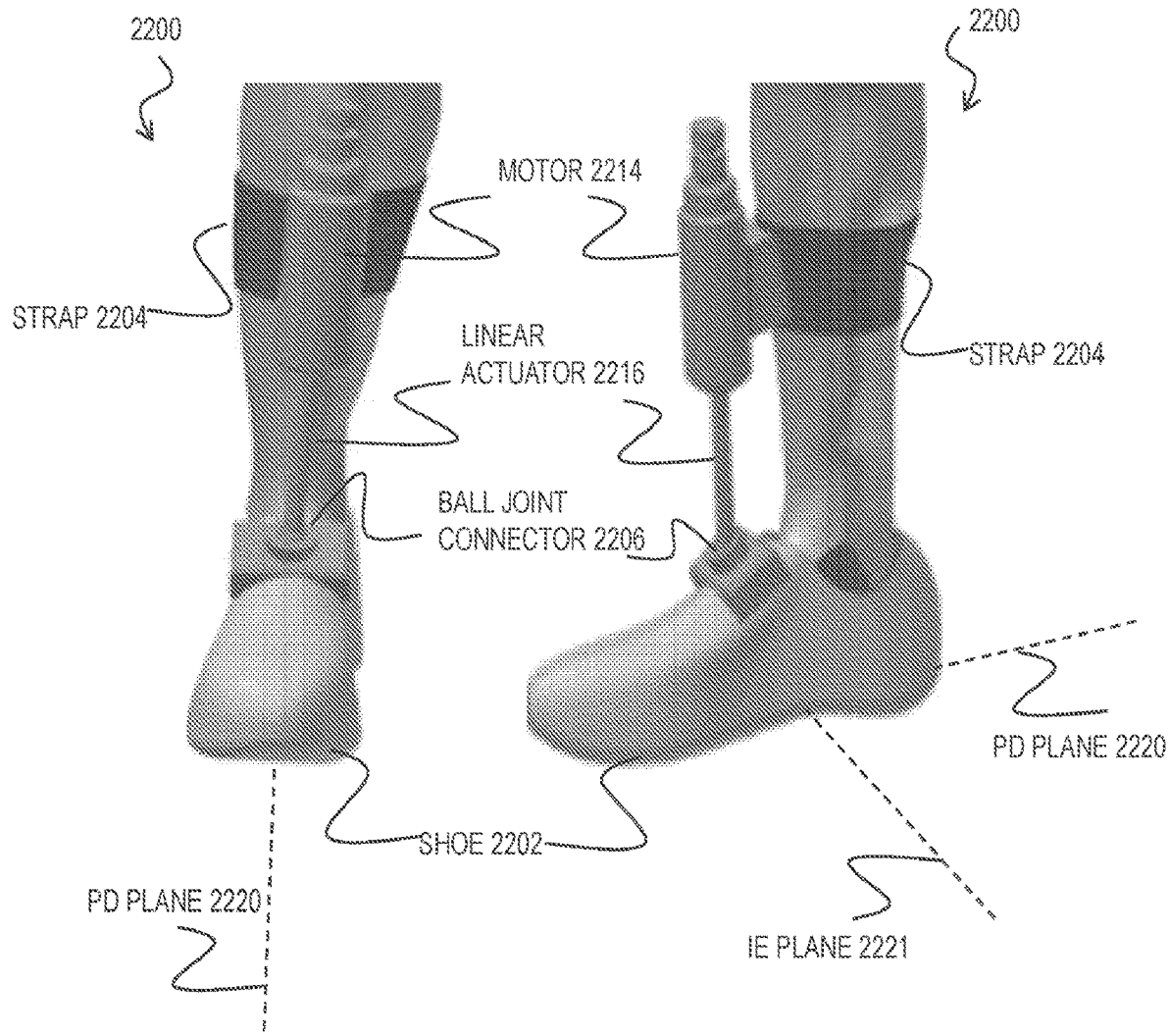

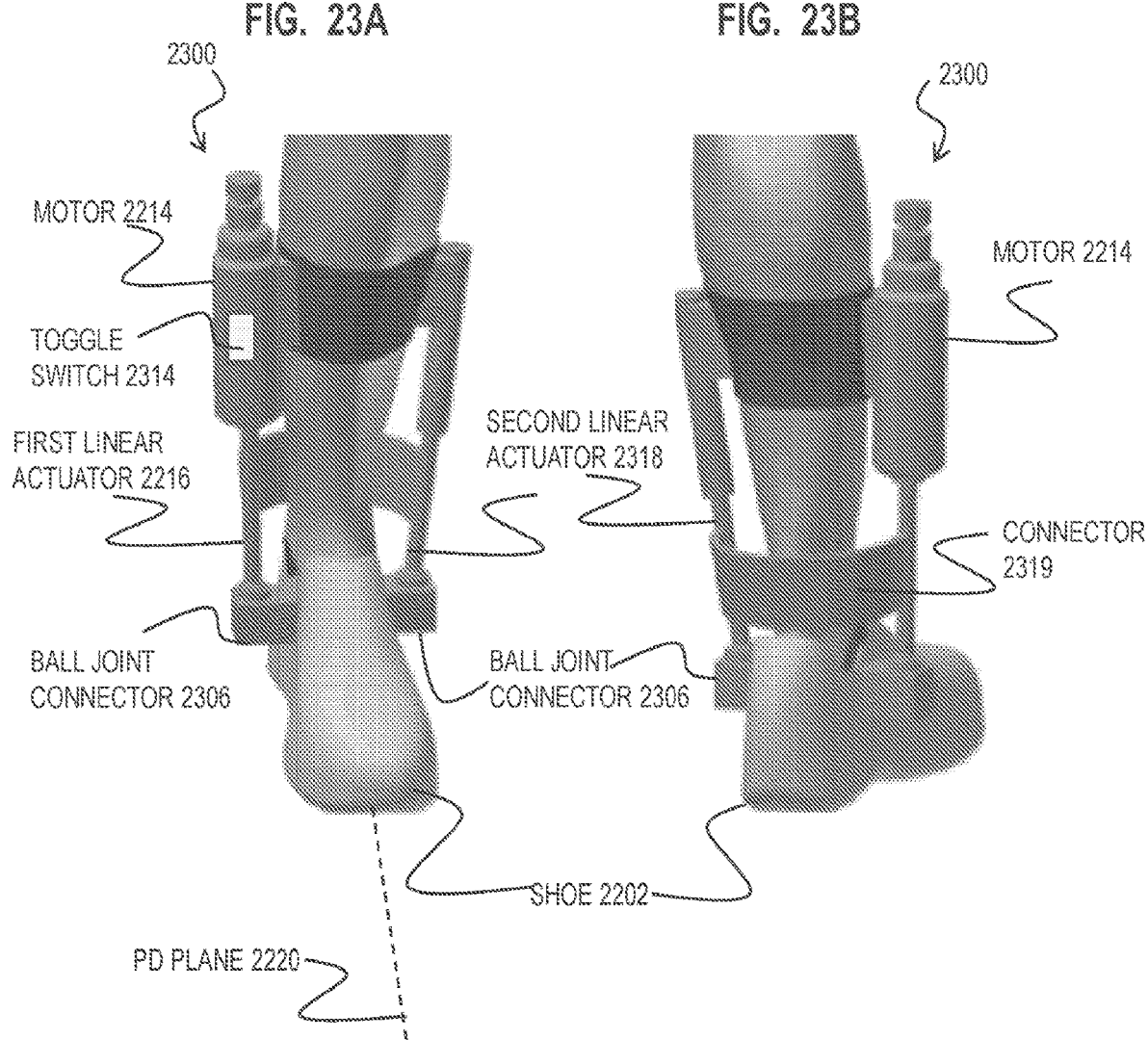

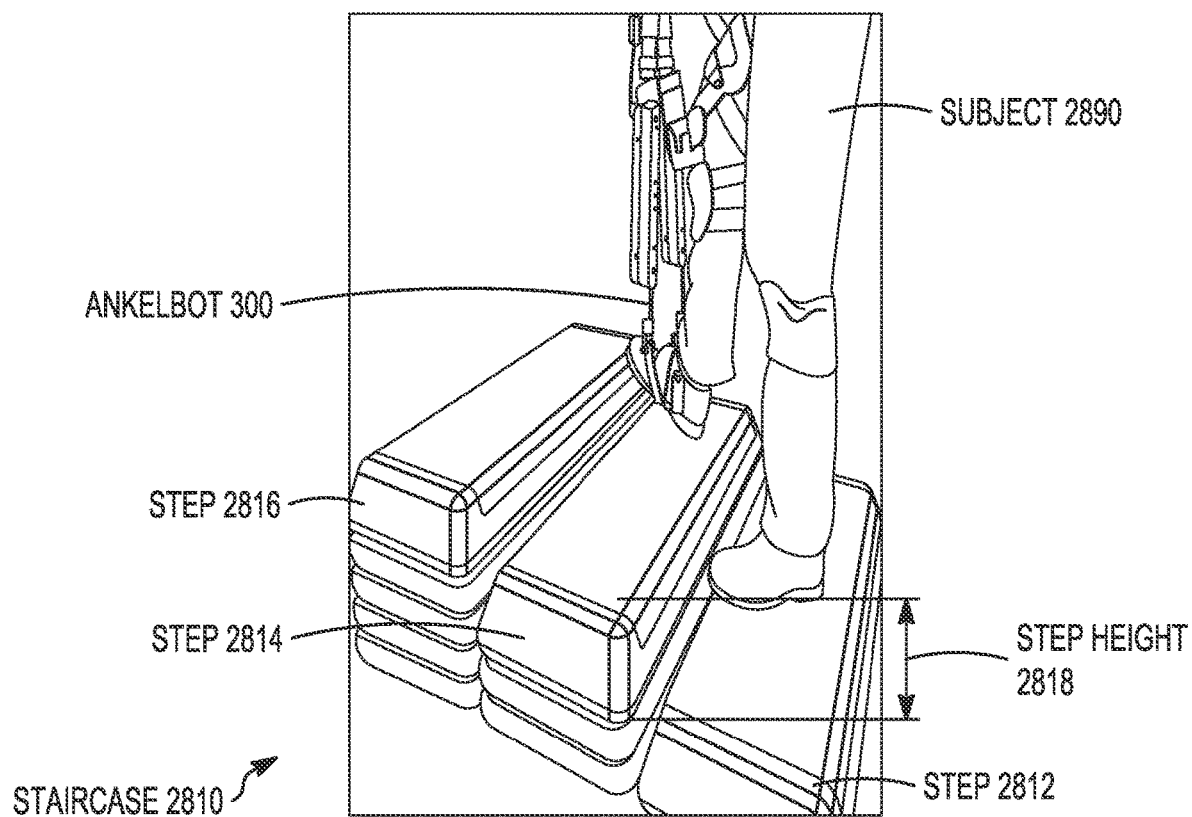
FIG. 28A
FIG. 28B
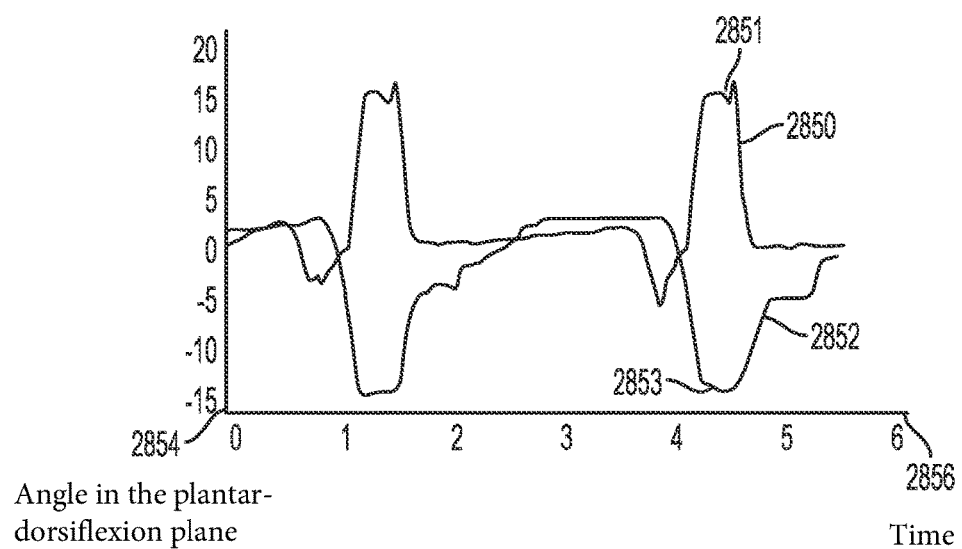
Angle in the plantar-dorsiflexion plane
Time

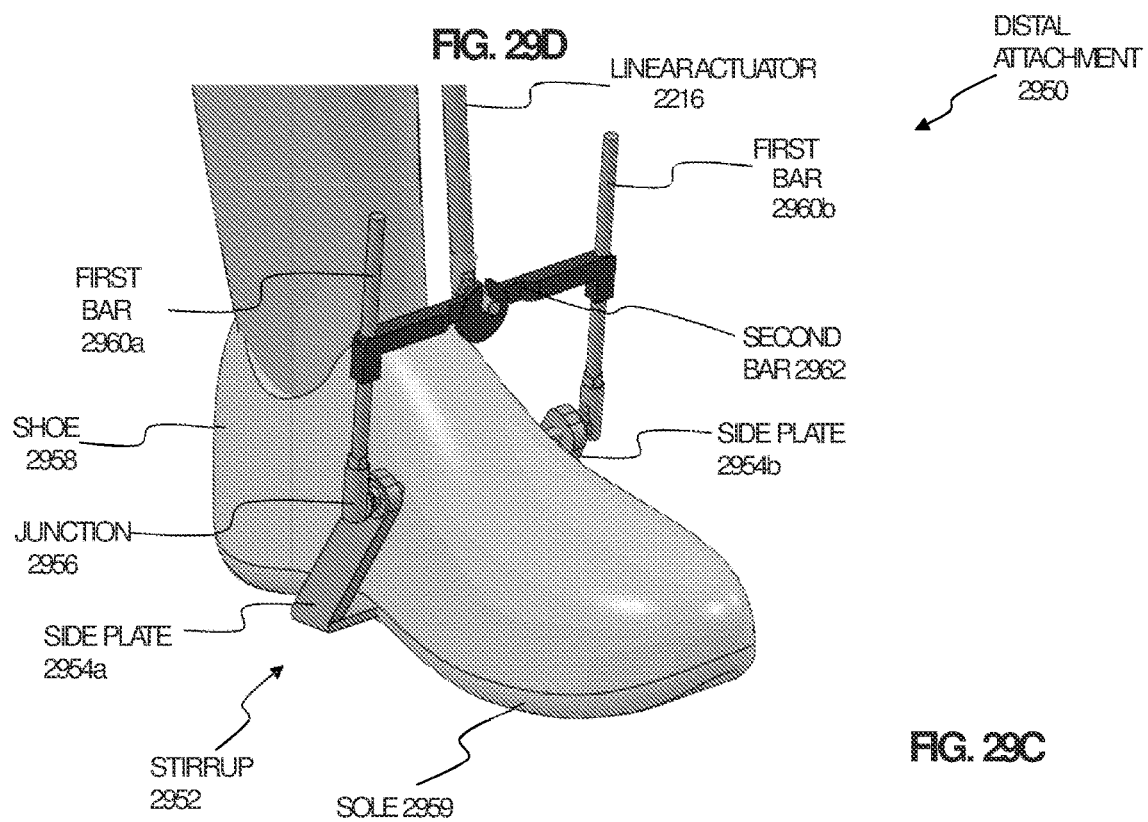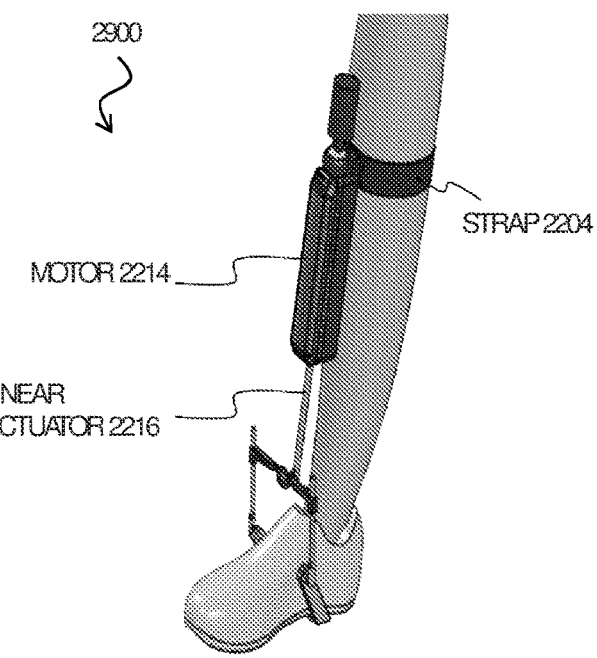

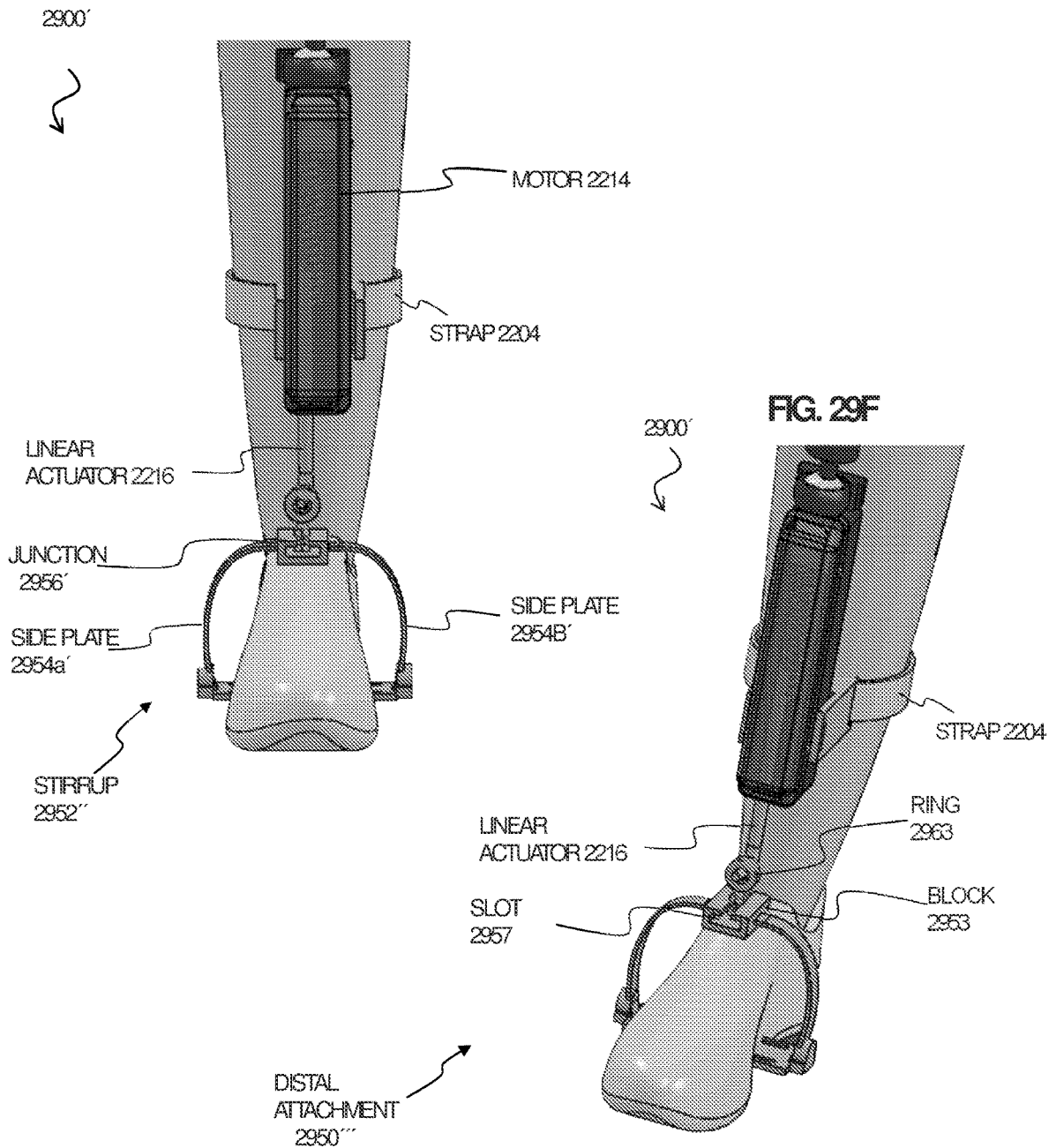

METHOD AND APPARATUS FOR PROVIDING ECONOMICAL, PORTABLE DEFICIT-ADJUSTED ADAPTIVE ASSISTANCE DURING MOVEMENT PHASES OF AN IMPAIRED ANKLE

CROSS-REFERENCE TO RELATED APPLICATIONS

This application is a 371 national stage application of PCT Application No. PCT/US2016/038370, filed Jun. 20, 2016 which claims benefit of Provisional Application No. 62/182,779, filed Jun. 22, 2015, under 35 U.S.C. § 119(e), the entire contents of which are hereby incorporated by reference as if fully set forth herein.

STATEMENT OF GOVERNMENTAL INTEREST

This invention was made with government support from the United States Department of Veterans Affairs. The government has certain rights in the invention.

BACKGROUND

When a patient suffers a medical condition, such as a stroke, that affects the patient's ability to move one or more joints, the patient routinely undergoes physical rehabilitation, in an effort to recover mobility and control of the joint. In one form of conventional physical rehabilitation, a therapist pushes or slides the patient's joint through a plurality of movement phases of a movement cycle. To reduce tedium and variability of such physical therapy, exo-skeletal robots have been introduced. A conventional form of such physical rehabilitation involves the use of the exo-skeletal robot that is attached to the impaired joint, to impose prescribed dynamics of a healthy joint on the impaired joint, over a plurality of movement phases.

SUMMARY

It is here recognized that conventional methods of physical rehabilitation for patients with impaired joints are deficient, since they employ exo-skeletal robots which impose prescribed dynamics of a healthy joint, which are at a normal speed and/or range of motion, onto the impaired joint of the patient, who may be moving at a reduced speed and/or range of motion. This mismatch between the imposed dynamics of a healthy joint on the impaired joint results in out-of-sync dynamics between the robot and the patient in which movement of the impaired joint is inhibited rather than assisted by the robot, and may even lead to destabilization of the patient.

In a first set of embodiments, an apparatus is provided for providing deficit-adjusted, adaptive assistance during a plurality of movement phases of an impaired ankle. The apparatus includes a variable torque motor configured to connect to an exo-skeletal ankle robot including a pair of beams connected to a pivot. The pair of beams are configured to be coupled to a first and second limb of a subject separated by an ankle of the subject. The variable torque motor is configured to impart a robot applied torque about the pivot in only a first plane. The apparatus further includes a processor with a sensor input configured to receive first data from at least one first sensor during a plurality of movement phases of a compound ankle function. The processor includes a memory with a sequence of instructions configured to, with the processor, cause the apparatus to determine a deficit parameter for each movement phase based on a respective robot state parameter applied to the exo-skeletal robot ankle by a normal subject and by an impaired subject. The memory and sequence of instructions are further configured to cause the apparatus to determine an adaptive timing for a robot-applied torque based on a current movement phase based on a current first data of the first sensor. The memory and sequence of instructions are further configured to cause the apparatus to determine an adaptive magnitude for the robot-applied torque based on the deficit robot state parameter for the current movement phase (for example, the robot-applied peak torque magnitude that varies during the swing phase from one gait cycle to another, or from step-to-step). The variable torque motor is in communication with the memory to receive the adaptive magnitude and the adaptive timing and is configured to impart the robot-applied torque at the adaptive magnitude in only the first plane to the pivot during the current movement phase based on the adaptive timing. The apparatus is portable such that the apparatus is configured to be carried by the subject.

In a second set of embodiments, a method is provided for providing deficit-adjusted adaptive assistance during a plurality of movement phases of an impaired ankle. The method includes determining, on a processor, a value for a deficit parameter for each movement phase of a compound ankle function, based on a difference between a robot state parameter trace for an exo-skeletal ankle robot for a normal subject and the robot state parameter trace for an impaired subject at each movement phase. The method further includes determining, on the processor, an adaptive timing for a robot-applied torque based on a current movement phase based on a current sensor state, from current sensor data. The method further includes determining, on the processor, an adaptive magnitude for the robot-applied torque based on the value of the deficit robot state parameter of the current movement phase. The method further includes applying, to the exo-skeletal robot ankle, the adaptive magnitude for the robot-applied torque in only a first plane for the current movement phase (for example, the swing phase of gait), based on the adaptive timing.

Still other aspects, features, and advantages of the invention are readily apparent from the following detailed description, simply by illustrating a number of particular embodiments and implementations, including the best mode(s) contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 2 is a flow diagram that illustrates an example of a method for providing deficit-adjusted adaptive assistance during a plurality of movement phases of an impaired joint, according to an embodiment;

FIG. 5 is a flow diagram that illustrates an example of a method for determining a plurality of movement phases for an ankle joint based on footswitch output, according to an embodiment;

FIGS. 22A and 22B are block diagrams that illustrate an example lightweight portable system for providing deficit-adjusted adaptive assistance during a plurality of movement phases of an impaired ankle joint, according to an embodiment;

FIGS. 23A and 23B are block diagrams that illustrate an example lightweight portable system for providing deficit-adjusted adaptive assistance during a plurality of movement phases of an impaired ankle joint, according to another embodiment;

FIG. 28A is the example system of FIG. 3 used by a subject during a staircase ascend;

FIG. 28B is a pair of graphs that illustrate an example of angle traces of the subject in FIG. 28A measured in the plantar-dorsiflexion_plane during assisted and unassisted modes of the system;

FIGS. 29A-29C are block diagrams that illustrate an example lightweight portable system for providing deficit-adjusted adaptive assistance during a plurality of movement phases of an impaired ankle joint, according to an embodiment;

FIG. 29D is a block diagram that illustrates an example of a distal attachment used as a beam to couple the linear actuator to the foot in the system of FIGS. 29A-29C;

FIGS. 29E-29F are block diagrams that illustrate an example lightweight portable system for providing deficit-adjusted adaptive assistance during a plurality of movement phases of an impaired ankle joint, according to an embodiment;

DETAILED DESCRIPTION

Figure 1A:
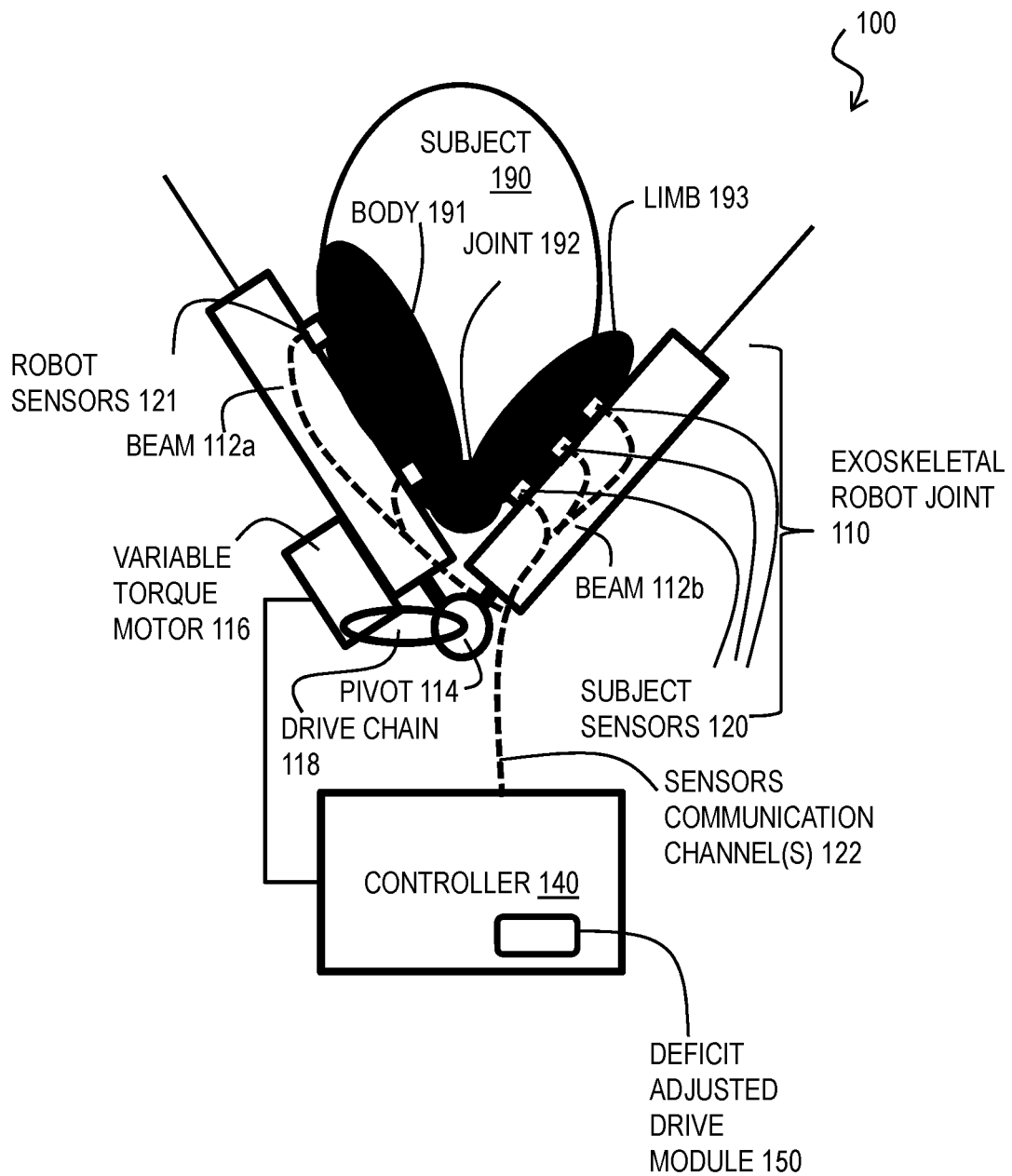
FIG. 1A is a block diagram that illustrates an example system for providing deficit-adjusted adaptive assistance during a plurality of movement phases of an impaired joint, according to an embodiment.

A method and apparatus are described for providing deficit-adjusted adaptive assistance during a plurality of movement phases of an impaired joint. For purposes of the following description, an impaired joint is defined as any joint of the human body experiencing impaired movement, due to an injury or medical condition sustained by the patient. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of providing deficit-adjusted adaptive assistance over a plurality of movement phases during training of an impaired joint, such as an ankle joint, a hip joint, or a knee joint. However, the invention is not limited to this context. In other embodiments, deficit-adjusted adaptive assistance is provided over a plurality of movement phases during training or strengthening of a healthy joint. In other embodiments, methods or apparatus is provided to utilize modular robotics in diverse neurological populations for rehabilitation of impaired joints to improve mobility function. Applications of this embodiment encompass different neurological diseases and different joints, as described in more detail in later sections.

Some embodiments are utilized in the context of amputation prostheses that is designed to replace lost limbs in a patient, to help the patient recover mobility and sensory function. Some embodiments are used in the context of regulating foot pressure and ground reaction forces for dealing with diabetic neuropathy. Some embodiments are utilized in the context of motor learning to improve outcomes for podiatry, orthopedics, and prosthetics. Some embodiments are utilized in the context of improving walking and balancing function after a patient experiences a stroke, by means of increasing contribution of a paretic (e.g. affected) ankle. Some embodiments are used in the context of Multiple Sclerosis (MS), Parkinson's disease, or neuropathy or peripheral neuropathy.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4. As used herein a value of about a certain number is understood to mean either a factor of two with the certain number or an implied precision given by a least significant digit for the certain number.

1. Overview

When a patient suffers an injury or medical condition that affects one or more of their joints, the patient's ability to move and control the joint is impaired. For example, the patient may not be able to move the joint at a torque that was previously achievable prior to the injury or medical condition. Additionally, the patient may not be able to move the joint through a range of motion, at a speed or at an orientation that was previously achievable prior to the injury or medical condition. According to various embodiments, sensors are provided to measure these parameters of movement of the impaired joint, in order to determine an adaptive magnitude or timing of assistance, or some combination, for the impaired joint during treatment.

When a joint is moved through a range of motion, this range of motion includes a plurality of movement phases. When a patient suffers an injury or medical condition, which affects the mobility of one or more joints, this impaired joint may be affected during one or more of these movement phases and in the timing of those movement phases. For example, a patient with an impaired joint may only experience impaired movement of the joint during a first movement phase of the joint and be capable of normal movement of the joint during the remaining movement phases, however the timing of those movement phases may be slowed. According to various embodiments, sensors are provided to detect when a joint is in each of the impaired movement phases, in order to determine an adaptive timing of assistance for the impaired joint during treatment. In various embodiments, the magnitude of the deficit is determined during each movement phase in order to determine an adaptive magnitude for assistance during each movement phase.

FIG. 1A is a block diagram that illustrates an example system 100 for providing deficit-adjusted adaptive assistance over a plurality of movement phases during training of an impaired joint 192, according to one embodiment. The impaired joint 192 may be any joint connecting a limb 193 to a body 191 of a subject 190, where the subject 190 has limited mobility of the impaired joint 192, due to a sustained injury or medical condition. During a compound function of the joint 192, the impaired joint 192 moves through a plurality of movement phases. Although a subject 190 with body part 191, joint 192 and limb 193 is depicted for purpose of illustration, the subject 190 is not part of the system 100. The system 100 includes an exo-skeletal joint 110, subject sensors 120 and controller 140 configured with a deficit adjusted drive module 150.

The exo-skeletal joint 110 includes a pivot 114 connecting a pair of beams 112a, 112b respectively secured to the body 191 and limb 193 on either side of the subject's joint 192.

The exo-skeletal joint 110 also includes a variable torque motor 116 that imparts torque on the pivot 114 (e.g., through a drive chain 118). In some embodiments, the exo-skeletal robot joint 110 also includes one or more robot sensors 121 to determine non-torque state of the robot 110, such as a sensor for the angle between beams 112a and 112b.

Figure 14:
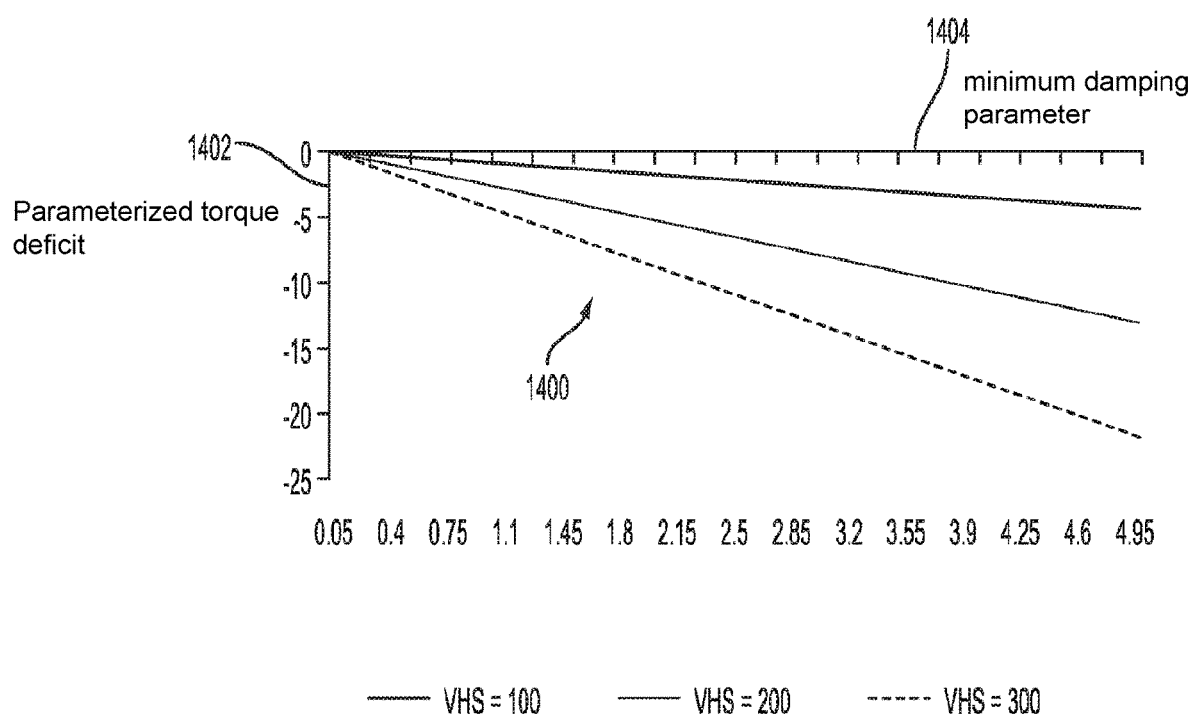
FIG. 14 is a graph that illustrates an example of a parameterized deficit torque trace based on a minimum damping parameter, according to an embodiment.
Figure 15:
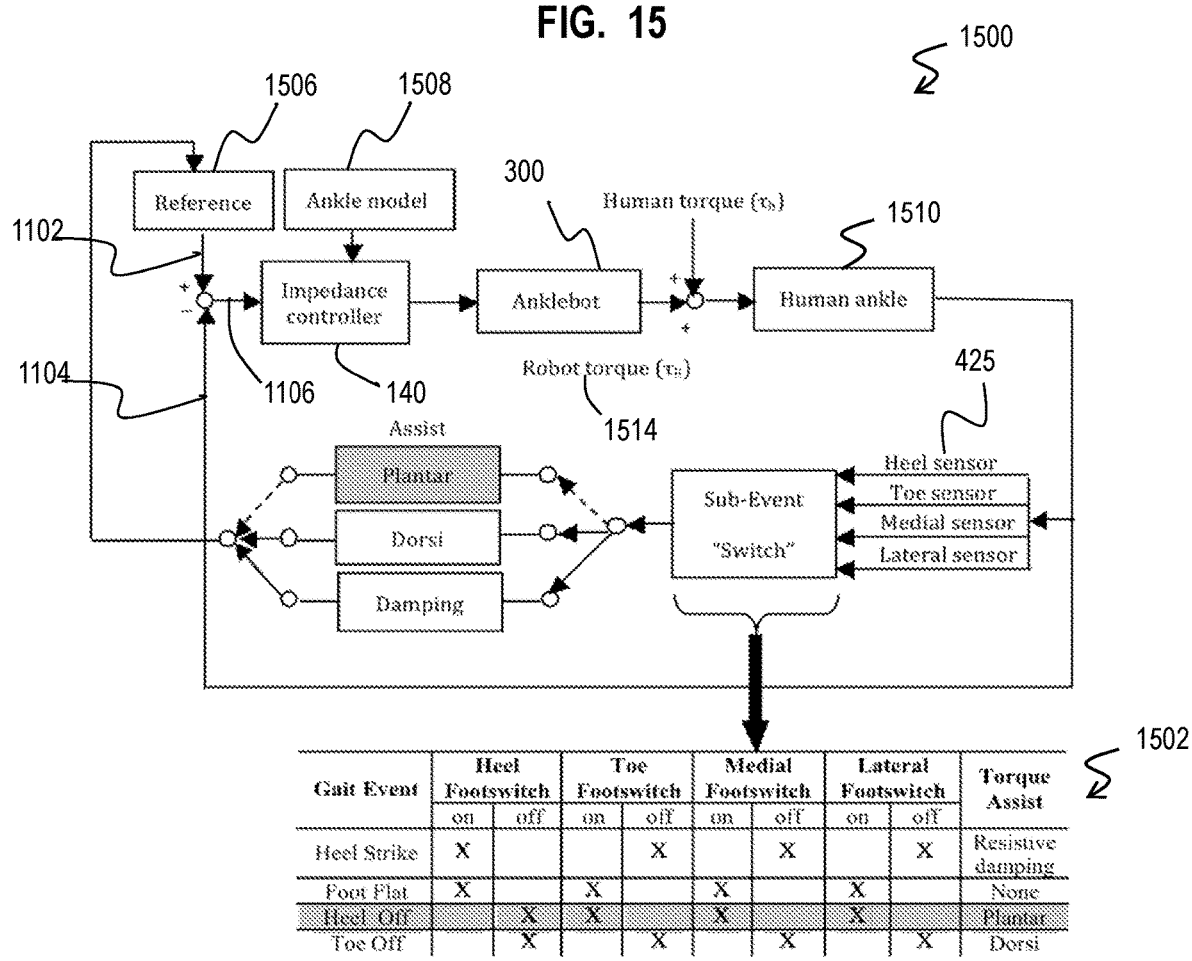
FIG. 15 is a block diagram that illustrates an example system for providing deficit-adjusted adaptive assistance during a plurality of movement phases of an impaired ankle joint, according to an embodiment.

The subject sensors 120 (also called sensors 120, for convenience) output a plurality of states, where at least some outputted state indicates a respective movement phase of the impaired joint 192. In one embodiment, the sensors 120 output a first state when the impaired joint 192 is in a first movement phase and output a second state when the impaired joint 192 is in a second movement phase. When not being driven, the variable torque motor 116 also outputs a current or voltage that responds to a torque applied by the subject 190 to the pivot 114 while the subject is connected to (e.g., wearing) the exo-skeletal robot joint 110, in some embodiments. In some embodiments, the current or voltage output by the motor 116 is used as a torque sensor to measure a torque applied by external forces, such as that applied by movement of the subject's joint 192 during each movement phase. In some embodiments, position data is inferred from the torque measurements from the motor 116. In some embodiments, one or more of the additional robot sensors 121 measures position data, such as velocity and/or angle of the joint 192 during each movement phase. As further illustrated in FIG. 1A, the controller 140 drives the torque motor 116, and receives robot state parameter data that is based on the current or voltage output by the torque motor 116 or the position or angle data output by the additional robot sensors 121 when the beams 112a, 112b are moved by external forces, or some combination, and is connected to the sensors 120 and 121, along wired or wireless sensor communication channels 122. In various embodiments, the controller 140 comprises a general purpose computer system, as depicted in FIG. 14 or a chip set as depicted in FIG. 15, and instructions to cause the computer or chip set to perform one or more steps of a method described below with reference to FIG. 2.

Figure 1B:
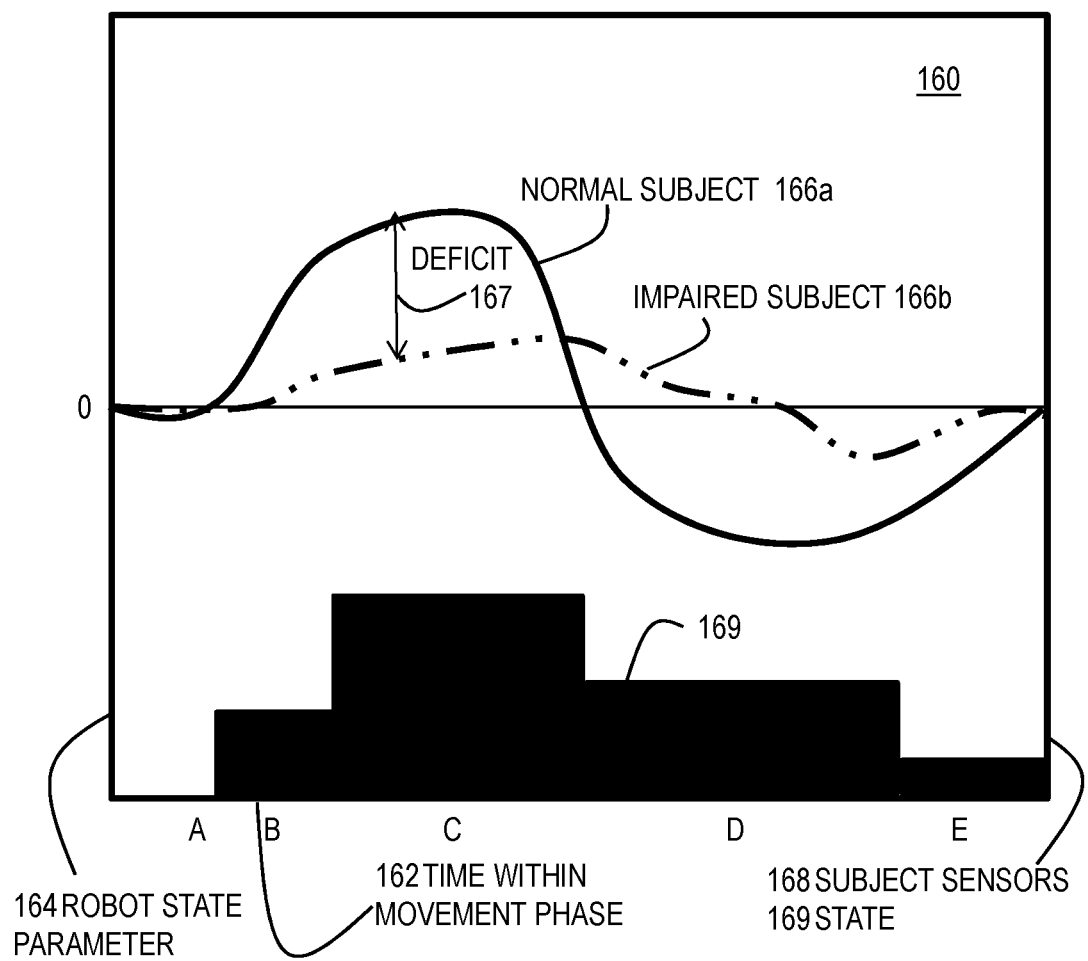
FIG. 1B illustrates an example of a robot state parameter trace for a normal and impaired subject and an applied robot state parameter over a plurality of movement phases, according to an embodiment.

FIG. 1B illustrates an example graph 160 of a robot state parameter trace 166a, 166b for a normal and impaired subject, according to one embodiment. The horizontal axis 162 indicates time, in relative units within a movement phase sequence. The left vertical axis 164 indicates the robot state parameter, such as subject achieved angle or subject applied torque, in relative units; and, the right vertical axis 168 indicates state of the collection of one or more subject sensors 120, in integer units. Trace 169 depicts changes in sensor state among a sequence of 5 different movement phases over time, based on the right vertical axis 168. Each different phase is associated with a different state of the output from sensors 120. For example, phase A is associated with no output from any sensor, and phase C is associated with maximum output from one or more sensors.

The trace 166a is based on the robot state parameter values as the normal subject moves the joint 192 through the plurality of movement phases, and plotted relative to left vertical axis 164. Similarly, the trace 166b is based on the robot state parameter as the impaired subject moves the joint 192 through the plurality of movement phases, and plotted relative to left vertical axis 164. The time axes of the two traces are adjusted relative to each other so that the movement phase for each trace is aligned, as indicated on the horizontal axis 162. This accounts for the impaired patient progressing through the movement phases at a different rate than a normal subject. The controller 140 receives the robot state parameter traces 166a, 166b data. The controller 140 also receives the sensor states 168 from the sensors 120, which indicate a current movement phase of the joint 192. The drive module 150 causes the controller 140 to determine a deficit trace 167 for each movement phase, based on a difference between the respective robot state parameter traces 166a, 166b. The drive module 150 also is configured to drive the motor 116 based on the difference. In one embodiment, the drive module 150 determines an average deficit 167 for each movement phase by computing a difference between the robot state parameter trace 166a of the normal subject and the robot state parameter trace 166b of the impaired subject, for each movement phase. The applied robot state parameter imparted on the joint 192 by the variable torque motor 116 depends on the movement phase determined by the drive module 150 and an adaptive magnitude from the drive module 150 for each movement phase, based on the movement phase and the associated deficit parameter 167 for each movement phase.

In some embodiments, a movement model is used to describe one or more of the movement phases indicated by trace 169. The movement model parameterizes the robot state parameter during each movement phase based on a set of one or more model parameters. A normal subject is expected to show one set of values for those model parameters of the model. An impaired subject is expected to show some deviation from that set of values. In some embodiments, using a movement model, the decision whether to apply a torque to the exo-skeletal robot joint to assist an impaired subject, and the amount, is based on whether the set of values for the set of model parameters for the impaired patient is above or below a threshold set of values that represent some percentage of the set of normal values.

If the robot state parameter deficit 167 in a current movement phase is less than a robot state parameter threshold, the adaptive magnitude for the current movement phase is adjusted such that the controller 140 does not transmit an applied torque signal to the variable torque motor 116 during the current movement phase. If the robot state parameter deficit 167 in a current movement phase is greater than the robot state parameter threshold, the adaptive magnitude for the current movement phase is adjusted such that the controller 140 transmits the applied torque signal to the variable torque motor 116 during the current movement phase.

FIG. 2 is a flow diagram that illustrates an example of a method 200 for providing deficit-adjusted adaptive assistance during a plurality of movement phases of an impaired joint 192, according to one embodiment. For example, the steps of method 200 are applied by module 150 of controller 140. Although the flow diagram of FIG. 2 is depicted as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

After starting, in step 201, the plurality of movement phases for the compound joint function are determined, on the module 150. In some embodiments, the phases are determined by analyzing movements observed in video of one or more normal subjects performing the compound movement. The states of the sensors 120 for each movement phase are then determined by recording for a normal subject the sensor state of the sensor 120 for each phase. In some embodiments, the sensor states associated with each movement phase are stored on a memory associated with module 150. In some embodiments, in step 201, the movement model for each movement phase is also determined. For example, the movement model is programmed as an instruction set on the module 150. In an example embodiment, described in a later section, mathematical movement models for an ankle during various phases of walking are programmed into module 150.

In step 203, the robot state parameter, such as the angle of the beams 112 in a normal subject during each movement phase is determined, e.g., based on new or historical records of the angle measurements from the sensors 121, when the motor 116 is not driven by controller 140. In some embodiments, during step 203, the exo-skeletal robot joint 110 is attached to a normal subject who moves the beams 112 through the plurality of movement phases while the robot joint 110 does not apply torque.

During step 205, the exo-skeletal robot joint 110 is attached to an impaired subject who moves the beams 112 through the plurality of movement phases while the robot joint 110 does not apply torque. As the impaired subject moves the beams 112 through the plurality of movement phases, the sensors 120 transmit the sensor states 168 to the module 150 along the sensor communication channels 122, so the module 150 can determine the movement phase that correspond to the sensor states 168. Additionally, as the impaired subject moves the beams 112 through the plurality of movement phases, the sensors 120 measure the robot state parameter, such as the angle of the joint 192 during movement of the joint 192 during each movement phase and transmit this robot state parameter data to the controller. If a movement model is used, then the module 150 compares the measured model parameter of movement of the beams 112 during each movement phase with the respective threshold parameter of movement for each movement phase.

In step 207, the deficit parameter trace 167 for each movement phase is determined by the module 150. After receiving the robot state parameter traces 166a, 166b in steps 203, 205, in step 207 the module 150 determines the deficit parameter trace 167 by computing a difference between the normal robot state parameter trace 166a and the impaired robot state parameter trace 166b, for each movement phase. In embodiments using a movement model, the parameter deficit is parameterized as a value of the one or more model parameters.

In step 209, the adaptive timing for the robot-applied torque is determined for a current movement phase by the module 150 based on the current sensor state. For example, if the current sensor state is the maximum of curve 169 in FIG. 1B, then module 150 determines that the current movement phase is phase C. The module 150 then compares the deficit parameter 167 in the current movement phase with the robot state parameter threshold. If the module 150 determines that the parameter deficit 167 in the current movement phase is less than the robot state parameter threshold, the module 150 does not transmit an applied torque signal to the variable torque motor 116 during the current movement phase. If the module 150 determines that the deficit parameter 167 in the current movement phase is greater than the robot state parameter threshold, the module 150 transmits an applied torque signal to the variable torque motor 116 during the current movement phase.

In step 211, the adaptive magnitude for the robot-applied torque is determined for a current movement phase by the module 150. In order to determine the adaptive magnitude of the applied torque during the current movement phase (e.g., phase C), the module 150 uses the calculated deficit parameter 167 for the current movement phase, or the parameterized value of the movement model. In an embodiment, although the deficit parameter 167 may vary within a current movement phase, the module 150 uses the determined movement model from step 201 for the current movement phase to determine a fixed adaptive magnitude, or a model curve of the magnitude, for the applied torque throughout the current movement phase (e.g., phase C).

In step 213, the adaptive magnitude of the robot applied torque is applied by the variable torque motor 116 on the pivot 114 for the current movement phase, based on the adaptive timing for the current movement phase. During step 213, the module 150 transmits the adaptive magnitude data for the applied torque for the current movement phase to the variable torque motor 116, based on the adaptive timing for the current movement phase from step 209. Upon receiving the adaptive magnitude data from the module 150, the variable torque motor 116 imparts the applied torque with the adaptive magnitude on the pivot 114 during the current movement phase. This applied torque assists the subject 190 in moving the limb 193 relative to the body 191, thus training the joint 192.

In step 215, a determination is made by the module 150 of whether the joint 192 has reached the end of a movement cycle, based on whether the beams 112 has reached the last movement phase of the movement cycle. In order to determine whether the joint 192 has reached the end of the movement cycle, the module 150 determines whether the sensor state 168 received by the module 150 from the sensors 120 indicate that the beams 112 are in the last movement phase (e.g., phase E). In step 201, the module 150 determined the sensor states 168 for each movement phase, including the sensor state 168 indicating the last movement phase. Thus, in step 215, the module 150 compares the sensor state 168 for the last movement phase with the sensor state 168 received from the sensors 120 for the current movement phase. If the module 150 determines that the beams 112 have not reached the last movement phase, the method returns to step 209. If the module 150 determines that the beams have reached the last movement phase, the method continues to step 217.

In step 217, a determination is made by the module 150 of whether a physical therapy session has ended. In order to determine whether the physical therapy session has ended, the module 150 determines how many movement cycles of the beams 112 have been completed and compares this number with a threshold number of movement cycles for a physical therapy session. If the beams 112 have completed the threshold number of movement cycles, the module 150 determines that the physical therapy session has ended and the method moves to step 219. If the beams 112 have not completed the threshold number of movement cycles, the module 150 determines that the physical therapy session has not ended and the method moves to step 209, described above.

In step 219, a determination is made by the module 150 of whether physical therapy has ended for the patient. In order to determine whether the physical therapy for the patient has ended, the module 150 determines how many physical therapy sessions have been completed by the patient and compares this number with a threshold number of physical therapy sessions for physical therapy. If the patient has completed the threshold number of physical therapy sessions, the module 150 determines that the physical therapy for the patient has ended and the method ends. If the patient has not completed the threshold number of physical therapy sessions, the module 150 determines that the physical therapy for the patient has not ended and the method moves to step 221.

In step 221, a determination is made by the module 150 of whether to predict a change in the adaptive magnitude of the applied torque, based on a progress of the patient. If the module 150 determines not to predict a change in the adaptive magnitude of the applied torque, and instead to re-measure a change in the adaptive magnitude of the applied torque, the method moves to step 205. The method then measures any change in the adaptive magnitude of the applied torque, by re-measuring the deficit parameter 167 for each movement phase in steps 205, 207, 209 and then using this re-measured deficit parameter 167 to measure a change in the adaptive magnitude in step 211 for each movement phase. If the module 150 determines to predict the change in the adaptive magnitude of the applied torque, the method moves to step 223.

In step 223, a prediction in the change of the adaptive magnitude of the applied torque is made by the module 150. In order to predict the change of the adaptive magnitude of the applied torque, the module 150 uses a model of motor learning, which estimates changes in the deficit parameter 167, based on one or more robot state parameters, such as the number of movement cycles completed. After the module 150 uses the model of motor learning to predict the change in the deficit parameter 167, the method confirms this prediction by moving to steps 205, 207, where the deficit parameter 167 is re-measured. In an embodiment, after the module 150 uses the model of motor learning to predict the change in the deficit parameter 167, the method need not confirm the predicted change in the deficit parameter 167 and may return directly to step 209.

2. Example Embodiments

A. Ankle

One example embodiment of the invention is utilized in the context of improving walking and balancing function after a patient experiences a stroke, by means of increasing contribution of a paretic (e.g. affected) ankle, since the ankle plays an important role in the biomechanics of gait and balance. Following a stroke, some (or all) of these ecological aspects of gait are disrupted. For example, "drop foot" is a common impairment caused by a weakness in the dorsiflexor muscles that lift the foot. The presence of drop foot impedes the ability of the impaired foot to sufficiently clear the ground when transitioning from a stance phase to a swing phase of a gait cycle that is necessary for safe and efficient walking, as discussed below. As a result, drop foot often leads to one or more complications during walking, including "toe drag" (that is, dragging of the impaired foot during the swing phase of the gait cycle); "foot slap" (that is, uncontrolled initial foot contact with the ground), and/or lateral instability during the stance phase of the gait cycle, a cause of inversion (inward twist of the foot toward its midline).

Figure 3:
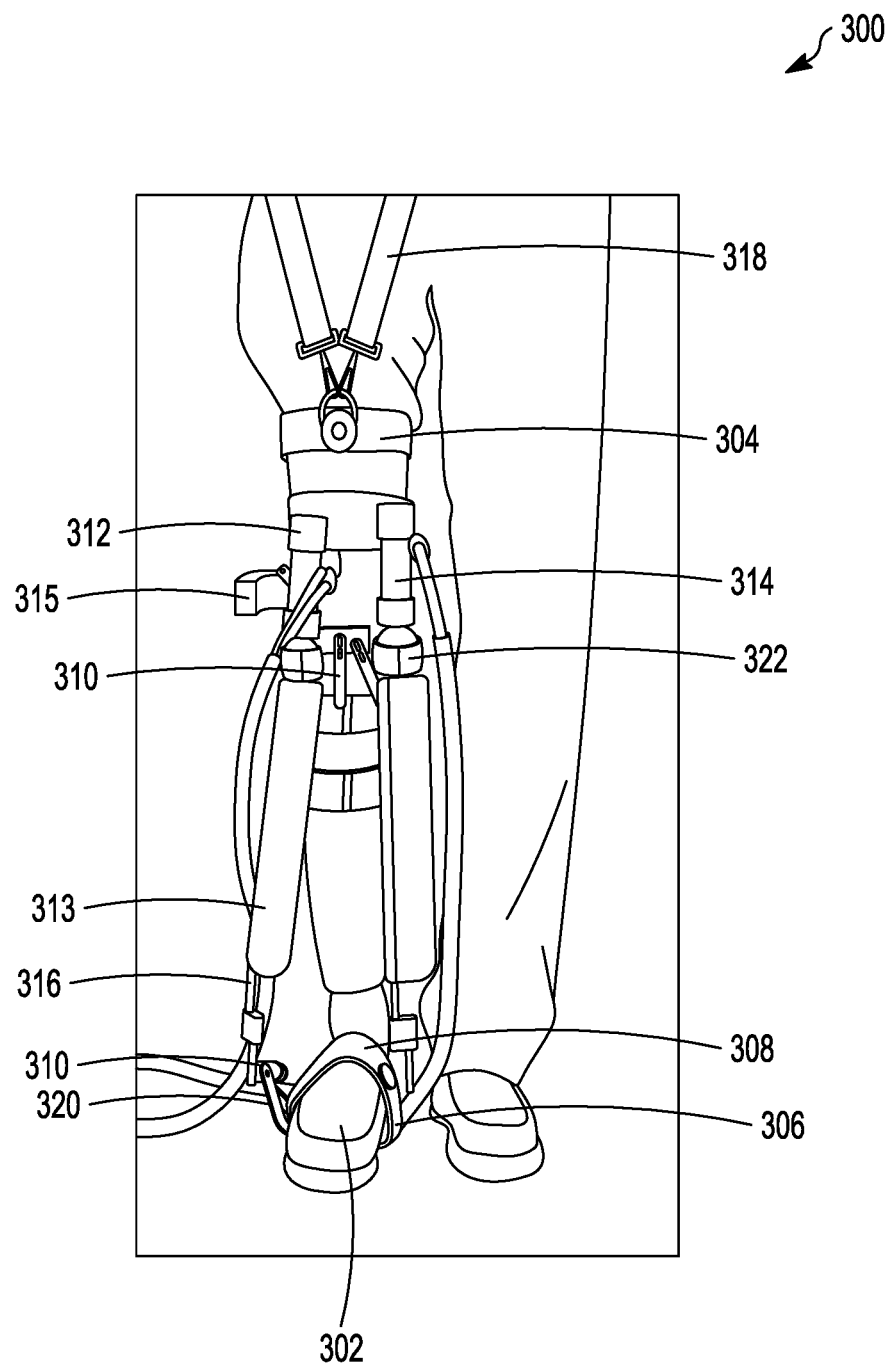
FIG. 3 illustrates an example system for providing deficit-adjusted adaptive assistance during a plurality of movement phases of an impaired ankle joint, according to an embodiment.

According to an example embodiment, the exo-skeletal robot joint 110 is an anklebot. FIG. 3 is a photograph that illustrates an example system for providing deficit-adjusted adaptive assistance during a plurality of movement phases of an impaired ankle joint, according to an embodiment. The system includes an anklebot 300 which is secured to the body and foot on either side of the subject's ankle joint. As illustrated in FIG. 3, the anklebot 300 includes a shoe 302 (corresponding to beam 112b for connection to limb 193) and a knee brace 304 which are worn by the subject and secured to the subject with quick connectors 306. A strap 308 is attached over a bridge of the subject's foot. The rest of the anklebot 300 is then mounted to the knee brace 304 using a pair of quick locks 310.

The anklebot 300 includes a motor 314 (corresponding to motor 116) that is connected to the shoe 302 through a pair of linear actuators 316 (corresponding to beam 112a and drive chain 118) and selectively imparts torque on the shoe 302 around the ankle joint through the pair of linear actuators 316. In an example embodiment, the motor 314 is a pair of brushless dc motors, each capable of generating 0.25 Newton-meters (N-m) of continuous stall torque and 0.8 Nm of instantaneous peak torque. The traction drives 316 are connected to either side of the shoe 302 using a quick lock 310 and a ball joint 320 (corresponding to pivot 114) and are connected to the motor 314 at a ball joint 322. A first position sensor 312 (corresponding to one robot sensor 121) measures the position or angle of the shoe 302 and transmits this position or angle information to the motor 314, to commutate the motor 314. In an example embodiment, the first position sensor 312 is a rotary encoder. A second position sensor 313 (corresponding to another robot sensor 121) is housed within a black casing near a drive shaft of the linear actuator 316. The second position sensor 313 measures the position or angle of the shoe 302 and transmits this position or angle information to a controller 140 (not shown). In an example embodiment, the second position sensor 313 is a linear incremental optical encoder. A knee potentiometer 315 is also provided to measure an angle of the knee and transmits this angle information to the controller 140. The motor 314 may be used as a torque sensor and communicate current or voltage information to the controller 140 that can be used to measure an imparted torque around the ankle joint by the subject. As illustrated in FIG. 3, the anklebot 300 also includes a shoulder strap 318, to optionally support a weight of the subject during the use of the anklebot 300.

In an example embodiment, the anklebot 300 is a 3-degree of freedom (DOF) wearable robot, back-drivable with low intrinsic mechanical impedance that weighs less than 3.6 kg. It allows normal range of motion (ROM) in all 3 DOF of the foot relative to the shank during walking overground, on a treadmill, or while sitting. In an example embodiment, the anklebot 300 provides actuation in two of the ankle's 3 DOF, namely plantar-dorsiflexion and inversion-eversion via the two linear actuators 316 mounted in parallel. In an example embodiment, internal-external rotation is limited at the ankle with the orientation of the foot in the transverse plane being controlled primarily by rotation of the leg. If both actuators 316 push or pull in the same direction, a DP (dorsiflexion-plantar) torque is produced. Similarly, if the two actuators 316 push or pull in opposite directions, inversion-eversion torque results. In an example embodiment, the anklebot 300 allows 25° of dorsiflexion, 45° of plantar-flexion, 25° of inversion, 20° of eversion, and 15° of internal or external rotation. These limits are near the maximum range of comfortable motion for normal subjects and beyond what is required for typical gait. In an example embodiment, the anklebot 300 can deliver a continuous net torque of approximately 23 Nm in DP torque and 15 Nm in eversion-inversion (IE) torque. In an example embodiment, the anklebot 300 has low friction (0.744 Nm) and inertia (0.8 kg per actuator for a total of 1.6 kg at the foot) to maximize the back-drivability.

Figure 4A:
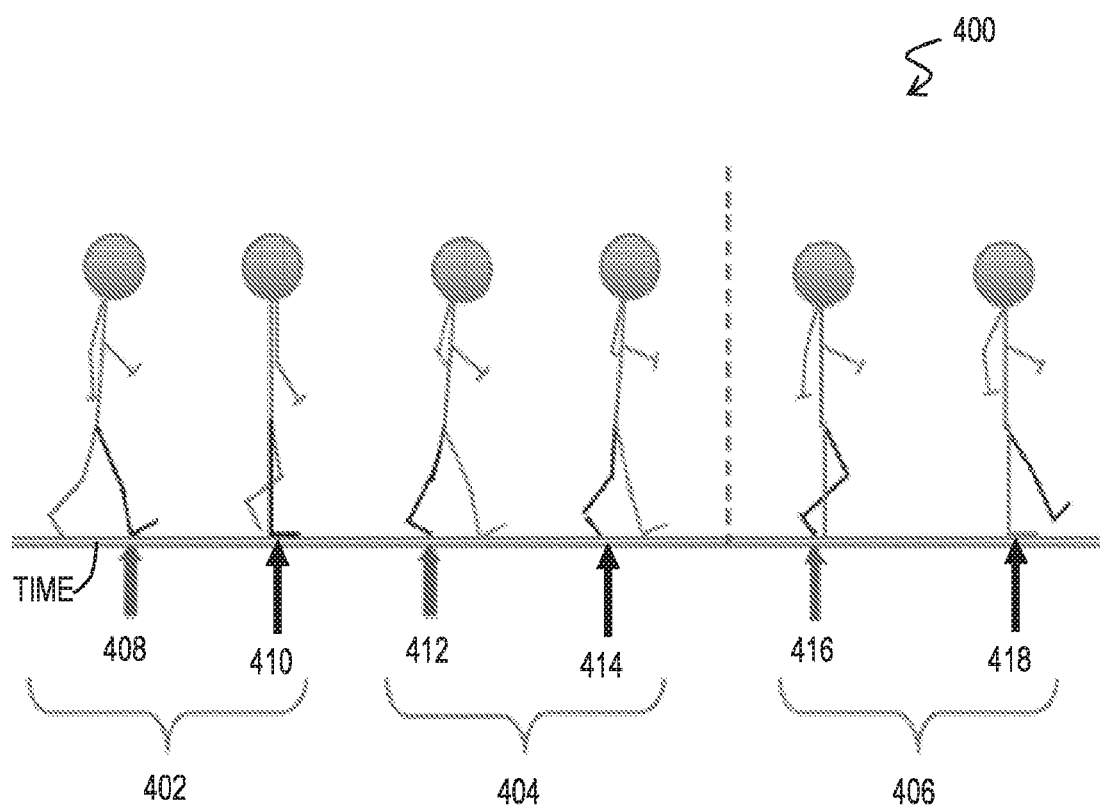
FIG. 4A is a diagram of a plurality of movement phases of a gait cycle of an ankle joint, according to an embodiment.

To perform step 201 of the method 200, a plurality of movement phases for a gait cycle 400 of the impaired ankle joint are initially determined. FIG. 4A is a diagram of a plurality of movement phases of the gait cycle 400 of the ankle joint, according to an embodiment. The gait cycle 400 begins with an early stance 402 which includes a heel strike movement phase 408 and a mid stance movement phase 410. The gait cycle 400 then proceeds to a late stance 404, which include a heel off movement phase 412, and a toe off movement phase 414. The gait cycle 400 then proceeds to a swing 406 that includes an initial swing movement phase 416 and a terminal swing movement phase 418.

Figure 4B:
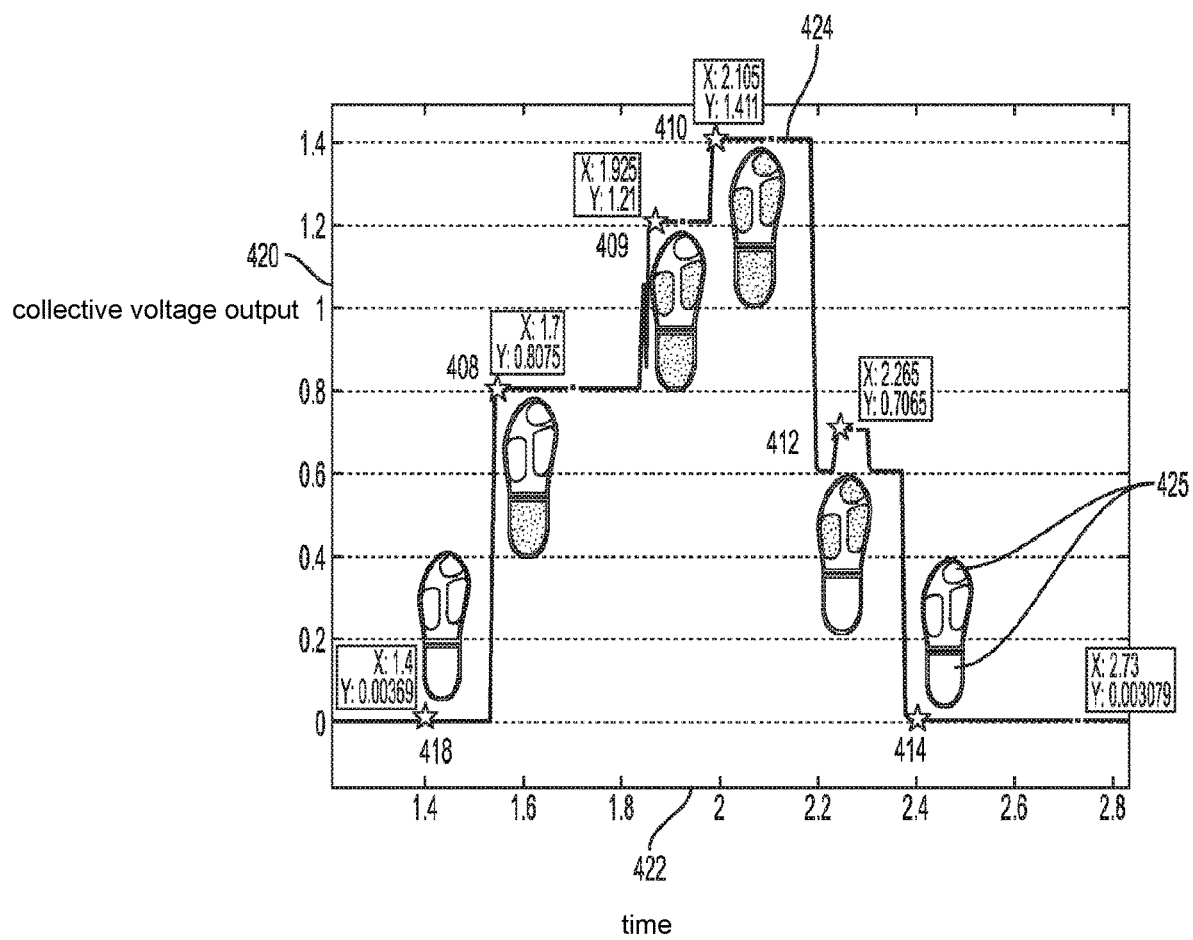
FIG. 4B is a trace of sensor state output over the plurality of movement phases of the gait cycle of FIG. 4A, according to an embodiment.

In order to determine when the subject is in each of these movement phases, FIG. 4B illustrates footswitches 425 (corresponding to subject sensors 120) that are positioned in a heel region, a toe region, a medial region and a lateral region of the shoe 302 of the anklebot 300. The footswitches 425 are connected to the drive module 150 through the controller 140 of the anklebot 300 and communicates the collective output of the footswitches 425 to the drive module 150, during each movement phase of the gait cycle 400. Each footswitch 425 is a pressure sensor, which switches to an "on" position and outputs a respective voltage signal when a threshold pressure is detected in that respective region of the shoe. Each footswitch 425 remains in an "off" position and does not output the respective voltage signal if the threshold pressure is not detected in that respective region of the shoe.

As illustrated in the FIG. 4B, a trace 424 is shown of the collective voltage output of the footswitches 425, plotted against a vertical axis 420 versus a horizontal time axis 422 that includes the plurality of movement phases of the gait cycle 400. The trace 424 begins at a minimum collective voltage output of the footswitches 425 when the subject enters the terminal swing movement phase 418 and each footswitch 425 is "off", since no region of the shoe is in contact with the ground. The trace 424 increases when the subject enters the heel strike movement phase 408, when the heel region footswitch 425 is "on" and the other footswitches 425 are "off", since only the heel region of the shoe contacts the ground. The trace 424 continues to increase when the subject enters an early stance movement phase 409 between the heel strike movement phase 408 and the mid stance movement phase 410, when the heel region footswitch 425, medial region footswitch 425 and lateral region footswitch 425 are each "on" while the toe region footswitch 425 is "off". The trace 424 increase to a maximum collective voltage output of the footswitches 425 when the subject enters the mid stance movement phase 410 and each footswitch 425 is "on" since all regions of the shoe are in contact with the ground. The trace 424 decreases when the subject enters the heel off movement phase 412, when the heel region footswitch 425 is "off" and the remaining footswitches 425 are "on", since the toe region, medial region and lateral region of the shoe are in contact with the ground. The trace 424 then decreases to the minimum collective voltage output of the footswitches 425 when the subject enters the toe off movement phase 414 and each footswitch 425 is "off", since no region of the shoe is in contact with the ground. The trace 424 continues to repeat as the gait cycle 400 is repeated by the subject.

To perform step 201 of the method 200 in the example embodiment, FIG. 5 is a flow diagram that illustrates an example of a method 500 for determining a plurality of movement phases for an ankle joint function based on footswitch 425 output, according to an embodiment. After starting, in step 501 the footswitches 425 are positioned in each region of the shoe 302 of the anklebot 300, including the toe region, the heel region, the medial region and the lateral region. The anklebot 300 is then attached to a subject, such as a normal subject without an impaired ankle joint. The normal subject then walks unassisted for a predetermined time period, such as 1 minute. In step 503, the drive module 150 of the controller 140 receives the collective footswitch 425 output from the footswitches 425 as the subject walks through multiple gait cycles 400. In step 505, the module 150 analyzes the collective footswitch 425 output over time, and compares the footswitch 425 output with predetermined voltage thresholds for each movement phase that are stored in a memory of the module 150. Based on this analysis, in step 505, the module 150 determines the movement phases of the gait cycle 300 for the ankle joint, based on the collective footswitch 425 output.

Figure 6:
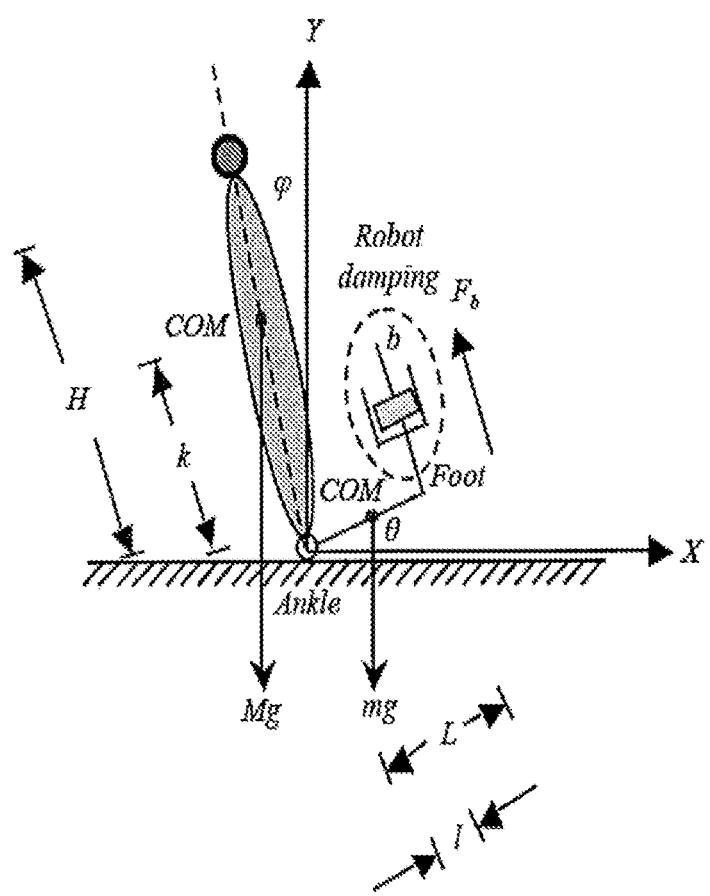
FIG. 6 is a diagram that illustrates dimensions of a body and a foot wearing the anklebot.

Additionally, to perform step 201 of the method in the example embodiment, a movement model for each movement phase is determined and programmed into the module 150 of the controller 140. FIG. 6 illustrates the components of the model, according to an embodiment. The movement model for a deficit moving between the heel strike movement phase 408 and the mid stance movement phase 410 (also known as "foot slap") is parameterized by a minimum damping parameter $b_{min}$ defined by Equation 1 below. Given a human with body height H and mass M, and assuming zero volitional torque, $b_{min}$ is the minimum damping parameter to constrain the peak ankle angular speed $V_{HS}$ to be less than some desired (e.g., normative) value $V_m$ to lessen impact forces at landing.

$$b_{min} \geq \frac{\alpha g M H \phi}{V_m - V_{HS}} \quad (1)$$

where $\alpha$ is k/H; k is a distance between a body center of mass and the ankle (in meters, m); H is the height of the body (meters, m); M is the mass of the body (in kilograms, kg); g is the acceleration due to gravity (9.81 ms$^{-2}$); $\phi$ is the angle between the subject's body part (e.g. 191) and a vertical direction (radians, rad); $V_m$ is the desired maximum angular velocity of the foot during the heel strike movement phase 408 (degrees per second, °/sec) and $V_{HS}$ is the measured maximum angular velocity of the foot during the heel strike movement phase 408 (degrees per second, °/sec). The minimum damping parameter $b_{min}$ is inversely proportional to the desired upper-bound on the peak angular speed $V_m$ i.e., the higher the damping, the less is the peak angular speed (and hence the impact force), and vice versa.

Figure 7:
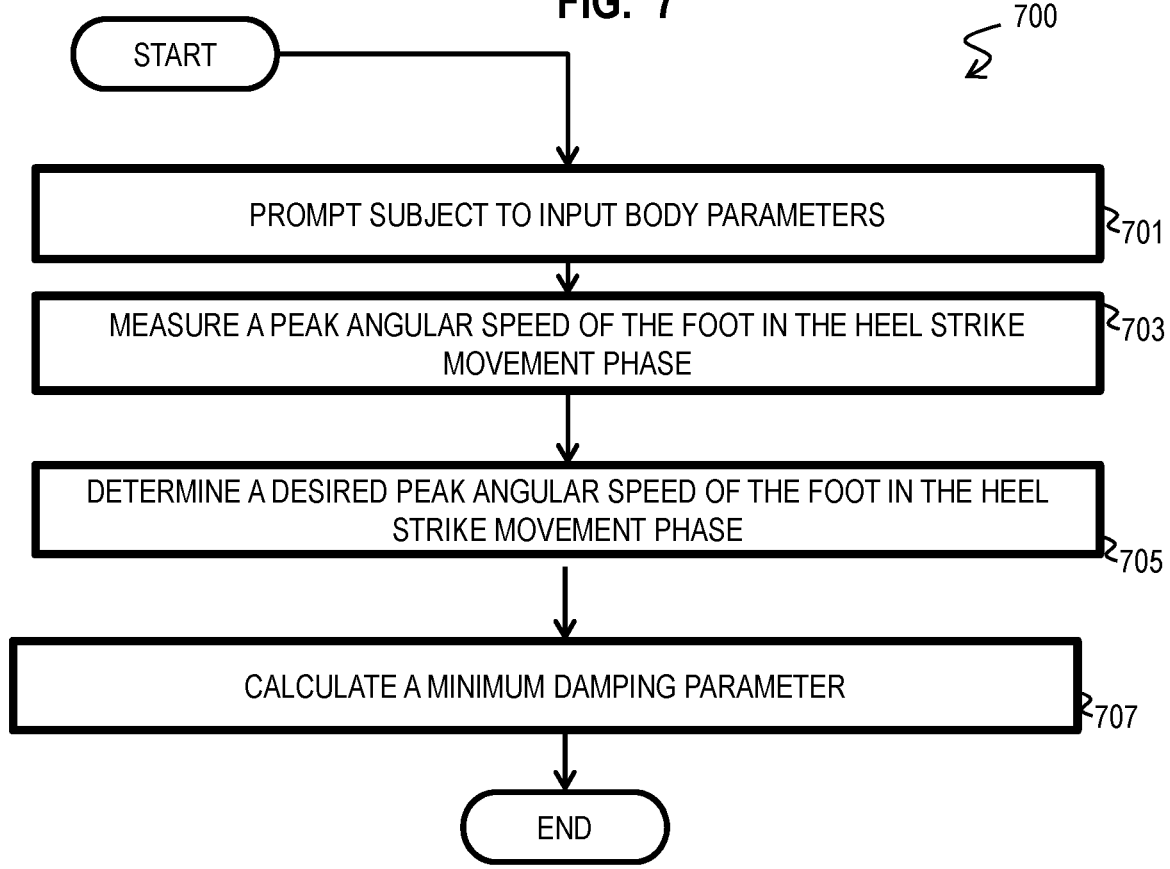
FIG. 7 is a flow diagram that illustrates an example of a method for determining a movement model for a heel strike movement phase of a gait cycle, according to an embodiment.

FIG. 7 is a flow diagram that illustrates an example of a method 700 for determining a movement model between the heel strike movement phase 408 and the mid stance movement phase 410 of the gait cycle 400 of an ankle joint function, according to an embodiment. In step 701, the module 150 prompts the subject to input the body parameters of Equation 1, including the distance k, the height H, the mass M, and the angle $\phi$. In step 703, the module 150 measures a peak angular speed of the foot of the subject between the movement phase 408, 410, during an unassisted walking cycle of an impaired subject, as discussed below. In step 705, the module 150 determines a desired peak angular speed of the foot between the movement phase 408, 410. In an example embodiment, the desired peak angular speed may be fixed for all subjects at a typical normative value of an age-matched non-impaired subject. In one example, the desired peak angular speed is 200 degrees per second. In an example embodiment, the desired peak angular speed is determined, based on measuring a peak angular speed of a non-paretic foot during an unassisted walking cycle of an impaired subject.

In step 707, the module 150 uses Equation 1 to calculate the minimum damping parameter $b_{min}$. The steps of the method 700 are programmed into the module 150 and upon determining that an impaired subject suffers from the "foot slap" deficit between the heel strike movement phase 408 and the mid stance movement phase 410, the module 150 commences the steps of the method 700, to determine the minimum damping parameter, which is used to parameterize the torque for movement between the heel strike movement phase 408 and the mid stance movement phase 410.

Figure 8:
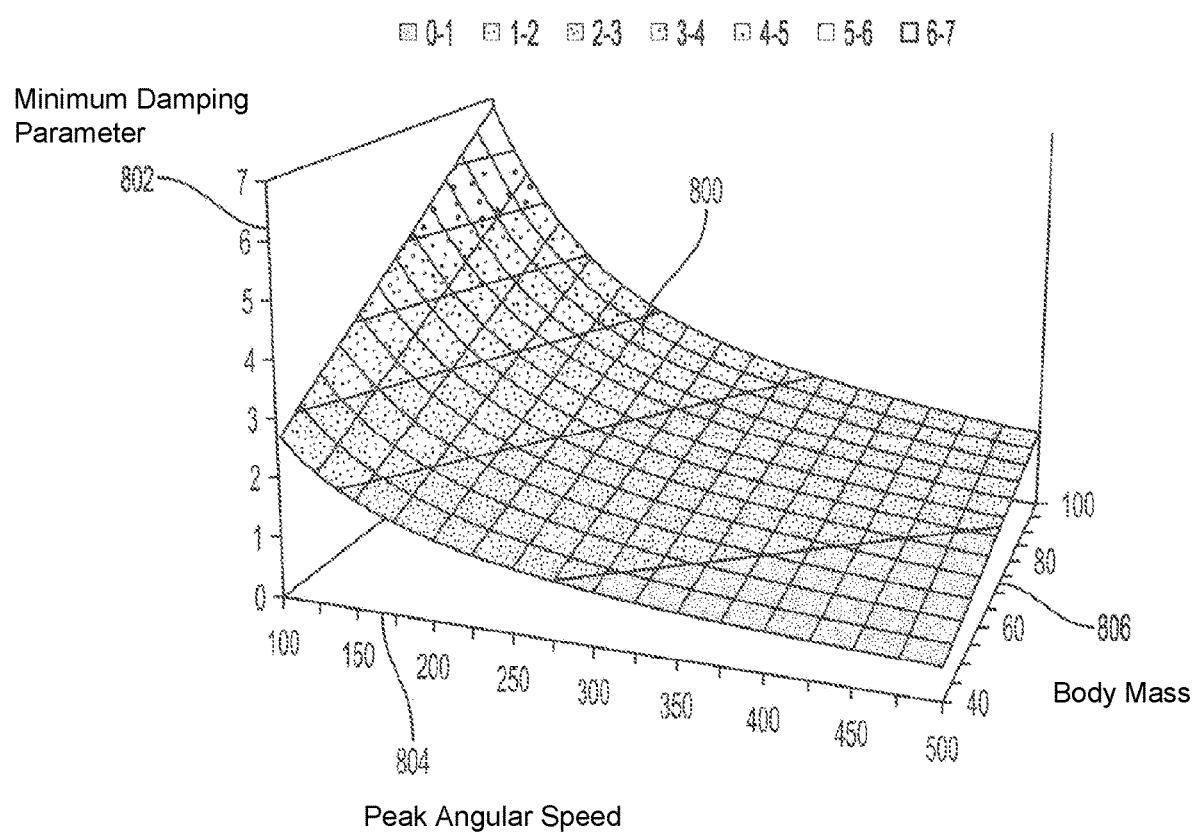
FIG. 8 is a graph that illustrates an example of a minimum damping parameter trace based on a body mass and a desired peak angular speed of a subject, according to an embodiment.

FIG. 8 illustrates an example of a minimum damping parameter surface 800 determined based on a body mass M and a desired peak angular speed $V_m$ of a subject. The surface 800 value is given by a vertical axis 802 of values of the minimum damping parameter $b_{min}$. The desired peak angular speed $V_m$ value is given by a position relative to a first horizontal axis 804 while the body mass M value is given by a position relative to a second horizontal axis 806. Instead of using Equation 1 to calculate the minimum damping parameter $b_{min}$, a digital version of FIG. 8 provides an optional "quick look up" surface 800, to determine the minimum damping parameter $b_{min}$ based on a known mass M and desired angular speed $V_m$. Either Equation 1 or the surface 800 of FIG. 8 provides the minimum damping parameter $b_{min}$ used for the measured maximum angular velocity at the heel strike movement phase ($v_{HS}$) to be equal to or lower than desired maximum angular velocity at heel strike movement phase ($V_m$).

Figure 9:
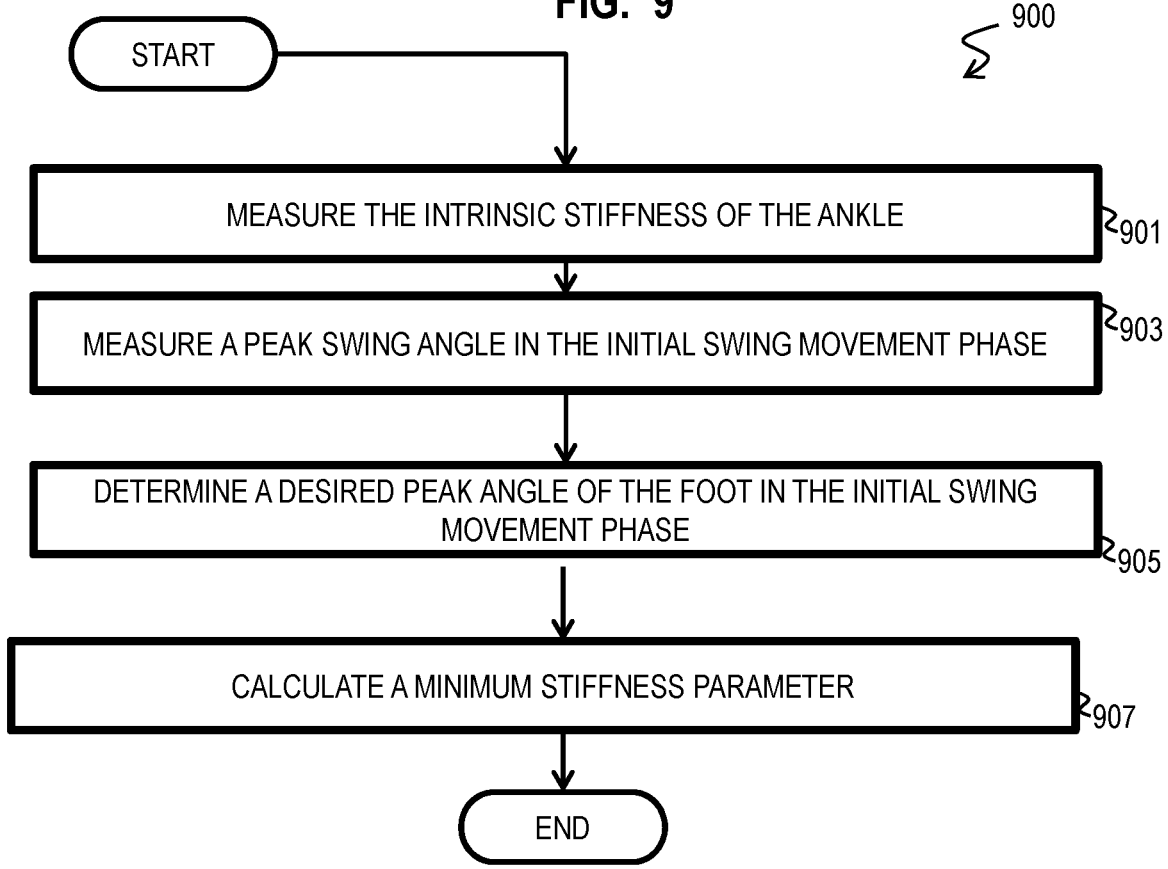
FIG. 9 is a flow diagram that illustrates an example of a method for determining a movement model for an initial swing movement phase of a gait cycle, according to an embodiment.

Additionally, to perform step 201 of the method in the example embodiment, a movement model for movement between the initial swing movement phase 416 and the terminal swing movement phase 418 (also known as "drop foot") is parameterized by a minimum stiffness parameter $K_{min}$ provided by Equation 2 below. The minimum stiffness parameter $K_{min}$ is used to ensure that the peak ankle angle during the swing movement phase 416 attains a desired value.

$$K_{min} = -\frac{\gamma K_h}{1 - \gamma} \qquad (2)$$

where γ is $\Theta_{max}/\Theta_d$ (between 0 and 1); $\Theta_{max}$ is an actual peak angle measured during the initial and terminal swing movement phases 416, 418 (in degrees, °); $\Theta_d$ is a desired peak angle measured during the initial and terminal swing movement phases 416, 418 (in degrees, °) and $K_h$ is an intrinsic stiffness of the ankle (in Newton meters per radian, Nm/rad). FIG. 6 illustrates the angle Θ measured between the ground and the foot of the subject during the initial and terminal swing movement phases 416, 418. FIG. 9 is a flow diagram that illustrates an example of a method 900 for determining a movement model for movement between the initial swing movement phase 416 and the terminal swing movement phase 418 of the gait cycle 400, according to an embodiment.

In step 901, the module 150 determines the intrinsic stiffness $K_h$ of the ankle. In an example embodiment, while the subject is in a seated position, the module 150 transmits signals to the motor 314 to tilt the foot at a constant angular velocity, such as 5 degrees per second. In an example embodiment, each tilt begins and ends at the neutral position and moves in increments of 5 degrees (e.g. ±5 degrees from neutral, ±10 degrees from neutral, etc.). For each angular displacement of the foot, a responsive torque is measured, using current or voltage data sent from the motor 314 to the controller 140. The ratio of the measured torque (in units of Nm) to angular displacement (in radians) from neutral yields an estimate of the intrinsic ankle stiffness (Nm/rad). In one example embodiment, the intrinsic ankle stiffness estimates were thus obtained in each direction of movement within a DOF by fitting the pair-wise steady-state torque and angle data using least-squares linear regression.

In step 903, the module 150 measures a peak swing angle of the foot of the subject during the initial and terminal swing phases 416, 418, during an unassisted walking cycle of an impaired subject, as discussed below.

In step 905, the module 150 determines a desired peak angle of the foot in the initial and terminal swing phases 416, 418. In an example embodiment, the desired peak angle may be fixed for all subjects at a typical normative value of an age-matched non-impaired subject. In one example, the desired peak angle is in a range of 10-12 degrees. In an example embodiment, the desired peak angle is determined, based on measuring a peak angle of a non-paretic foot during an unassisted walking cycle of an impaired subject.

In step 907, the module 150 uses Equation 2 to calculate the minimum stiffness parameter $K_{min}$. The steps of the method 900 are programmed into the module 150 and upon determining that an impaired subject suffers from the "drop foot" deficit between the initial and terminal swing phases 416, 418, the module 150 commences the steps of the method 900, to determine the minimum stiffness parameter, which is used to parameterize the torque for movement between the initial and terminal swing phases 416, 418.

Figure 10A:
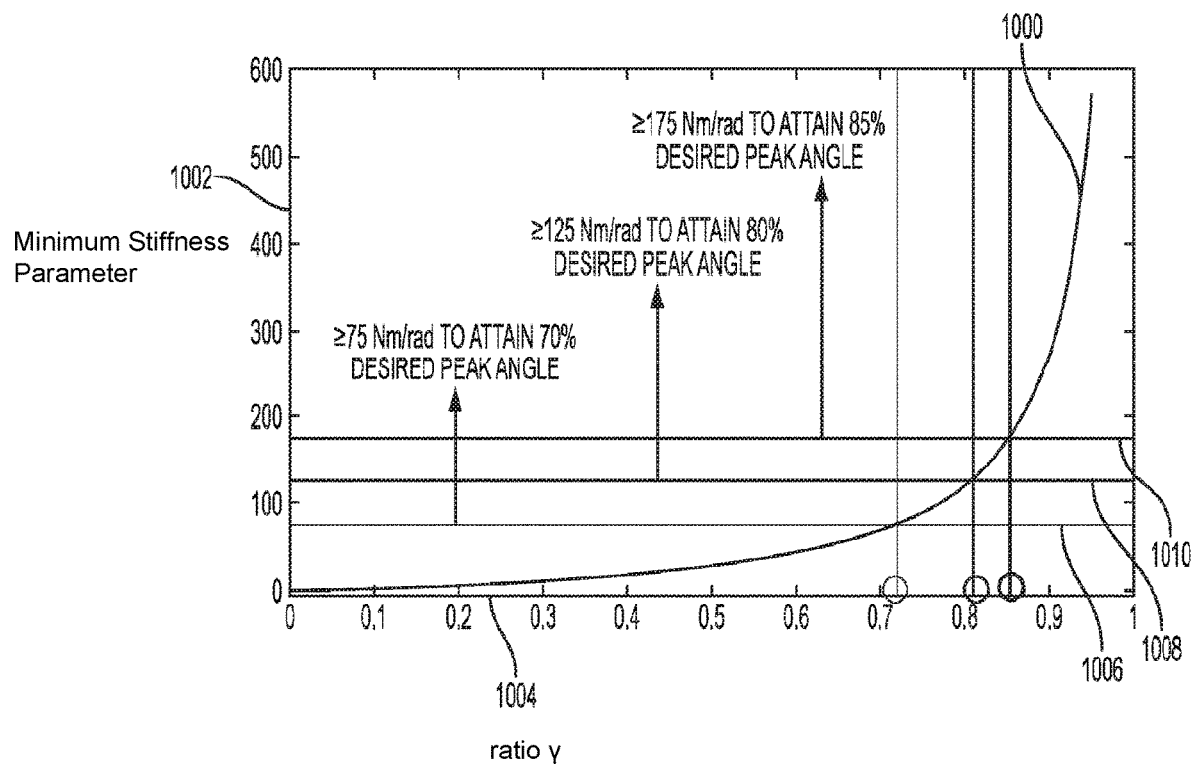
FIG. 10A is a graph that illustrates an example of a minimum stiffness parameter trace based on a ratio of an actual peak swing angle of a subject to a desired peak swing angle, according to an embodiment.

FIG. 10A is a graph that illustrates an example of a minimum stiffness parameter trace 1000 based on the ratio γ of the actual peak swing angle $\Theta_{max}$ of a subject to the desired peak swing angle $\Theta_d$, according to an embodiment. The trace 1000 has a value based on a position relative to a vertical axis 1002 of values of the minimum stiffness parameter $K_{min}$. The ratio γ is indicated by a horizontal axis 1004. The trace 1000 is formed using Equation 2 based on an intrinsic stiffness $K_h$ of 30 Nm/rad. Instead of using Equation 2 to calculate the minimum stiffness parameter $K_{min}$, a digital table of the trace 1000 in FIG. 10A provides an optional "quick look up" table, to determine the minimum stiffness parameter $K_{min}$ based on a known ratio γ of the actual peak swing angle $\Theta_{max}$ of a subject to the desired peak swing angle $\Theta_d$. Both Equation 2 and the trace 1000 of FIG. 10A provide the minimum stiffness parameter $K_{min}$ needed for the actual peak angle $\Theta_{max}$ to be a desired ratio γ of the desired peak swing angle $\Theta_d$. FIG. 10A illustrates a plurality of vertical intercept lines 1006, 1008, 1010 that intersect the vertical axis 1002 at respective values of $K_{min}$ that achieve a particular ratio γ of the actual peak swing angle $\Theta_{max}$ of a subject to the desired peak swing angle $\Theta_d$. For example, the vertical intercept line 1008 intersects the vertical axis 1002 at a $K_{min}$ value of 125 Nm/rad, indicating the value of $K_{min}$ required to achieve a ratio γ of 0.8.

Figure 10B:
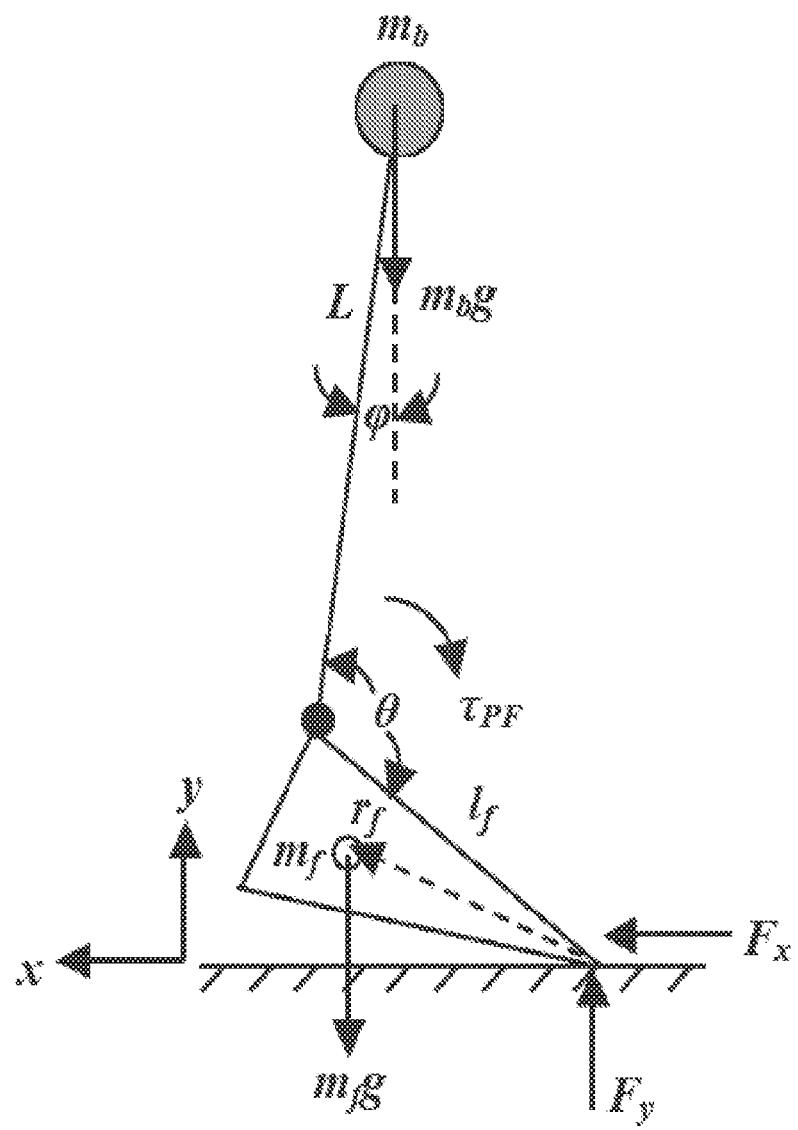
FIG. 10B is a diagram that illustrates example dimensions of a body and a foot wearing the anklebot, according to an embodiment.

Additionally, to perform step 201 of the method in the example embodiment, a movement model for movement between the heel off movement phase 412 and the toe off movement phase 414 (also known as "push off") uses a different minimum stiffness parameter than the minimum stiffness parameter of Equation 2 for the movement model between the initial and terminal swing movement phases 416, 418. FIG. 10B is a diagram that illustrates dimensions of a body and a foot wearing the anklebot. In an example embodiment, a body with length L and center of mass $m_b$ is depicted, that forms an angle with a vertical direction. The foot has a length $l_f$ and center of mass $m_f$ that forms an angle Θ with respect to the body. $\tau_{PF}$ is a robot applied torque about the ankle between the initial and terminal swing movement phases 416, 418. $F_x$ and $F_y$ are the respective anterior-posterior (AP) and ground reaction forces (GRF) imposed on the ankle between a time instant $t_{HO}$, when a heel region of the foot comes off the ground and $t_{TO}$, when a toe region of the foot comes off the ground. In an example embodiment, $t_{HO}$ is determined when the output from the footswitch 425 in the heel region changes from high to low (or on to off). In another example embodiment, $t_{TO}$ is determined when the output from the footswitch 425 in the toe region changes high to low (or on to off). The minimum stiffness parameter, $K_{min2}$, for the movement model between the heel off movement phase 412 and toe off movement phase 414 is determined by:

$$K_{min2}(\theta^*_{PF}\Delta T_{LS} - I_\theta) - I_a(\Delta\dot{\theta} + \Delta\dot{\varphi}) + b\Delta\theta_{LS} + m_f g c_a \Delta T_{LS} \geq \quad (3)$$
$$l_f\left(P_d + \int_{t_{HO}}^{t_{TO}^-} |F_y| dt\right).$$

where $\theta^*_{PF}$ is a peak swing angle of the foot with respect to the body between $t_{HO}$ and $t_{TO}$ in units of degrees (deg); $\Delta T_{LS}$ is the time duration between $t_{HO}$ and $t_{TO}$ in units of seconds (sec); $I_\theta$ is an area under θ(t) between $t_{HO}$ and $t_{TO}$ in units of degrees-seconds; $I_a$ is the moment of inertia of the foot about the ankle (in units of kilograms meters$^2$); $\Delta\dot{\theta}$ is a difference in ankle angular velocity between $t_{HO}$ and $t_{TO}$ in units of degrees per second (deg/sec); $\Delta\dot{\varphi}$ is a difference in body angular velocity between $t_{HO}$ and $t_{TO}$ in units of degrees per second (deg/sec); b is the robot damping parameter in units of Nms/rad; $\Delta\theta_{LS}$ is an ankle angular displacement between $t_{HO}$ and $t_{TO}$ in units of degrees (deg); $m_f$ is the mass of the foot in units of kilograms (kg); g is acceleration due to gravity; $c_a$ is a foot center of mass horizontal position relative to the ankle in units of meters (m); if is the length of the foot in units of meters (m); $P_d$ is the desired impulse on the ankle in the x direction between $t_{HO}$ and $t_{TO}$ based on $F_x$ in units of Newton*seconds; $F_y$ is the GRF on the ankle between $t_{HO}$ and $t_{TO}$. In contrast to the minimum stiffness parameter $K_{min}$ of Equation 2 for the movement model between the initial swing movement phase 416 and the terminal swing movement phase 418, the minimum stiffness parameter $K_{min2\_}$ based on Equation 3 corresponds to the minimum stiffness needed to attain a desired (i.e. normative) value of anterior-posterior (AP) impulse (that is, the definite time integral of force where integral time limits are the heel off movement phase 412 for the lower bound and the toe off movement phase 414 for the upper bound) during late stance 404 of the gait cycle 400. Hence, the minimum stiffness parameter $K_{min2}$ is used to calculate supplemental plantar-flexion assistance (i.e. torque) needed to attain desired AP propulsive impulse during late stance 404, as many stroke survivors have weak push-off propulsion owing to diminished mechanical power generation by the ankle musculature (in this case, the plantar-flexors—the two primary plantar-flexors are Gastrocnemius and Soleus muscles).

To perform step 203 of the method 200, the anklebot 300 is worn by a normal subject who walks for a predetermined amount of time, such as 1 minute, and moves the ankle joint through the plurality of movement phases while the anklebot 300 does not apply torque. As the normal subject moves the ankle through the plurality of movement phases, the footswitches 425 transmit the voltage 420 signal to the module 150, so the module 150 can determine the movement phase that correspond to the voltage 420 signal. Additionally, as the normal subject moves the ankle joint through the plurality of movement phases, the sensor 313 measures the position or angle of the foot based on the movement of the ankle during each movement phase and transmits this position or ankle data to the drive module 150 through the controller 140. In some embodiments, the torque sensor (e.g. motor 314) measures the torque applied by the movement of the ankle during each movement phase and transmits this torque data to the module 150 through the controller 140.

Figure 11:
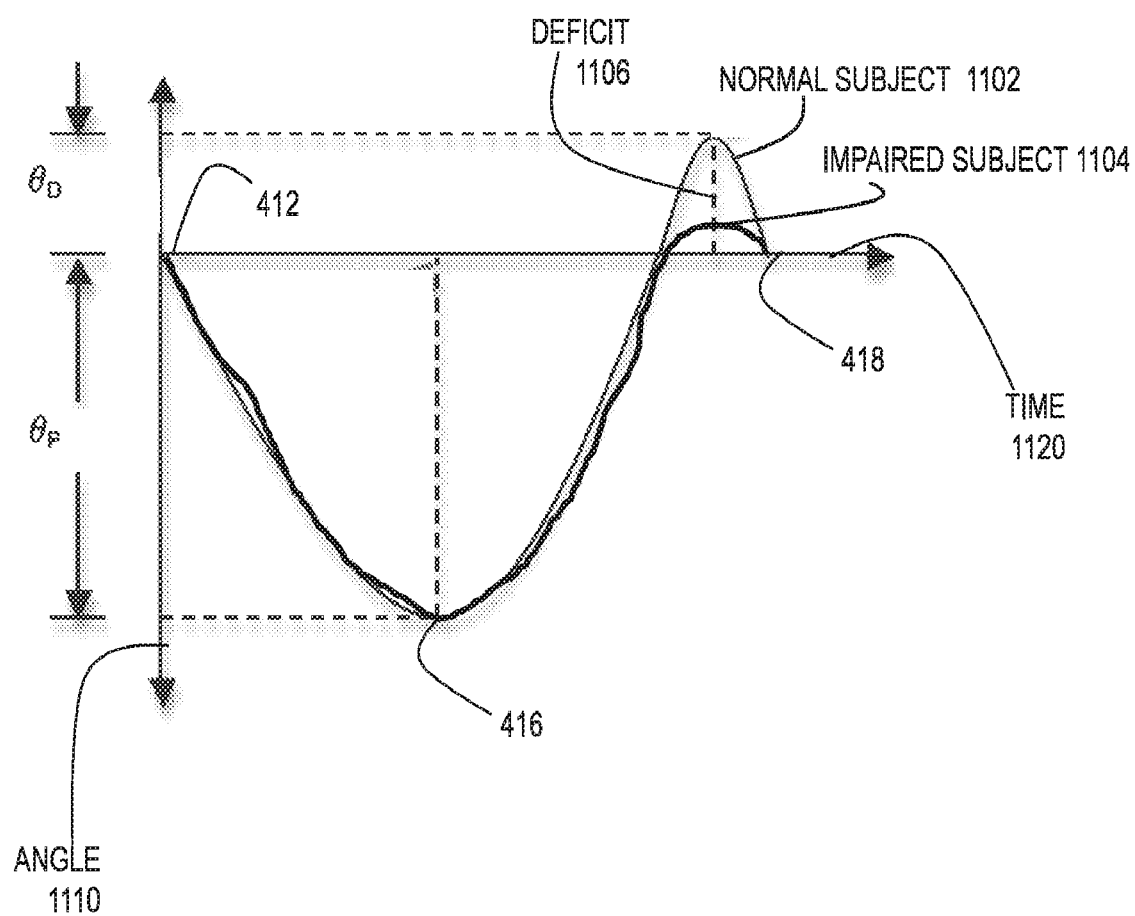
FIG. 11 is a graph that illustrates an example of an angle trace for a normal and impaired subject over a plurality of movement phases, according to an embodiment.

As a result of the angle data or position data received by the module 150, FIG. 11 illustrates an example of an angle trace 1102, 1104 for a normal and impaired subject over a plurality of movement phases, according to an embodiment. The horizontal axis 1120 indicates time, in relative units within a movement phase sequence. The left vertical axis 1110 indicates the measured angle of the foot relative to the ground. The angle trace 1102 is measured by the sensor 313 (or by the motor 314 using torque data), as the normal subject moves the ankle joint through the plurality of movement phases, and plotted relative to the vertical axis 1110. The module 150 uses the received footswitch 425 data versus time to determine the angle trace 1102 within each movement phase of the gait cycle 400. As illustrated in FIG. 11, when the normal subject enters the heel off movement phase 412, the angle trace 1102 is approximately zero since the foot is approximately flat on the ground. As the subject moves from the heel off movement phase 412, the angle trace 1102 decreases as the angle of the foot becomes increasingly negative and reaches a negative peak angle $\Theta_p$ at the initial swing movement phase 416. As the subject moves from the initial swing movement phase 416, the angle trace 1102 increases and reaches the maximum peak angle $\Theta_d$ (also called the desired peak angle) before the subject reaches the terminal swing movement phase 418. The angle trace 1102 is stored in a memory of the module 150. In an embodiment, instead of the angle trace 1102, in step 203 a torque trace is formed based on the torque data provided to the module 150 from the torque sensor (e.g. motor 314) during the unassisted walk of the normal subject and the torque trace is stored in the memory of the module 150.

To perform step 205 of the method 200, the anklebot 300 is worn by an impaired subject who walks for a predetermined amount of time, such as 1 minute, and moves the ankle joint through the plurality of movement phases while the anklebot 300 does not apply torque. As the impaired subject moves the ankle through the plurality of movement phases, the footswitches 425 transmit the voltage 420 signal to the module 150, so the module 150 can determine the movement phase that correspond to the voltage 420 signal. Additionally, as the impaired subject moves the ankle joint through the plurality of movement phases, the sensor 313 measures the position or angle of the foot based on the movement of the ankle during each movement phase and transmits this position or ankle data to the controller 140. In some embodiments, the torque sensor (e.g. motor 314) measures the torque applied by the movement of the ankle during each movement phase and transmits this torque data to the controller 140. Additionally, in an embodiment, during step 205, the peak angular speed (e.g. step 703 of method 700) is measured during the heel strike movement phase 408 and the peak swing angle $\Theta_{max}$ (e.g. step 903 of method 900) is measured during the initial swing movement phase 416. As a result of the angle data or position data received by the module 150, FIG. 11 illustrates an angle trace 1104 that is measured by the sensor 313 (or by the motor 314 using torque data), as the impaired subject moves the ankle joint through the plurality of movement phases, and plotted relative to the vertical axis 1110. In an embodiment, in step 205, instead of the angle trace 1104, a torque trace is formed based on the torque data provided to the module 150 from the torque sensor (e.g. motor 314) during the unassisted walk of the impaired subject and the torque trace is stored in the memory of the module 150.

In an embodiment, the anklebot 300 includes footswitches 425 positioned in both shoes 302 worn by the subject and the module 150 receives a collective voltage 420 signal from each set of footswitches 425 from each shoe 302. During step 205, if the angle deficit of the impaired subject is extensive, the module 150 may be unable to determine the movement phase that corresponds to the voltage signal 420 received from the footswitches 425 in the shoe 302 of the impaired foot. The module 150 is then configured to determine the movement phase of the impaired foot, based on the voltage signal 420 received from the footswitches 425 in the shoe 302 of the non-impaired foot. The module 150 first determines the movement phase of the non-impaired foot, based on the voltage signal 420 received from the footswitches 425 in the shoe 302 of the non-impaired foot, and then converts the movement phase of the non-impaired foot to a movement phase of the impaired foot. A memory of the module 150 stores the conversion relationship between a movement phase of the non-impaired foot and a movement phase of the impaired foot during the gait cycle 400. For example, when the non-impaired foot is in the mid stance movement phase 410, the impaired foot is in the heel off movement phase 412. In this embodiment, the module 150 uses the footswitch 425 signals from the non-impaired foot during the use of the anklebot 300, to determine the current movement phase and the timing and magnitude of the torque applied to the foot.

Figure 12:
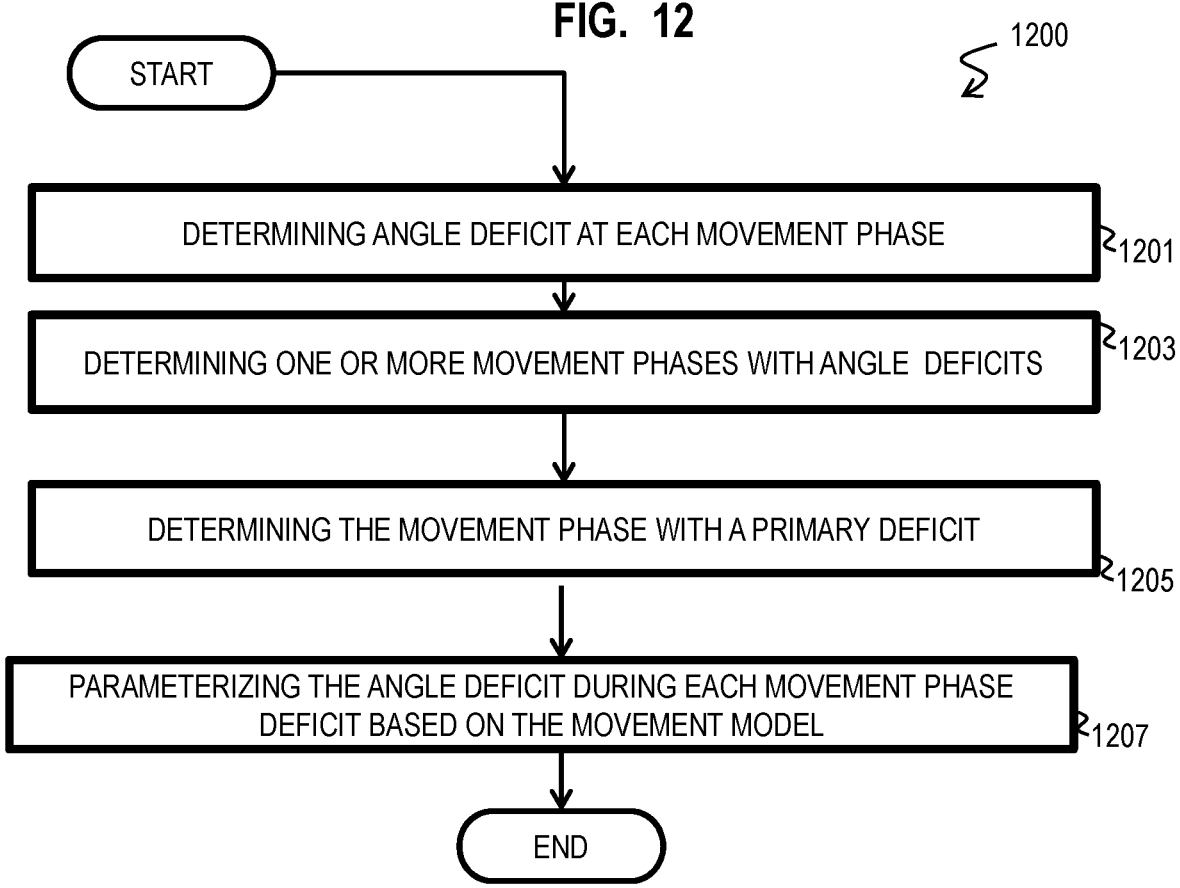
FIG. 12 is a flow diagram that illustrates an example of a method for determining a deficit angle for each movement phase of a gait cycle, according to an embodiment.

To perform step 207 of the method 200, FIG. 12 is a flow diagram that illustrates an example of a method 1200 for determining the deficit angle 1106 for each movement phase of the gait cycle 400, according to an embodiment. In step 1201, the module 150 determines the deficit angle 1106 for each movement phase, based on the respective angle traces 1102, 1104. In one embodiment, the module 150 determines the deficit angle 1106 for each movement phase by computing a difference between the angle trace 1102 for the normal subject and the angle trace 1104 for the impaired subject, for each movement phase.

In step 1203, the module 150 determines a magnitude and a polarity of the deficit angle 1106 between the angle traces 1102, 1104 for each movement phase. The module 150 then identifies the movement phase for each deficit angle 1106, based on the magnitude and polarity of the deficit angle 1106. In an example embodiment, the module 150 identifies an angle deficit 1106 between the heel off movement phase 412 and the toe off movement phase 414, based the polarity of the deficit angle 1106 being positive and the magnitude of the deficit angle 1106 being greater than a first minimum threshold. In an example embodiment, the module 150 identifies an angle deficit 1106 between the initial swing movement phase 416 and the terminal swing movement phase 418, based the polarity of the deficit angle 1106 being positive and the magnitude of the deficit angle 1106 being greater than a second minimum threshold that is less than the first minimum threshold. In an example embodiment, the first minimum threshold is in a range of 5-10° and the second minimum threshold is in a range of 0-5°. In an example embodiment, the module 150 identifies an angle deficit 1106 between the heel strike movement phase 408 and the mid stance movement phase 410, based on the polarity of the deficit angle 1106 being negative and a magnitude of the maximum angular velocity ($v_{HS}$) being greater than a threshold velocity. In an example embodiment, the threshold velocity is in a range of 45-55°/sec. In an example embodiment, the module 150 does not identify an angle deficit 1106 during a movement phase where the magnitude of the deficit angle 1106 is zero or less than a minimum threshold.

As illustrated in FIG. 11, the module 150 determines that the polarity of the deficit angle 1106 is positive (e.g. angle trace 1102 is greater than angle trace 1104) and that the magnitude of the deficit angle 1106 is greater than the second minimum threshold. Thus, the module 150 identifies the angle deficit 1106 as between the initial and terminal swing movement phases 416, 418. Additionally, as illustrated in FIG. 11, the module 150 determines that the magnitude of the deficit angle 1106 is zero between the heel off movement phase 412 and the initial swing movement phase 416 and thus the module 150 does not identify an angle deficit between the heel off movement phase 412 and the initial swing movement phase 416.

In step 1205, the module 150 determines the movement phase with a primary angle deficit 1106 that has the largest magnitude of the identified angle deficits 1106 in step 1203. In an example embodiment, in step 1203 the module 150 determined that the angle deficits 1106 are 5 degrees, 6 degrees and 7 degrees during respective movement phases A, B and C. In step 1205, the module 150 determines that movement phase C is the primary angle deficit 1106, with the largest magnitude of 7 degrees. In one embodiment, the module 150 is configured to only cause the controller to transmit a torque signal to the motor 314 during the movement phase of the primary angle deficit 1106 identified in step 1205 until the magnitude of the angle deficit 1106 in the movement phase of the primary angle deficit is reduced by a predetermined amount.

Figure 13:
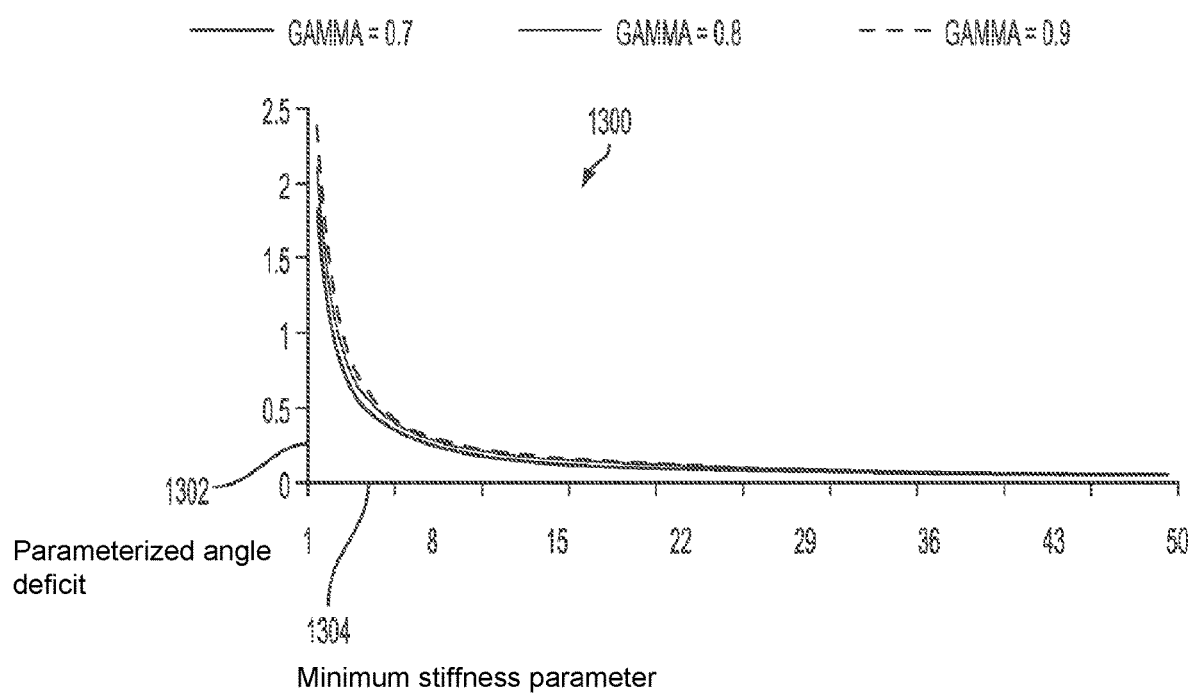
FIG. 13 is a graph that illustrates an example of a parameterized deficit angle trace based on a minimum stiffness parameter, according to an embodiment.

In step 1207, the module 150 parameterizes the angle deficit 1106 during each movement phase identified in step 1203, based on the movement models for each movement phase. In an example embodiment, for an angle deficit 1106 between the initial and terminal swing phases 416, 418, in step 1207, the module 150 uses the minimum stiffness parameter $K_{min}$ calculated using Equation 2 in step 907 in the method 900 or determined using the "look-up" trace 1000 of FIG. 10A to parameterize the deficit angle 1106. Equation 2 may be re-written as Equation 4:

$$\Delta = \frac{\theta_d K_h \gamma}{K_{min}} \quad (4)$$

where Δ is the parameterized angle deficit 906, based on the minimum stiffness parameter $K_{min}$. Equation 4 of the movement model between the initial and terminal swing phases 416, 418 explicitly links the parameterized deficit angle Δ to the minimum stiffness parameter $K_{min}$. For a chosen value of γ, the parameterized deficit angle Δ is inversely proportional to the minimum stiffness parameter $K_{min}$. FIG. 13 is a graph that illustrates an example of a parameterized deficit angle trace 1300 based on the minimum stiffness parameter $K_{min}$, according to an embodiment. The deficit angle trace 1300 is measured against a vertical axis 1302 of values of the parameterized angle deficit Δ and is plotted against a horizontal axis 1304 of values of the minimum stiffness parameter $K_{min}$. As illustrated in FIG. 13, a respective trace 1300 is provided for various values of the ratio γ, such as 0.7, 0.8 and 0.9. Thus, step 1207 for the movement phase between the initial and terminal swing phases 416, 418 involves determining the minimum stiffness parameter $K_{min}$ and then determining the parameterized angle deficit Δ either using Equation 4 or using the "look up" table of digital data based on trace 1300. The parameterized angle deficit determined in step 1207 is used to initialize the anklebot 300, from which the stiffness value K is varied over time, based on actual performance and historical time of recovery.

To perform 1207 for the movement model between the heel strike movement phase 408 and the mid stance movement phase 410, after identifying the angle deficit 1106 between the movement phases 408, 410, the controller 140 determines a deficit torque Δτ that is a difference between a desired torque $\tau_d$ and a measured torque ti between the heel strike movement phases 408 and the mid stance movement phase 410. In an embodiment, the desired torque $\tau_d$ of a normal subject and a measured torque ti of an impaired subject between the heel strike movement phases 408 and the mid stance movement phase 410 were measured by the torque sensor (e.g. motor 314) during steps 203, 205 and stored in a memory of the module 150. During step 1207, the module 150 uses the minimum damping parameter $b_{min}$ calculated using Equation 1 in step 707 in the method 700 or determined using the "look-up" trace 800 of FIG. 8 to parameterize the deficit torque Δτ between the movement phases 408, 410. Equation 1 may be re-written as Equation 5.

$$\Delta\tau \leq v_{min}(V_m - v_{HS}) + \tau_d - C \quad (5)$$

where Δτ is the parameterized deficit torque between the movement phases 408, 410, $\tau_d$ is the desired torque between the movement phases 408, 410 and C is αgMHφ from Equation 1. The movement model between the movement phases 408, 410 explicitly links deficit torque Δτ to the minimum damping parameter $b_{min}$. For a chosen value of $V_m$, the deficit torque Δτ is directly proportional to the minimum damping parameter $b_{min}$.

FIG. 14 is a graph that illustrates an example of a parameterized deficit torque trace 1400 based on the minimum damping parameter $b_{min}$, according to an embodiment The deficit torque trace 1400 is measured against a vertical axis 1402 of values of the parameterized torque deficit Δτ and is plotted against a horizontal axis 1404 of values of the minimum damping parameter $b_{min}$. As illustrated in FIG. 14, a respective trace 1400 is provided for various values of the maximum angular velocity ($v_{HS}$), such as 100°/sec, 200°/sec and 300°/sec. Thus, step 1207 for the movement phase between the heel strike movement phase 408 and mid stance movement phase 410 involves determining the minimum damping parameter $b_{min}$ and then determining the parameterized torque deficit Δτ either using Equation 5 or using a digital "look up" table based on trace 1400. The parameterized torque deficit determined in step 1207 is used to initialize the anklebot 300, from which to the damping value b is varied over time, based on actual performance and historical time of recovery.

FIG. 15 is a block diagram that illustrates an example drive module 1500 for providing deficit-adjusted adaptive assistance during a plurality of movement phases of an impaired ankle joint, according to an embodiment. Drive module 1500 is a specific embodiment of module 150, but does not include human ankle 1510. During operation of the module 1500, the impaired subject wears the anklebot 300 and moves the subject's ankle 1510 through a plurality of movement phases. The human ankle 1510 imparts pressure on one or more of the footswitches 425, which transmit the collective voltage 420 output to the module 1500. Based on the method 500 of FIG. 5, the module 1500 predetermined the movement phase of the gait cycle 300 that corresponds to each collective footswitch output, and this predetermined relationship is depicted in table 1502. Based on the collective voltage 420 output of the footswitches 425, the module 1500 determines the current movement phase of the gait cycle 300. As discussed above, the module 1500 stored the ankle trace 1102 of a normal subject and the angle trace 1104 of the impaired subject in a memory, which is depicted as reference module 1506 in FIG. 15. As the subject walks through each movement phase, the module 1500 retrieves the stored angle trace 1102 value, angle trace 1104 value and the deficit angle 1106 corresponding to the current movement phase from the reference module 1506.

In an example embodiment, instead of the angle trace values 1102, 1104 and the angle deficit 1106, the module 1500 may retrieve torque trace values of the normal subject and impaired subject and the deficit torque of the current movement phase that are stored in the memory of the module 1500.

To perform step 209 of the method 200, the adaptive timing for the anklebot-applied torque 1514 is determined for a current movement phase by the module 150 based on the current voltage 420 output of the footswitches 425. In the example embodiment of FIG. 15, the module 1500 determined that the current voltage 420 output of the footswitches 425 indicates that the current movement phase is the heel off movement phase 412. The module 1500 uses the reference module 1506 to determine whether the magnitude of the angle deficit 1106 in the current movement phase is zero (or less than a minimum threshold). If the module 1500 determines that the magnitude of the angle deficit 906 is zero (or less than the minimum threshold) in the current movement phase, the module 1500 does not transmit an applied torque signal to the motor 314 during the current movement phase. If the module 1500 determines that the magnitude of the angle deficit 1106 in the current movement phase is greater than zero (or the minimum threshold), the module 1500 transmits an applied torque signal to the anklebot 300, e.g., motor 314, during the current movement phase.

To perform step 211, the adaptive magnitude for the anklebot-applied torque 1514 is determined for a current movement phase by the module 1500. The adaptive magnitude of the anklebot-applied torque 1514 is provided by Equation 6

$$\tau_R = K\Delta + B\frac{d}{dt}(\Delta) \quad (6)$$

where $\tau_R$ is the anklebot applied torque 1514; K is the stiffness setting of the controller 140; A is the angle deficit 1106 for the current movement phase and B is a damping setting of the controller 140. The stiffness setting K and damping setting B of the controller 140 are initially set to the respective minimum stiffness setting $K_{min}$ and the minimum damping setting $b_{min}$ determined from Equations 1 and 2. As discussed in step 1207, the polarity and magnitude of the angle deficit 1106 are predetermined for each movement phase and stored in a memory of the module 1500 (e.g. reference module 1506). Since the polarity of the angle deficit 1106 is positive between the initial and terminal swing phases 416, 418 and between the heel off movement phase 412 and the toe off movement phase 414, the resulting anklebot applied torque 1514 from Equation 6 is assistive during these movement phases. Since the polarity of the angle deficit 1106 is negative between the heel strike movement phase 408 and the mid stance movement phase 410, the resulting anklebot applied torque 1514 from Equation 6 is restorative during these movement phases.

In an example embodiment, the module 1500 uses the method 900 of FIG. 9 and Equation 2 to determine the minimum stiffness parameter $K_{min}$, which is then used to parameterize the adaptive magnitude of the applied torque 1514 during the current movement phase between the initial and terminal swing phases 416, 418. By substituting the angle deficit $\Delta = \Theta_d - \Theta$ into Equation 6, the following Equation 7 is obtained:

$$\tau_R = K(\theta_d - \theta) + \frac{d}{dt}(\theta_d - \theta) \tag{7}$$

where $\Theta_d$ is the desired angle and $\Theta$ is the measured angle between the initial and terminal swing phases 416, 418. Since $\Theta_d$ is the desired peak angle between the initial and terminal swing phases 416, 418 (see FIG. 11), the time derivative of $\Theta_d$ is zero. The time derivative of the measured angle $\Theta$ between the initial and terminal swing phases 416, 418 is $v_\Theta$, the measured ankle angular velocity. Additionally, to attain the desired ratio $\gamma$ of the desired peak angle $\Theta_d$, K is set to the value of the minimum stiffness parameter $K_{min}$ from Equation 2. Based on these assumptions, Equation 7 becomes:

$$\tau_R = K_{min}\Delta + Bv_\Theta = \Theta_d K_h \gamma + Bv_\Theta \tag{8}$$

where B is a damping held constant (in a range of 0.5-1.0 Nms/rad) When the current movement phase is between the initial and terminal swing phases 416, 418, and the controller 140 identifies an angle deficit during this current movement phase (i.e. step 1203), the module 1500 parameterizes the anklebot imparted torque 1514 based on Equation 8.

In an example embodiment, the module 1500 uses the method 700 of FIG. 7 and Equation 1 to determine the minimum damping parameter $b_{min}$, which is then used to parameterize the adaptive magnitude of the applied torque 1514 during a current movement phase between the heel strike movement phase 408 and mid stance movement phase 410. In contrast to the movement model between the swing phases 416, 418, the torques predicted by the model between the heel strike movement phase 408 and the mid stance movement phase 410 is by nature, "springy" restorative (for shock absorption of abnormally high impact forces due to "foot slap" resulting from foot drop deficit). The mode of application of the model between the movement phases 408, 410 initially sets the controller 140 stiffness K to 0 Nm/rad, and thus it follows from Equation 6 that the torque is given by Equation 9.

$$\tau_R = B\frac{d}{dt}(\Delta) \tag{9}$$

In Equation 8, the damping setting B of the module 1500 is set to $b_{min}$ and using Equation 1, so Equation 10 is obtained:

$$\tau_R = b_{min}v_\Theta = \frac{\alpha g M H \phi}{V_m - v_{HS}} \tag{10}$$

When the current movement phase is between the heel strike movement phase 408 and the mid stance movement phase 410, and the module 1500 identifies an angle deficit during this current movement phase (e.g., in step 1203), the module parameterizes the anklebot imparted torque 1514 based on Equation 10.

To perform step 213, the adaptive magnitude of the anklebot applied torque 1514, as determined by one or more of Equations 6 through 10, is applied by the motor 314 on the shoe 302 for the current movement phase, based on the adaptive timing for the current movement phase. During step 213, the module 1500 transmits the adaptive magnitude data for the applied torque 1514 for the current movement phase to the motor 314, based on the adaptive timing for the current movement phase from step 209. Upon receiving the adaptive magnitude data from the module 1500, the motor 314 imparts the applied torque with the adaptive magnitude on the shoe 302 during the current movement phase. Steps 215, 217, 219, 221 are performed in the example embodiment of the anklebot in a similar manner as in the method 200 discussed above.

Figure 16:
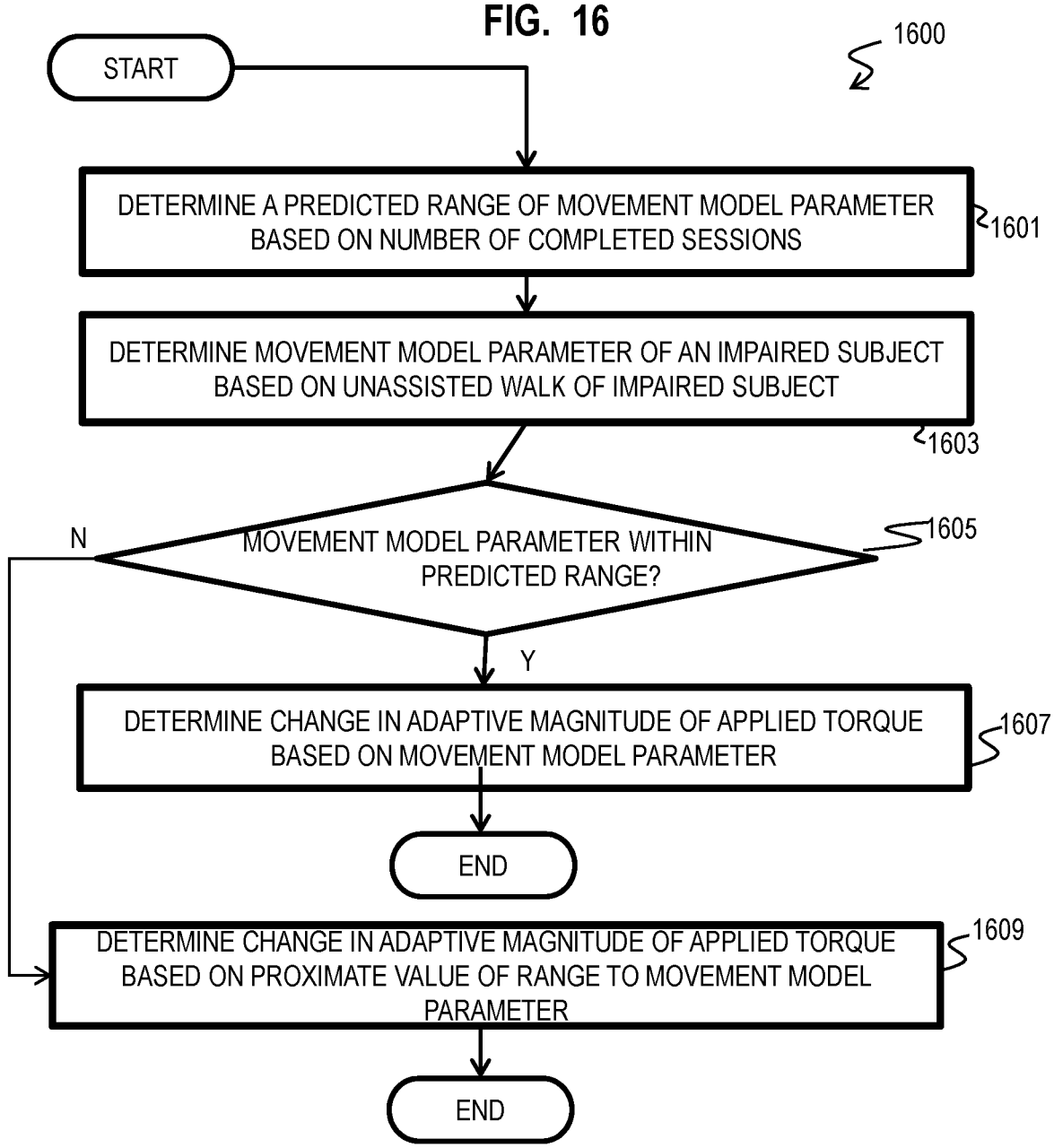
FIG. 16 is a flow diagram that illustrates an example of a method for predicting a change in the adaptive magnitude of the applied torque in each movement phase.

In step 223, a prediction in the change of the adaptive magnitude of the applied torque 1114 is made by the module 150 for each movement phase. FIG. 16 is a flow diagram that illustrates an example of a method 1600 for predicting a change in the adaptive magnitude of the applied torque 1514 in each movement phase.

In step 1601, the module 150 determines a predicted range of the movement model parameter for each movement phase, based on the number of completed sessions. In an example embodiment, the predicted range of the minimum stiffness parameter $K_{min}$ is 125-150 Nm/rad for the first 3 sessions, 150-200 Nm/rad for the next 6 sessions and 75-125 Nm/rad thereafter. In an example embodiment, the predicted range of the minimum damping parameter $b_{min}$ is 3-4 Nms/rad for the first 3 sessions, 2-3 Nms/rad for the next 6 sessions and 1.1.5 Nms/rad thereafter.

In step 1603, the impaired subject wears the anklebot 300 during an unassisted walking session, and the module 150 receives torque data from the motor 314, position or angle data from the sensor 313 and voltage 420 output data from the footswitches 425. Based on the methods 700, 900, the module 150 uses the measured position data to recalculate the movement model parameter for each movement phase.

In step 1605, the module 150 compares the recalculated movement model parameter from step 1603 with the predicted range of the movement model parameter from step 1601. In an example embodiment, if the module 150 recalculates a minimum stiffness parameter $K_{min}$ of 145 Nm/rad in step 1603 and determines a predicted range of 125-150 Nm/rad in step 1601, the module 150 determines that the recalculated movement model parameter is within the predicted range and proceeds to step 1607. If the module 150 determines that the recalculated movement model parameter is not within the predicted range, the method 1600 proceeds to step 1609.

In step 1607, the module 150 uses the recalculated movement model parameter in step 1603 to determine a change in the adaptive magnitude of the applied torque 1514, as in step 211.

In step 1609, the module 150 uses a proximate value of the predicted range to the movement model parameter to determine a change in the adaptive magnitude of the applied torque 1514. In an example embodiment, if the module 150 calculates a minimum stiffness parameter $K_{min}$ of 170 Nm/rad in step 1603 and determines a predicted range of 125-150 Nm/rad in step 1601, then in step 1609 the module 150 determines that the maximum range value of 150 Nm/rad is the most proximate value to the recalculated minimum stiffness parameter of 170 Nm/rad and thus the module 150 uses the proximate value of 150 Nm/rad parameter to determine a change in the adaptive magnitude of the applied torque 1514, as in step 211.

Figure 17:
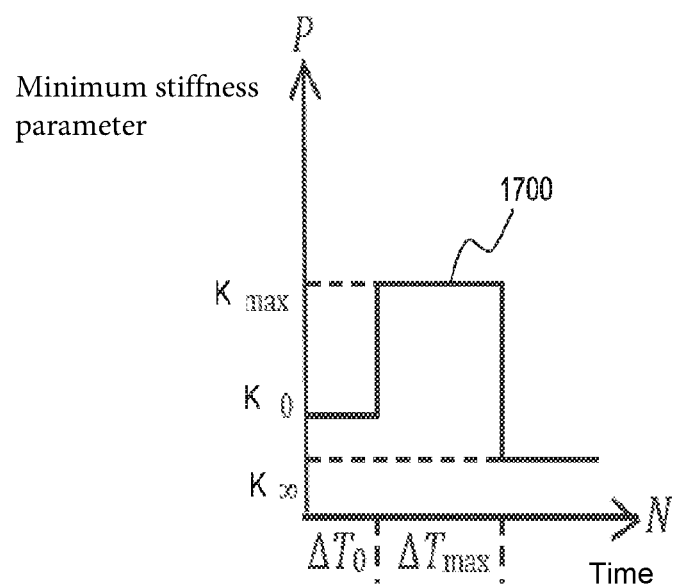
FIG. 17 is an example of a trace of the minimum stiffness parameter over a number of physical therapy sessions, according to an embodiment.

FIG. 17 is a graph that illustrates an example of a trace 1700 of the minimum stiffness parameter $K_{min}$ over a number of physical therapy sessions, according to an embodiment. In the embodiment of FIG. 17, during a first period of physical therapy $\Delta T_0$, which includes 1-3 sessions, the minimum stiffness parameter $K_{min}$ is adjusted to a value $K_0$ within the range of 125-150 Nm/rad. During a second period of physical therapy $\Delta T_{max}$, which includes 6-9 sessions, the minimum stiffness parameter $K_{min}$ is adjusted to a value $K_{max}$ within the range of 150-200 Nm/rad. During a third period of physical therapy beyond $\Delta T_{max}$ the minimum stiffness parameter is adjusted to a value $K_\infty$ within a range of 75-125 Nm/rad. Step 223 of the method 200 may be performed by choosing the value within the range of the movement model parameter, and subsequently determining the change in the adaptive magnitude of the applied torque in each movement phase using one or more of Equations 6 through 10, based on this change in the movement model parameter.

Figure 18:
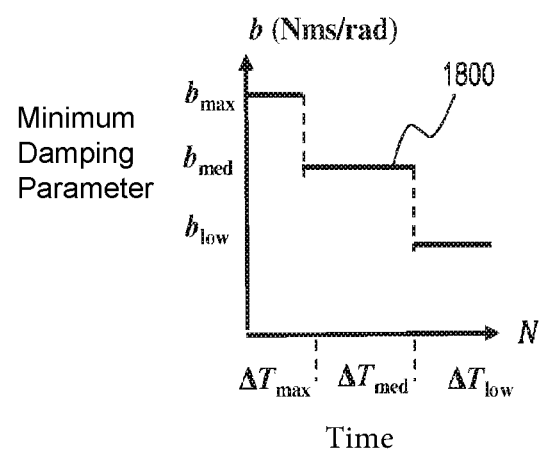
FIG. 18 is a graph that illustrates an example of a trace of the minimum damping parameter over a number of physical therapy sessions, according to an embodiment.

FIG. 18 is a graph that illustrates an example of a trace 1800 of the minimum damping parameter $b_{min}$ over a number of physical therapy sessions, according to an embodiment. In the embodiment of FIG. 18, during a first period of physical therapy $\Delta T_{max}$, which includes 1-3 sessions, the minimum damping parameter $b_{min}$ is adjusted to a maximum value $b_{max}$ within the range of 3-4 Nms/rad. During a second period of physical therapy $\Delta T_{med}$, which includes 6-9 sessions, the minimum damping parameter $b_{min}$ is adjusted to a value $b_{med}$ within the range of 2-3 Nms/rad. During a third period of physical therapy beyond $\Delta T_{low}$ the minimum damping parameter is adjusted to a value $b_{low}$ within a range of 1-1.5 Nms/rad. Step 223 of the method 200 may be performed by choosing the value within the range of the movement model parameter, and subsequently determining the change in the adaptive magnitude of the applied torque in each movement phase, using one or more of Equations 6 through 10, based on this change in the movement model parameter.

B. Amputation Prostheses

In an embodiment, the invention is utilized in the context of amputation prostheses that are designed to replace lost limbs in a patient, and partial amputations of the distal lower extremity that help the patient: a) recover mobility performance capacities that involve the ankle and multi-segmental motor control (whole body); and, b) improve sensory-motor function of gait and balance not only when worn, but with training in appropriate cases, produce benefits that carry over when the device is not being worn to increase the quantity and safety of mobility activities of daily living. In particular, leg prostheses provide mechanical support, shock absorption, balance, and forward propulsion. An example embodiment of the invention provides functionality regarding assistance and resistance during movement phases of leg prostheses, including the swing phase (in the air) to enhance proper orientation prior to landing, and during the stance phase to control the ground forces in a cooperative and healthier manner in collaboration with the user. In an example embodiment, battery-powered motorized amputation prostheses that utilize the adaptive timing and adaptive magnitude for adaptive assistance can be utilized to advance the field of active amputation prostheses, this is particularly true for partial distal foot amputees that now utilize primarily static devices that offer limited or no dynamic control of kinetic (forces) and kinematic (direction) forces that control the quality and safety of movement.

In an example embodiment, adaptive timing of resistance to lower limb amputation prostheses helps manage collisions between the foot and the ground, enabling the conduct of mobility activities in a fashion that improves the pattern of ground reaction forces to reduce damaging impacts at the affected lower extremity that can directly damage tissues, and produce pain, orthopedic, and movement abnormalities up the kinematic chain (forces that are conducted up the shank to the knee, hip, and whole body). In an example embodiment, adaptive magnitude of resistance as informed by landing model can also be used in leg prostheses to dampen and control the direction and magnitude of the forces of landing, controlling the timing of landing to improve balance and duration of the foot strike to enhance stability and symmetry, while reducing damaging tissue forces and improving whole body (multi-segmental) function.

C. Training Healthy Joints

Motion of the ankle from side-to-side (inversion-eversion, or the frontal plane henceforth referred to as the IE plane) is mechanically independent of motion of the ankle up-and-down (sagittal plane, or PD plane), and measured the passive stiffness (that is, the spring-like property under external positional perturbations) separately in the PD and the IE planes, with the first-ever measurement in the IE plane. Moreover, when moved passively, the ankle is weakest (that is, mechanically most compliant) when turning inward, stronger when tilting from side-to side (that is, mechanically less compliant, or stiffer), and strongest when simply moving up-and-down (that is mechanically least compliant, or stiffest), demonstrating highly anisotropic (that is, direction dependent) multi-planar, passive mechanical impedance.

The methods used to measure multi-planar, passive mechanical impedance of the ankle joint, are equally generalizable to estimating the mechanical impedance for other lower limb joints such as the more proximal knee and hip joints. In an example embodiment of the invention, these teachings can be applied to train healthy people to exercise their ankles in specific ways that strengthen them (in the context of human performance augmentation) and help reduce future injuries. In this example embodiment, the invention is used for human performance augmentation of lower limb joints including but not limited to the ankle. This example embodiment may also lead to "smart" mechanical footwear that can either provide scaled and timed resistance in lateral (e.g. side-to-side) foot motion for mechanical stability, while providing timed assistance for up-down motion; or, provide no assistance but is designed using smart materials (such as smart material alloys, or SMAs) that have variable impedances in different planes (that is, PD plane versus IE plane) and in different directions within a plane (such as, dorsiflexion versus plantar-flexion) leading to highly ergonomic and efficient passive properties during engagement of the ankle (or other proximal lower limb joints whose mechanical impedances are estimated using methods in the aforementioned citations).

D. Regulating Foot Pressure and Ground Reaction Forces in Diabetic Neuropathy

In some embodiments, one or more steps of the above methods are used in the context of regulating foot pressure and ground reaction forces in diabetic neuropathy. Approximately 9.3% of people in the United States and perhaps 5% globally have Type 2 Diabetes Mellitus (T2DM), including 26% of individuals over 65 years of age; with a major rise in this condition anticipated based on known global aging and obesity trends. A substantial portion of these people will develop peripheral neuropathy, ultimately 100% across the course of the disease, which leads to reduced sensation, particularly in the toes and feet. This is followed by intrinsic foot muscle wasting and secondary orthopedic problems consisting of hammer toes, Charcot Joints, lateral toe deviations, and thinning of the metatarsal pads. All of these conditions, combined with the insensate foot, lead to foot ulcers, which produce a 50% five-year survival, as they are only treatable with "static orthotics" to better distribute the foot pressure forces.

In one example embodiment, the movement model of the invention employed between the heel strike movement phase 408 and the mid stance movement phase 410 of the gait cycle 400 (i.e. "foot slap") may be utilized to impart restorative torque on the subject's shoe and thus enable precise timing of impulse, or ground reaction forces that are seen by the toes and foot, thereby enabling a dynamic real time control to reduce the pressures that are known to lead to foot ulcers, to exacerbate ulcers, associated infections including osteomyelitis, and ultimately, amputations. Additionally, the progression elements of the movement model between the movement phases 408, 410 afforded by the invention produce motor learning during ambulatory conditions, which affords inroads in the fields of podiatry and orthotics for the care of diabetic neuropathy, and other neuropathies such as peripheral arterial occlusive disease, chronic inflammatory de-myelinative neuropathy, axonal neuropathy, heavy metal, vasculitic, immune-mediated, traumatic, post-chemotherapy, and other neuropathies that involve either sensory, motor, or sensorimotor involvement, yielding new therapies to improve the quality and quantity of foot-strikes, to reduce foot and joint damage, prevent ulcers, improve function, and ultimately prevent disability and amputations.

E. Motor Learning to Improve Outcomes for Podiatry, Orthopedics, and Prosthetics Some embodiments are utilized in the context of motor learning to improve outcomes for podiatry, orthopedics, and prosthetics, as well as for individuals that have mixed or complex conditions, such as any neurological, spinal cord, or peripheral nerve process or injury superimposed, causing, or contributing to conditions that fall under the domain of podiatry, orthopedics, and related prosthetics. Selected postoperative care conditions in podiatry and orthopedics could optimize outcomes if ground reaction forces (impulse) and the behavior of the foot and ankle in the swing and stance phase were controlled for safety and for progressive motor learning of more safe and stable dynamic walking and balance patterns were optimized in the immediate postoperative rehabilitative recovery period, and across the sub-acute and chronic phases of care; particularly the latter periods when repetitive maladaptive use patterns cause tissue and functional declines over-time, which are not adequately addressed by passive devices that lack adaptive control and step-by-step real-time modulation of involved foot and leg forces. These embodiments offer the control systems a deficit-adjusted and step-by-step capacity to modulate dynamic gait and balance. In an embodiment, the inbuilt sensors also provide simultaneous recording capacity and informatics to inform clients, caregivers, and therapists with a quantitative reporting in order to avoid pitfalls, and modify health promoting physical activity behaviors. In the field of prosthetics, the ground reaction forces (impulse) are conducted up the prosthetic or residual limb shank, and over many years, repetitive use and pounding can cause pain, damage to tissue at the stump that has limited vascularity leading to injury and/or infections, and secondary joint injuries above the stump.

The movement model of embodiments employed between the heel strike movement phase 408 and the mid stance movement phase 410 of the gait cycle 400 (i.e. "foot slap") may be utilized to produce a bio-inspired walking pattern utilizing the adaptive controller in a deficit severity adjusted manner, with machine learning to adapt the underlying prosthetic device to cushion the stump can be used to improve outcomes in prosthetics. An embodiment utilizes intrinsic measurements of the device during these identified gait cycle phases to estimate and model the forces, providing a grading system for the clients, caregivers, therapists, and biomechanists to utilize to provide feedback and optimize care. For those with polytrauma, and subsequent tibialis anterior (e.g. swing phase deficit) or peroneal nerve damage with foot eversion and/or dorsi-flexion weakness (foot-drop), or stance phase deficit due to lumbar 5-sacral 1 or sciatic trunk or incomplete tract injury, the modular deficit severity adjustable units can be adapted to serve as a task-oriented functional mobility therapeutic tool to extend the clients dynamic cooperative control, and the therapists capabilities to tune the mobility profile toward a safer pattern with respect to impact forces and stability, pain reduction, and overall measured level of physical activity to maintain health and functional independence. This would enable precise mathematical modeling for optimization of progression that would serve as a cumulative repository for assisting and informing the recovery of future similar polytrauma and orthopedic or mixed neurological-orthopedic cases. The latter embodiment includes capacity to upgrade the systems control to optimize recovery and functionality in an ongoing fashion, either by re-programming, on-line refinement, or consultation, contingent on the nature and complexity of the condition under treatment.

F. Robot-Assisted Mobility Activities of Daily Life

In some embodiments, one or more steps of the above methods are used in the context of providing robotic assistance to facilitate safe conduct of activities of daily life (ADLs) that use lower limb mobility. While walking is a high priority ADL and fundamental to regaining functional mobility, there are other home-community ADLs (such as stair climb, step on/off curb, step over obstacles etc.) that engage and rely on properly timed and adequate foot control for success and safety. An aspect fundamental to mobility ADLs in diverse real-world settings is that they consist of a finite set of key movements in order to customize multi-segmental motor control to the task(s), and avoid obstacles for safety. As such, integral sub-tasks may be thought of as mobility "primitives" (such as, step height clearance during a stair ascend task), which include navigating through a changing environment in ways that feature rapid, in-course dynamic adjustments. Successful (safe) and efficient conduct of any mobility ADL thus features successful and efficient conduct of each sub-task or primitive inherent to the task. Individuals with lower limb including ankle deficits resulting from stroke, or other neurologic conditions, or due to aging, are often challenged in performing one or more mobility primitives inherent to a particular mobility ADL.

In an example embodiment, the anklebot 300 of FIG. 3 can be used to assist a subject with ankle deficits while performing an ADL. FIG. 28A is the anklebot 300 of FIG. 3 used by a subject 2890 during a staircase 2810 ascend, where the subject 2890 has the "drop foot" deficit between swing phases 416, 418 (see FIG. 4A). The staircase 2810 includes a plurality of steps 2812, 2814, 2816, with a step height 2818 between the steps 2812, 2814, 2816. During the swing phases 416, 418 of the gait cycle 400 (see FIG. 4A) as the subject 2890 steps from step 2812 to step 2814, the anklebot 300 imparts the robot-applied torque based on the adaptive magnitude determined in step 211, which provides a sufficient amount of torque in the PD plane so that the subject 2890 can clear the step height 2818 between steps 2812, 2814. As the subject 2890 steps from step 2814 to step 2816, the anklebot 300 imparts the same robot-applied torque, to provide the sufficient amount of torque in the PD plane so that the subject 2890 can clear the step height 2818 between steps 2814, 2816.

FIG. 28B is a pair of graphs that illustrate an example of angle traces 2850, 2852 of the subject 2890 in FIG. 28A measured in the plantar-dorsiflexion plane during assisted and unassisted modes of the anklebot 300. The traces 2850, 2852 include a horizontal time axis 2856 and a vertical axis 2854 of the measured angle in the plantar-dorsiflexion plane. The angle trace 2850 during the assisted mode of the anklebot 300 shows that the measured angle reaches a positive peak swing angle 2851 (approximately +15 degrees) enabling the subject 2890 to clear the height 2818 between step 2812 and step 2814, and enabling the subject to clear the height 2818 between step 2814 and step 2816. The angle trace 2852 during the unassisted mode of the anklebot 300 shows that the measured angle reaches a negative peak swing angle 2853 (approximately −15 degrees) resulting in the subject 2890 not being able to clear the height 2818 between step 2812 and step 2814, and in the subject 2890 not being able to clear the height 2818 between the step 2814 and step 2816.

Although FIGS. 28A-28B discuss the anklebot 300 used to assist a subject 2890 during a staircase ascend, the anklebot 300 may be used to assist a subject during any ADL, including stepping on a curb or during stepping over an obstacles, all of which are common mobility ADLs that feature adequate and properly timed foot-surface clearance for safety and success. Such, and other similar embodiments that therapeutically or functionally target a common mobility primitive (foot-surface clearance) will expand the ecological settings for utilization of actuated assistive technologies including robotics, to safely and efficiently re-train/re-engineer basic mobility ADLs for those with mobility disabilities at one (such as, the ankle) or more (such, as the ankle plus knee) lower limb joints resulting from stroke and other neurologic, and due to aging. In the aforementioned example embodiment, this would consist of dorsiflexion assist during swing 408 phase to successfully execute staircase ascend, stepping over and onto a curb, and stepping over obstacles amongst others. Since the deficit-adjusted approach works by controlling sub-tasks during one or more movement phases by delivering precisely timed robotic-applied torque(s) at events corresponding to those sub-tasks, each with its unique functional needs, its generic control system and versatility lends itself toward extension and applicability to controlling a diverse range of mobility primitives that in turn, are utilized by a wide range of mobility ADLs.

G. One Dimensional Exo-Skeletal Ankle Joint

Figure 21A:
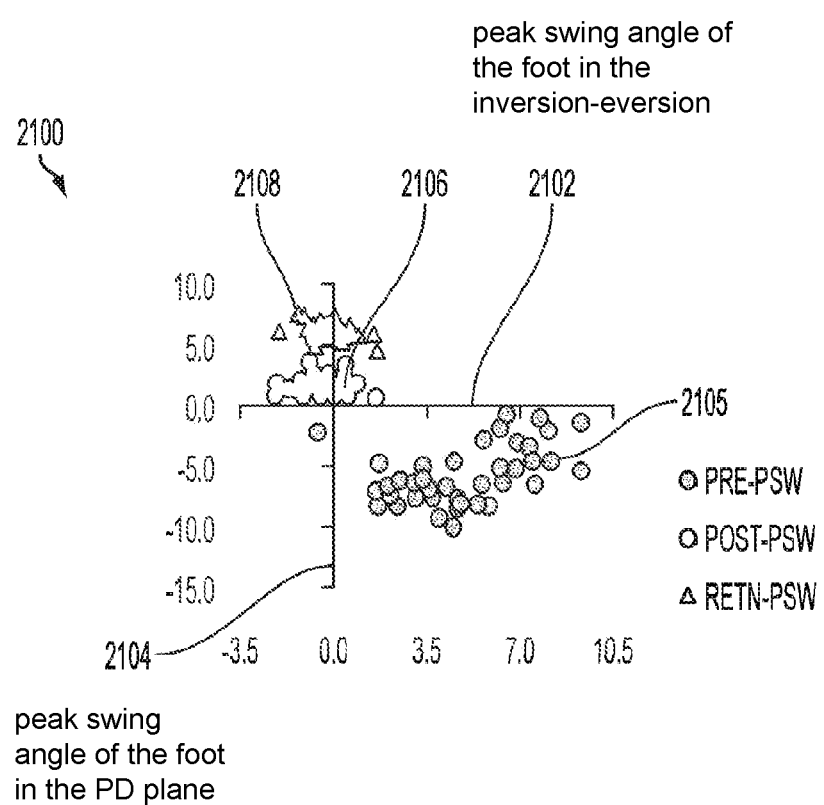
FIG. 21A is a graph that illustrates an example of peak swing angle data before and after use of a one-dimensional anklebot, according to an embodiment.

One example embodiment of the invention is utilized in the context of providing a version of the anklebot 300 discussed above, which only imparts (assistive or resistive) torque in one plane, such as the plantar-flexion/dorsiflexion plane (PD plane). However, the example embodiment is not limited to only imparting torque in the PD plane and in one example embodiment, only imparts torque in the IE plane. During the design of this anklebot, sample data was collected of four chronic stroke subjects using such a one-dimensional anklebot that only imparts torque in the PD plane. FIG. 21A is a graph 2100 that illustrates an example of peak swing angle data of the subjects before and after use of the anklebot, according to an embodiment. The horizontal axis 2102 represents the peak swing angle of the foot in the inversion-eversion, or the frontal plane (IE plane). The vertical axis 2104 represents the peak swing angle of the foot in the PD plane, similar to $\Theta_{max}$ discussed above in equation 2. During this data collection, the subjects wore the anklebot that only imparted torque in the PD plane and did not impart torque in the IE plane, permitting unconstrained movement in the IE plane.

Data points 2105 depict the peak swing angles in the IE plane and PD plane of each subject, prior to using the one-dimensional anklebot. Data points 2105 indicate a negative peak swing angle in the PD plane, which is indicative of the "drop foot" deficit, as previously discussed. Data points 2105 also indicate a positive peak swing angle in the IE plane, which is indicative of an inversion deficit (e.g., foot is tilted inward during the swing phase 406 of FIG. 4A). Data points 2106 depict the peak swing angles in the IE plane and PD plane of each subject, during three weekly sessions over a six week period. Data points 2106 indicate that the swing angle in the PD plane has increased from the negative swing angle in data points 2105 to a positive swing angle, which is indicative of substantial improvement in the "drop foot" deficit. Additionally, data points 2106 also indicate that a more anatomically neutral swing angle in the IE plane, which is indicative of an elimination of the inversion deficit. This result is surprising, given that the anklebot only imparted torque in the PD plane and did not impart torque in the IE plane. Data points 2108 depict the peak swing angles in the IE plane and PD plane of each subject, over a second six week period. Data points 2108 indicate that the swing angle in the PD plane has further increased from the swing angle in data points 2106, which is indicative of further improvement in the "drop foot" deficit. Additionally, data points 2108 continue to indicate the neutral swing angle in the IE plane, which is indicative of continued elimination of the inversion deficit, a synergistic and highly significant finding. As with data points 2106, this result is surprising, given that the anklebot only imparted torque in the PD plane and did not impart torque in the IE plane.

Figure 21B:
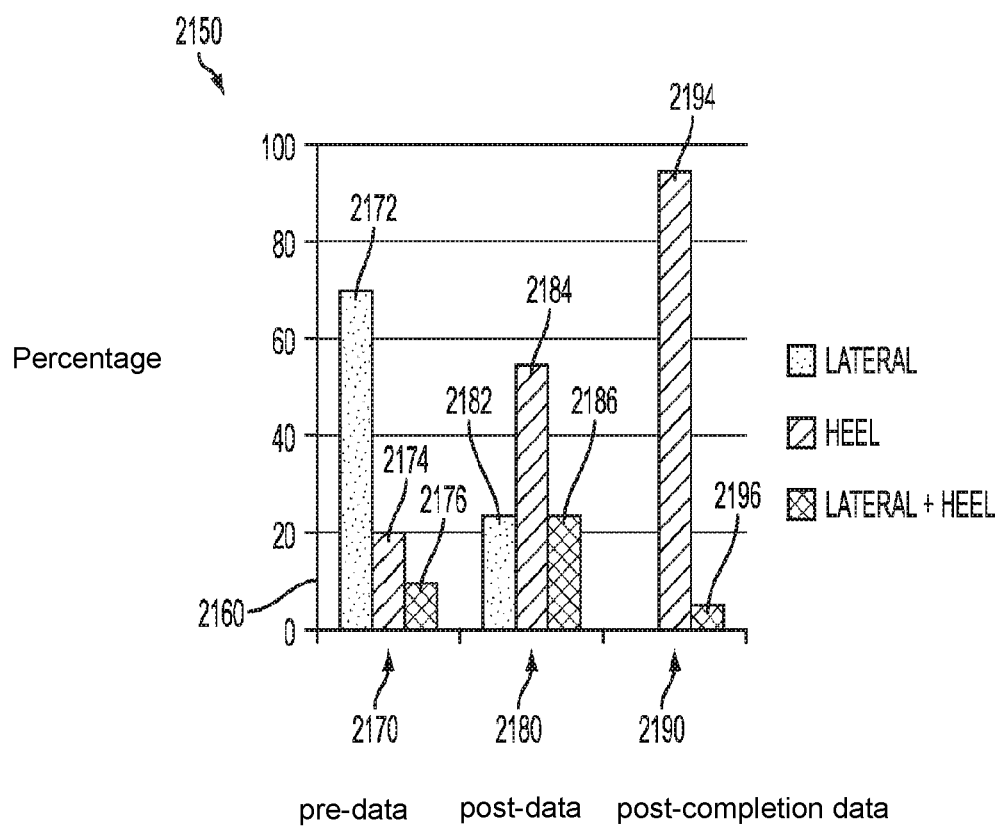
FIG. 21B is a histogram that illustrates an example of a frequency distribution of initial contact of different portions of the foot before and after use of a one-dimensional anklebot, according to an embodiment.

FIG. 21B is a histogram 2150 that illustrates an example of a distribution of initial contact of different portions of the foot with the ground before and after use of the one-dimensional anklebot, according to an embodiment. In an example embodiment, the distribution of initial contact in the histogram 2150 is a frequency distribution, expressed on the vertical axis 2160 as a percentage of the total number of footfalls during a one-minute unassisted walking trial on the treadmill with the anklebot donned, but not providing any assistance and only recording data. The histogram 2150 I s based on unassisted (anklebot in record-only mode) gait data captured using bilateral footswitches embedded inside the subjects shoes from an exemplar subject who was a participant in the same sample of subjects discussed above with regard to FIG. 21A and shows the distribution of lateral-only, lateral plus heel, and heel-only foot strikes during initial contact with the ground before and after 6-weeks, and at 6-week post-completion (retention). The subjects each wore the one-dimensional anklebot that imparted torque in only the PD plane and did not impart torque in the IE plane.

The histogram 2150 shows pre-data 2170 that was captured from the subjects prior to training with the anklebot.

Pre-data 2170 shows that the initial contact rate 2172 of the lateral region of the foot was approximately 70% of total footfalls, that the initial contact rate 2174 of the heel region of the foot was approximately 20% of the total footfalls, and that the initial contact rate 2176 of the combined lateral plus heel regions of the foot was approximately 10% of the footfalls. It is understood that non-disabled adults walk in a manner with the heel as the first region of contact with the ground when transitioning from the swing to the stance phase of gait (in other words, heel-first contact is the most ecological or normative pattern of landing). Hence, prior to anklebot training that targeted the PD plane, stroke patients walked in a manner that led to only one heel-first strike out of every five footfalls (20%) as shown by FIG. 21A, which is suggestive of abnormal gait patterning. The histogram 2150 also shows post-data 2180 that was captured after a six-week period while the subjects wore the anklebot during the one-minute unassisted walking trial on the treadmill. Post-data 2180 shows that the initial contact rate 2182 of the lateral region of the foot was approximately 25% of the total footfalls, that the initial contact rate 2184 of the heel region of the foot was approximately 50% of the total footfalls, and that the initial contact rate 2186 of the combined lateral plus heel regions of the foot was approximately 25% of the total footfalls. This shows significantly higher heel-first foot contacts with the ground (50%, or one heel-first strike out of every two footfalls) compared to 20% heel-first strikes prior to anklebot training, clear evidence of more volitional control of the foot during the landing phase due to alleviation in drop foot.

The histogram 2150 also shows 6-week post-completion (retention) data 2190 that was captured after a "no-training" six-week period while the subjects wore the anklebot in a record-only mode while walking on the treadmill for 1 minute. Retention-data 2190 shows that the initial contact rate of the lateral region of the foot is approximately 0% of the total footfalls, that the initial contact rate 2194 of the heel region of the foot is approximately 95% of the total footfalls, and that the initial contact rate 2196 of the combined lateral/heel regions of the foot is approximately 5% of the total footfalls, which is nearly normal gait as referenced to 100% heel-first strikes in non-disabled walking. The histogram 2150 data reveals that the initial contact rate of the heel region of the foot rose from approximately 20% of the total footfalls to 95% of the total footfalls, and that the initial contact rate of the lateral region of the foot fell from approximately 70% of the total footfalls to 0% of the total footfalls over the twelve-week period that the subjects used the anklebot in a one-dimensional actuated mode. This results in dramatic improvement in lateral stability of the subjects during the stance phase, which is a surprising but potent result, given that the anklebot only imparted torque in the PD plane and did not impart torque in the IE plane.

In view of the sample data collected above, it was concluded that a one-dimensional anklebot, which only imparts torque in the PD plane, would provide therapeutic benefits to subjects in both the PD plane and the IE plane, even though the latter is not actively actuated (but the foot is unconstrained or free to move in the lateral plane). As a result, various embodiments of one-dimensional anklebots that impart torque in only the PD plane are presented below. When referring to "one-dimensional", it is implied that the exoskeleton is actuated only in one plane (in this case, the PD plane) and no forces are sent to the other plane(s) (in this case, the IE plane) but the foot is unconstrained or free to move in the unactuated planes.

FIGS. 22A and 22B are block diagrams that illustrate an example lightweight portable system 2200 for providing deficit-adjusted adaptive assistance during a plurality of movement phases of an impaired ankle joint, according to an embodiment. The system 2200 is structured and operated in a similar manner as system 300 discussed above, with the exception of the specific structural features discussed herein and depicted in FIGS. 22A-22B. The system 2200 includes a controller (not shown) that is similar to the controller 140 previously discussed. The system 2200 includes a shoe 2202 (corresponding to beam 112b for connection to limb 193) to receive the subject's foot. The system 2200 also includes a single motor 2214 (corresponding to motor 116) that is connected to the shoe 2202 through a linear actuator 2216 (corresponding to beam 112a and drive chain 118).

The single motor 2214 and single linear actuator 2216 are connected along a front side of the leg by a strap 2204, which is secured around the calf. In another embodiment, the single motor 2214 and single linear actuator 2216 are connected along the front side of the leg by a strap that secures around another part of the leg, such as the knee, for example. The single motor 2214 and single linear actuator 2216 are connected to the front side of the leg such that they are oriented parallel to the tibia. The single motor 2214 and single linear actuator 2216 are connected to the shoe 2202 at a ball joint connector 2206 (corresponding to pivot 114) to selectively impart torque on the shoe 2202 in only a PD plane 2220 and to not impart torque on the shoe 2202 in an IE plane 2221 such that the foot is unconstrained in the IE plane 2221. In an example embodiment, the ball joint connector 2206 is secured to a surface of the shoe 2202. As the motor 2214 moves the linear actuator 2216 up or down, the shoe 2202 pivots the subject's foot about the subject's ankle. In an example embodiment, the system 2200 includes only one motor 2214. The method 200 of FIG. 2 is performed using the system 2200 in a similar manner as the system 300, with the exception of step 213, in which the single motor 2214 applies the adaptive magnitude of the anklebot applied torque on the shoe 2202 in only the PD plane 2220, for the current movement phase, based on the adaptive timing for the current movement phase.

Figure 22C:
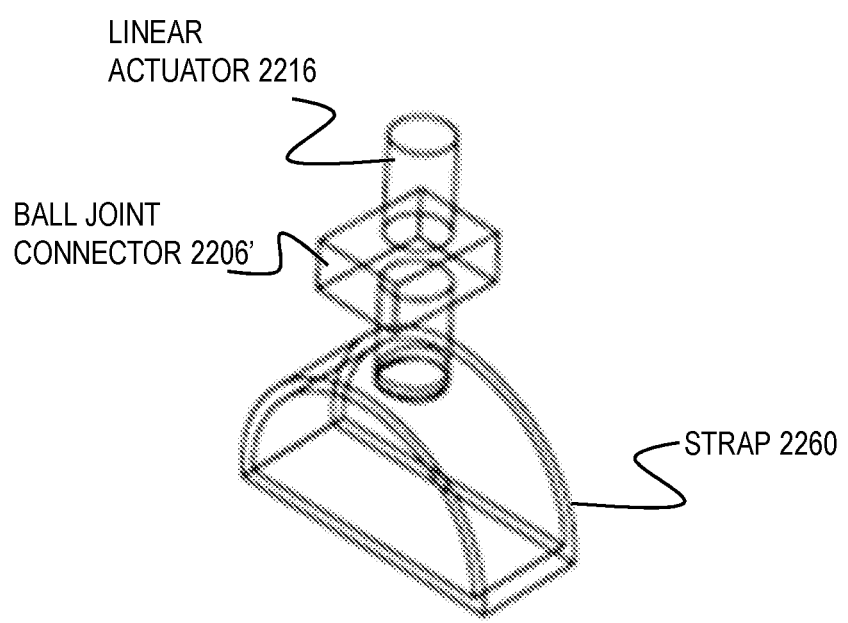
FIG. 22C is a block diagram that illustrates an example of an alternate ball joint connector to be used to couple the linear actuator to the shoe in the system of FIGS. 22A-22B.

FIG. 22C is a block diagram that illustrates an example of an alternate ball joint connector 2206' to be used to couple the linear actuator 2216 to the shoe 2202 in the system 2200 of FIGS. 22A-22B. As illustrated in FIG. 22C, the linear actuator 2216 is connected to the ball joint connector 2206' which is then subsequently connected to a strap 2260 that wraps around the shoe 2202, to evenly distribute the forces from the motor 2214 and linear actuator 2214 around the perimeter of the shoe 2202.

FIGS. 23A and 23B are block diagrams that illustrate an example lightweight portable system 2300 for providing deficit-adjusted adaptive assistance during a plurality of movement phases of an impaired ankle joint, according to another embodiment. The system 2300 is similar to the system 2200 discussed above, with the exception that the single motor 2214 and linear actuator 2216 are mounted to a first side of the leg, such as a lateral side or outside of the leg, using the strap 2204 secured around the calf. Additionally, as depicted in FIGS. 23A and 23B, a second linear actuator 2318 is mounted to a second side of the leg, such as a medial side or an inside of the leg. As illustrated in FIGS. 23A and 23B, the first linear actuator 2316 is joined by a connector 2319 to the second linear actuator 2318 so that the single motor 2214 is configured to actuate both the first and second linear actuators 2316, 2318. In an example embodiment, the connector 2319 is a passive link. Additionally, as depicted in FIGS. 23A and 23B, a pair of ball joint connectors 2306 (corresponding to pivot 114) is provided on either side of the shoe 2202. The single motor 2214 is connected to the pair of ball joint connectors 2306 through the first and second linear actuators 2316, 2318, to impart the robot-applied torque about the pair of ball joint connectors 2306 in only the PD plane 2220. The method 200 of FIG. 2 is performed using the system 2300 in a similar manner as the system 300, with the exception of step 213, in which the single motor 2214 applies the adaptive magnitude of the anklebot applied torque on the shoe 2202 in only the PD plane 2220, for the current movement phase, based on the adaptive timing for the current movement phase.

As further illustrated in FIGS. 23A and 23B, the system 2300 includes a user-controlled toggle switch 2314 for the subject to select a desired movement phase to receive robotic assistance (torque) in an easy to toggle fashion among the plurality of movement phases (e.g., phases 402, 404, 406 depicted in FIG. 4A). Although FIG. 23A depicts that the toggle switch 2314 is located adjacent to the motor 2214 housing, the location of the toggle switch 2314 may be anywhere in the system 2300 or on the patient's person, such as a Bluetooth wrist watch or on a belt or a pocket or in a pouch, provided that the user have easy and quick access to the toggle switch 2314. The user-controlled toggle switch enables the delivery of an adaptively timed robot-applied torque during one (such as, the swing phase of gait) or more (such as, the swing and stance phases of gait) movement phases out of many possible movement phases, as well as a "no-assist" for any movement phase option. The binary movement phase toggle selection (that is, either stance phase or swing phase, but not both) enables the subject to work on fewer than all movement phases (e.g., only one movement phase) deficit(s) at a time.

In an example embodiment, the toggle switch 2314 can also be used to select an unassisted mode, where the motor 2214 via linear actuators does not impart any torque on the shoe 2202 during any of the movement phases, thus allowing the subject to practice walking in the unassisted mode, while the robot records ankle kinematics for clinician or therapist review. Based on the desired movement phase selected using the toggle switch 2314, the adaptive timing of step 209 is determined, based on whether the current movement phase corresponds to the desired movement phase.

Figure 24:
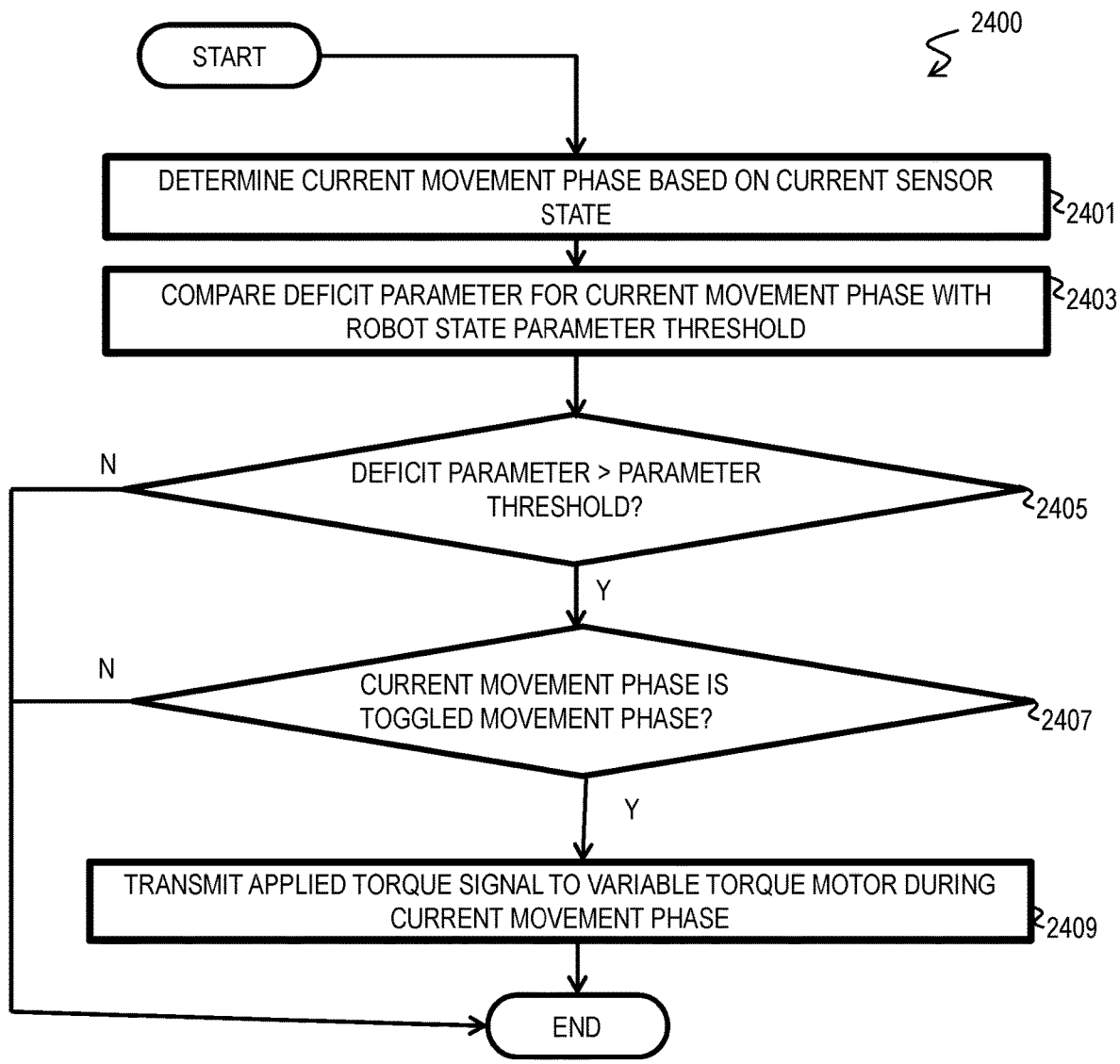
FIG. 24 is a flow diagram that illustrates an example of a method for determining an adaptive timing in the method of FIG. 2.

FIG. 24 is a flow diagram that illustrates an example of a method 2400 for determining the adaptive timing in step 209 of the method 200 of FIG. 2. In step 2401, the current movement phase is determined, based on the current sensor state 168, as previously discussed. In step 2403, the deficit parameter 167 for the current movement phase is compared with a robot state parameter threshold for the current movement phase, as previously discussed. In step 2405, if the deficit parameter 167 is less than the robot state parameter threshold, then the method 2400 terminates with no voltage sent to the motor 2214 during the current movement phase. In step 2405, if the deficit parameter 167 is greater than the robot state parameter threshold, the method 2400 proceeds to step 2407.

In step 2407, if the current movement phase is not the same as the desired movement phase selected by the toggle switch 2314, the method 2400 terminates and no voltage is sent to the motor 2214 during the current movement phase. In step 2407, if the current movement phase is the same as the desired movement phase, the method 2400 proceeds to step 2409, where an appropriate voltage is sent to the motor 2214 during the current movement phase. Upon receiving the voltage, the motor 2214 imparts a torque on the shoe 2202 about the ball joint connectors 2306 in only the PD plane 2220, based on the adaptive magnitude determined in step 211. Although the toggle switch 2314 is depicted in the system 2300 of FIGS. 23A-23B, the toggle switch 2314 may be omitted or included in any of the embodiments disclosed herein. In an example embodiment, the toggle switch 2314 may be omitted for pre-programmed movement phase adaptively timed assistance without conferring any user control. In another example embodiment, the toggle switch 2314 may be included to confer user control to change desired movement phase that may or may not be different from the default movement phase programmed as per clinically diagnosed predominant deficit that is, weak propulsion for stance phase or foot drop for swing phase.

In an example embodiment of use of the toggle switch 2314, if the subject experiences the "foot slap" deficit during early stance 402 phase and experiences the "drop foot" deficit during swing 406 phase, the subject can use the toggle switch 2314 to selectively choose to work only on the "drop foot" deficit, before working on the "foot slap" deficit (or vice versa). The subject uses the toggle switch 2314 to select the swing 406 phase as the desired movement phase. After a number of training sessions and/or achieving a certain level of improvement in the "drop foot" deficit, the subject can then use the toggle switch 2314 to select the early stance 402 phase as the desired movement phase, in order to work only on the "foot slap" deficit.

Figure 25:
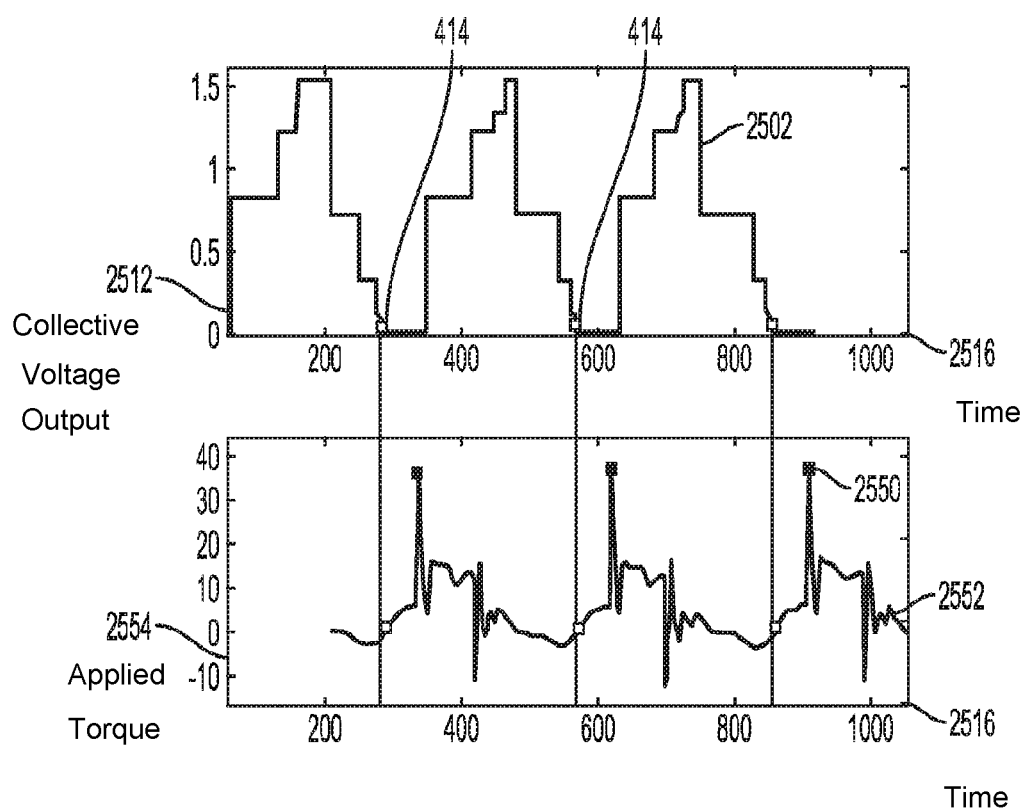
FIG. 25 is matched pair of graphs that illustrate traces of sensor state output and applied torque to the foot over the plurality of movement phases of the gait cycle of FIG. 4A.

This example embodiment is depicted in FIG. 25, which is pair of graphs that illustrates traces 2502, 2552 of sensor state output and applied torque to the foot over the plurality of movement phases of the gait cycle of FIG. 4A. The sensor state trace 2502 is similar to the sensor state trace 424 of FIG. 4B, with a horizontal time axis 2516 and a vertical axis 2512 of the collective voltage output from footswitches 425. The applied torque trace 2552 also has a horizontal time axis 2516 and a vertical axis 2554 of the applied torque by the motor 2214 to the shoe 2202 in only the PD plane 2220. As depicted in FIG. 25, since the subject used the toggle switch 2314 to choose the swing 406 phase as the desired movement phase, the applied torque reaches a peak 2550 shortly after the heel off 414 movement phase, when the subject is in the swing 406 phase (see FIG. 4A), to assist the subject during the swing phase. Since the swing 406 phase is selected as the desired movement phase, the applied torque does not impart a deficit torque during any of the other movement phases. In this example embodiment, the applied torque is zero during all movement phases except the swing 406 phase, in accordance with the deficit-adjusted phase approach (such as foot drop during the swing 406 phase.

Figure 26:
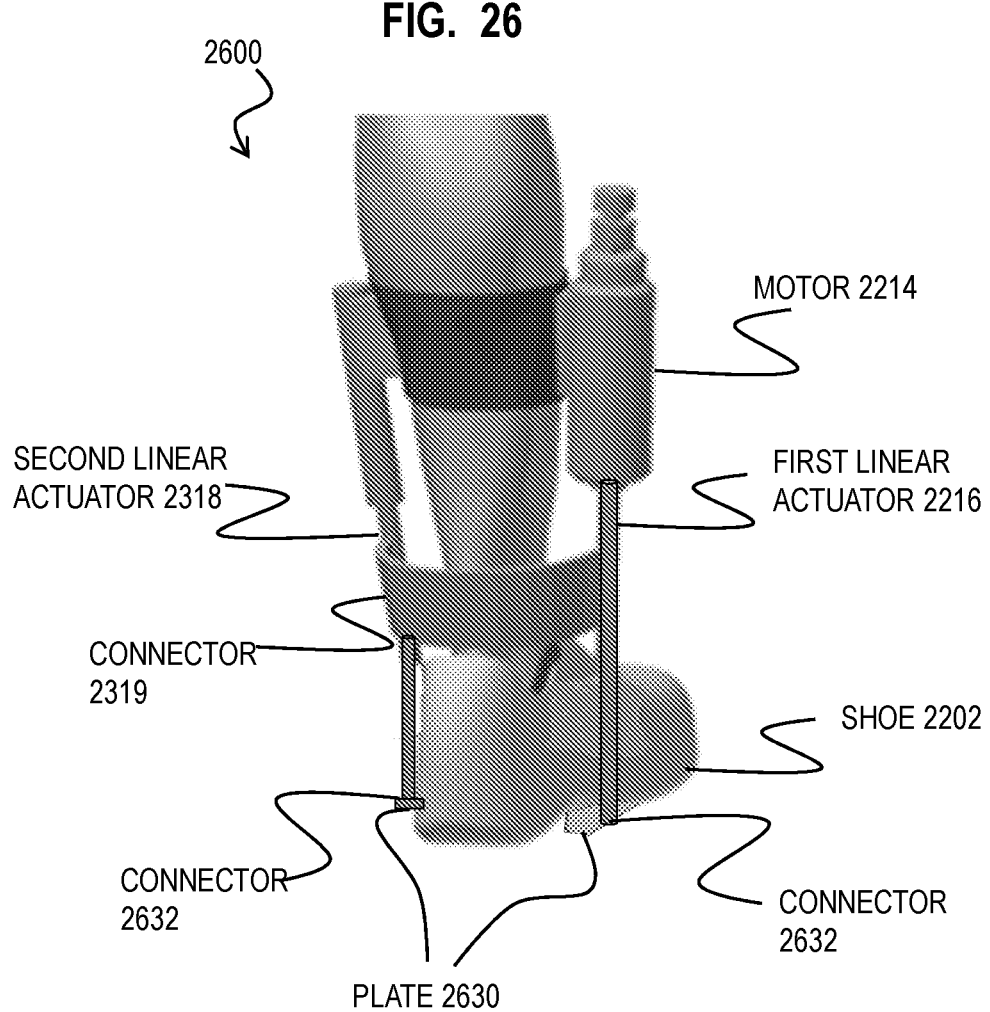
FIG. 26 is a block diagram that illustrates an example lightweight portable system for providing deficit-adjusted adaptive assistance during a plurality of movement phases of an impaired ankle joint, according to another embodiment.

FIG. 26 is a block diagram that illustrates an example lightweight portable system 2600 for providing deficit-adjusted adaptive assistance during a plurality of movement phases of an impaired ankle joint, according to an embodiment. The system 2600 is similar to the system 2300 discussed above, with the exception that a pair of connectors 2632 (corresponding to pivot 114) is provided on either side of a plate 2630 positioned underneath a base of the shoe 2202. The single motor 2214 is connected to the pair of connectors 2632 through the first and second linear actuators 2316, 2318, to impart the robot-applied torque about the pair of connectors 2632 in only the PD plane 2220. The method 200 of FIG. 2 is performed using the system 2600 in a similar manner as the system 300, with the exception of step 213, in which the single motor 2214 applies the adaptive magnitude of the anklebot applied torque on the shoe 2202 in only the PD plane 2220, for the current movement phase, based on the adaptive timing for the current movement phase. This embodiment allows the subject to use a normal shoe while obtaining assistance from the anklebot.

Figure 27:
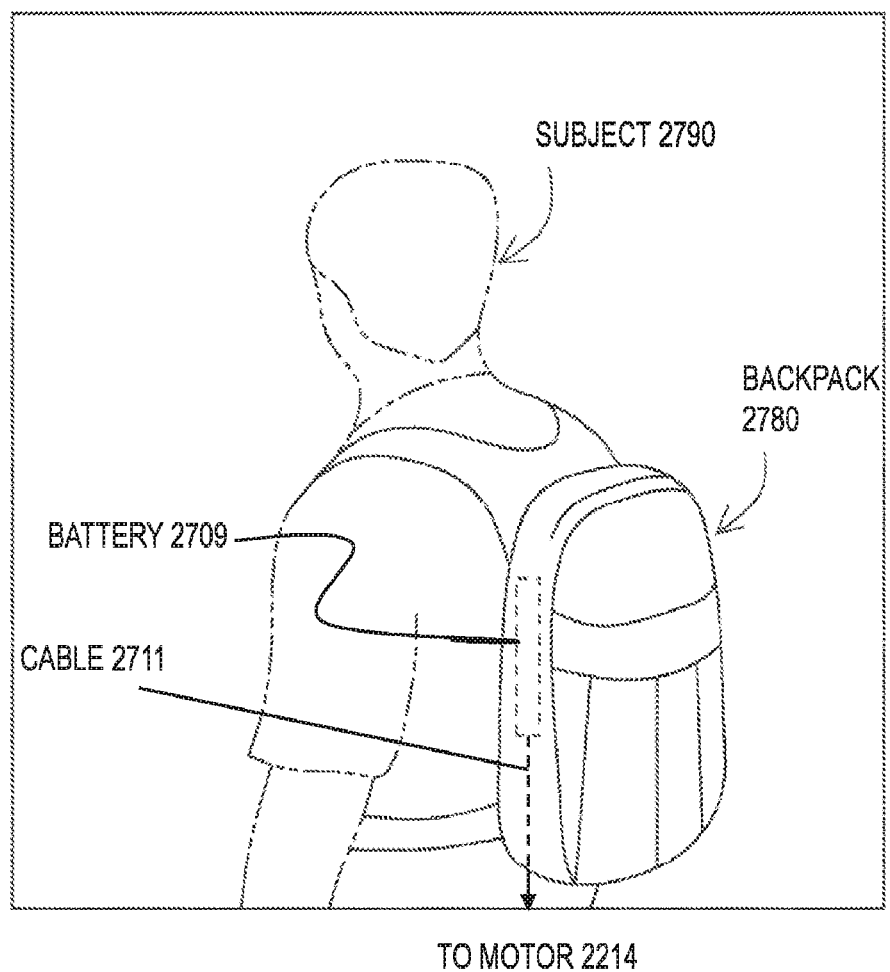
FIG. 27 is a block diagram that illustrates an example of a power source carried by a subject in the system of FIGS. 22A-22B.

FIG. 27 is a block diagram that illustrates an example of a power source for the motor 2214 carried by a subject 2790 in the system 2200 of FIGS. 22A-22B. In an example embodiment, the power source is a battery 2709 that is carried in a backpack 2780 worn by the subject 2790. In an example embodiment, the power source is a high capacitance (long life) battery. A cable 2711 connects the battery 2709 to the motor 2214, so that the system 2200 is portable (mobile) and the subject can use the system 2200 without any tethering to an external power source. In an example embodiment, the battery 2709 is a rechargeable battery, such as a rechargeable 200-watt battery. Although FIG. 27 depicts that the subject 2790 carries the battery 2709 in the backpack 2780, the subject 2790 can carry the battery 2709 anywhere on their person, such as in a pouch or a pocket or on a belt, for example.

Figure 29A:
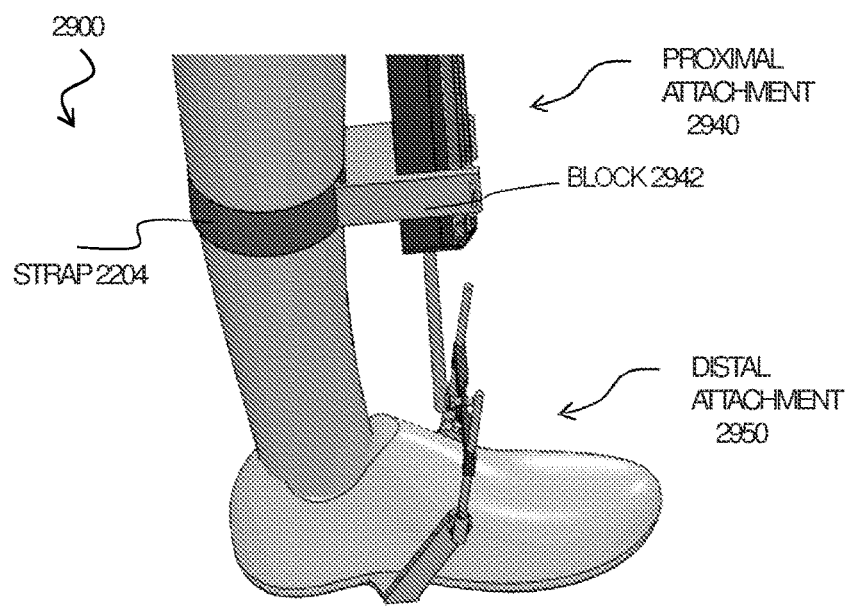
Figure 29B:
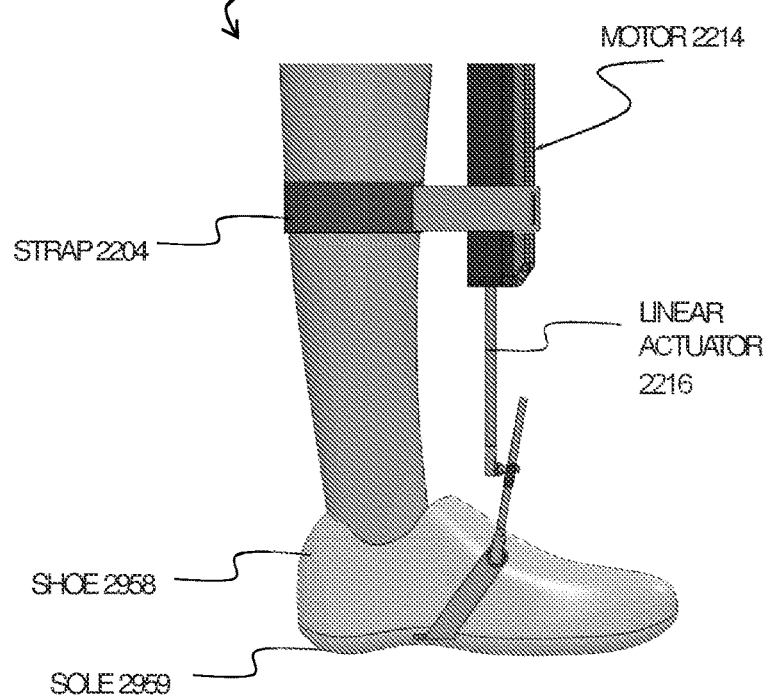

FIGS. 29A-29C are block diagrams that illustrate an example lightweight portable system 2900 for providing deficit-adjusted adaptive assistance during a plurality of movement phases of an impaired ankle joint, according to an embodiment. The system 2900 is similar to the system 2200 discussed above, with the exception of the features discussed herein. The system 2900 includes a proximal attachment 2940 as beam 112*a* that attaches the motor 2214 and linear actuator 2216 (corresponding to motor 116 and beam 112*a*) to the leg (corresponding to body 191) above the ankle (corresponding to joint 192) of the subject. In an example embodiment, the proximal attachment 2940 attaches the motor 2214 and linear actuator 2216 to the leg below the knee. In another example embodiment, the proximal attachment 2940 attaches the motor 2214 and linear actuator 2216 to the leg above and below the knee. In this example embodiment, the proximal attachment 2940 includes the strap 2204 that secures the motor 2214 and linear actuator 2216 around the calf and a block 2942 secured to the strap 2204 that is shaped to removably attach the motor 2214 and linear actuator 2216 to the strap 2204. In an example embodiment, the block 2942 forms to a slot in which the motor 2214 is slidably received and fixed within the slot during use of the system 2900.

FIG. 29D is a block diagram that illustrates an example of a distal attachment 2950 used as a beam 112*b* to couple the linear actuator 2216 to the foot in the system of FIGS. 29A-29C. The distal attachment 2950 attaches the linear actuator 2216 to the foot (corresponding to limb 193) below the ankle of the subject. In an example embodiment, the distal attachment 2950 includes a stirrup 2952 secured around the foot of the subject, where the stirrup 2952 includes side plates 2954*a*, 2954*b* rotatably coupled to the linear actuator 2216 at a junction 2956 (corresponding to pivot 114). In an example embodiment, the junction 2956 corresponds to a top end of the side plates 2954*a*, 2954*b*. In an example embodiment, the distal attachment 2950 further includes a shoe 2958 with a sole 2959 where a bottom end of the sides plates 2954*a*, 2954*b* are integral with the sole 2959. Shoes 2958 of various sizes are provided, to accommodate subjects with different sized feet. In an example embodiment, the side plates 2954*a*, 2954*b* are integral with the sole 2959 adjacent to an arch region of the sole 2959. In an example embodiment, the side plates 2954*a*, 2954*b* have a length of about 110 millimeters (mm) or in a range from about 100 mm to about 120 mm and form an angle of about 18 degrees (18 deg) or in a range from about 10 deg to about 25 deg with respect to the sole 2959. In some embodiments, the side plate 2954*a*, 2954*b* length is adjustable to account for different shoe sizes and in particular, the shoe sole 2959 height. In some embodiments, the side plate 2954*a*, 2954*b* angulation is adjustable to yield variable desired effective moment arms for gender-specific foot anthropometrics (e.g. shoe size and shoe shape). In an example embodiment, the distal attachment 2950 further includes one or more first bars 2960*a*, 2960*b* secured to the respective side plates 2954*a*, 2954*b* at the junction 2956 and a second bar 2962 that connects the first bars 2960*a*, 2960*b* and is also connected to the linear actuator 2216. The second bar 2962 is configured to transfer movement of one linear actuator 2216 to multiple side plates 2954*a*, 2954*b*, e.g., through corresponding bars 2960*a*, 2960*b*. This offers an advantage of producing movement in only the PD plane 2220 using a single linear actuator 2216, which reduces the cost and weight of the portable anklebot. In an example embodiment, the second bar is oriented approximately orthogonal to the first bars 2960*a*, 2960*b*.

As the single motor 2214 moves the single linear actuator 2216 up or down, the first bars 2960*a*, 2960*b* and second bar 2962 simultaneously impart an upward or downward force at the junction 2956, which in-turn selectively imparts torque on the shoe 2958 about the junction 2956 in only the PD plane 2220 and does not impart torque on the shoe 2958 in the IE plane 2221 such that the foot is unconstrained in the IE plane 2221. In an example embodiment, dorsiflexion torque is imparted on the shoe 2958 in the PD plane 2220 based on upward movement of the linear actuator 2216 and plantarflexion torque is imparted on the shoe 2958 in the PD plane 2220 based on downward movement of the linear actuator 2216.

Figure 29G:
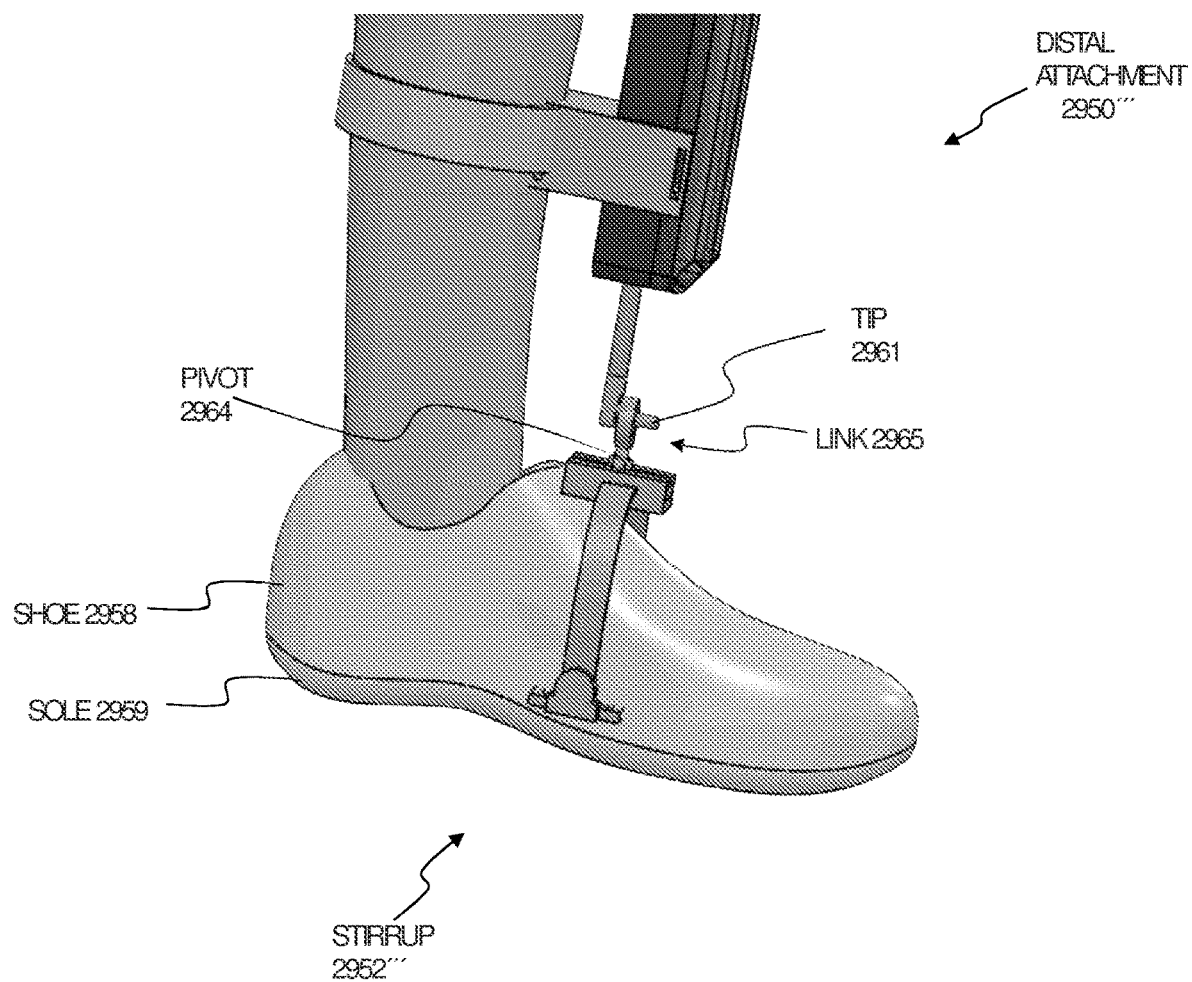
FIG. 29G is a block diagram that illustrates an example of a distal attachment used as a beam to couple the linear actuator to the foot in the system of FIGS. 29E-29F.
Figure 29H:
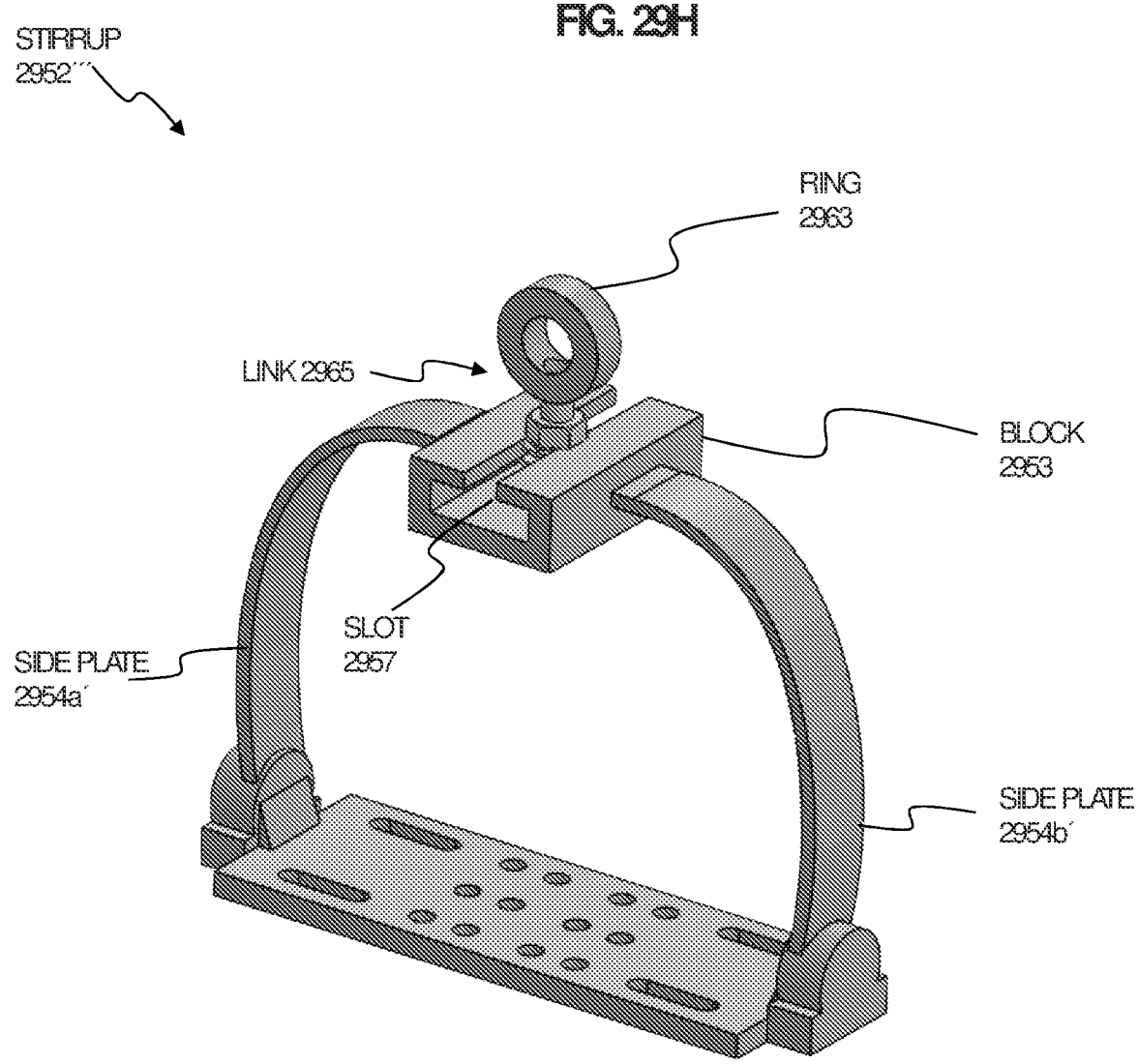
FIG. 29H is a block diagram that illustrates an example of a stirrup of the distal attachment of FIG. 29G.

FIGS. 29E-29F are block diagrams that illustrate an example lightweight portable system 2900' for providing deficit-adjusted adaptive assistance during a plurality of movement phases of an impaired ankle joint, according to an embodiment. FIG. 29G is a block diagram that illustrates an example of a distal attachment 2950''' used as a beam to couple the linear actuator 2216 to the foot in the system 2900' of FIGS. 29E-29F. The system 2900' is similar to the system 2900 discussed above and depicted in FIGS. 29A-29D with the exception of the features discussed herein. Unlike the distal attachment 2950 of the system 2900, that features planar side plates 2954*a*, 2954*b* coupled to the linear actuator 2216 through the first bars 2960*a*, 2960*b* and the second bar 2962, the distal attachment 2950''' of the system 2900' features arcuate side plates 2954*a'*, 2954*b'* coupled to the linear actuator 2216 through a block 2953 and a link 2965 featuring a ring 2963. In an example embodiment, the arcuate side plates 2954*a'*, 2954*b'* are connected to opposite sides of the block 2953. In another example embodiment, the arcuate side plates 2954*a'*, 2954*b'* are integral with the block 2953. In some embodiments, the arcuate side plates 2954*a'*, 2954*b'* each exhibit one or more radii of curvature selected to effects a vertical distance from the pivot to the sole while traversing a horizontal distance of at least half the width of the shoe or foot of the subject. In an example embodiment, the radii of curvature of the side plates 2954*a'*, 2954*b'* is 43 mm or in a range from about 35 mm to about 50 mm.

In the illustrated embodiment, the block 2953 features a slot 2957 that is sized to receive a first end (not shown) of the link 2965 and secure the first end within the slot 2957 to form a pivot 2964. In some embodiments, the pivot 2964 slides along the slot 2957, which advantageously allows the link 2965 to remain stationary (e.g. within the reference frame of the foot) as the angle of the side plates 2954*a'*, 2954*b'* is adjusted to accommodate shoes of different size. In an example embodiment, this structural arrangement of the pivot 2964 within the slot 2957 accounts for a less inclined angle of the side plates 2954*a*', 2954*b*' for smaller sized shoes and a more inclined angle of the side plates 2954*a*', 2954*b*' for larger sized shoes. A second end of the link 2965 opposite to the first end features a ring 2963 that is sized to receive a tip 2961 of the linear actuator 2216 and to secure the tip 2961 within the ring 2963. In some embodiments, there is a friction fit between the second end of the link 2965 and the ring 2963. In an example embodiment, the friction fit is designed from stiff friction fit rubber material. In another example embodiment, the tip 2961 is secured to the ring 2963 with a wingnut (not shown). In an example embodiment, the second end of the link 2965 is not limited to a ring and can include any design with an opening sized to receive the tip 2961 of the linear actuator 2216. In an example embodiment, the pivot 2964, such as a ball joint connector, is provided between the ring 2963 and the first end of the link 2965.

As the single motor 2214 moves the single linear actuator 2216 up or down, the tip 2961, the ring 2963 and the block 2953 simultaneously impart an upward or downward force at the pivot 2964 corresponding to the junction 2956', which in-turn selectively imparts torque on the shoe 2958 about the junction 2956' in only the PD plane 2220 and does not impart torque on the shoe 2958 in the IE plane 2221 such that the foot is unconstrained in the IE plane 2221.

Figure 30A:
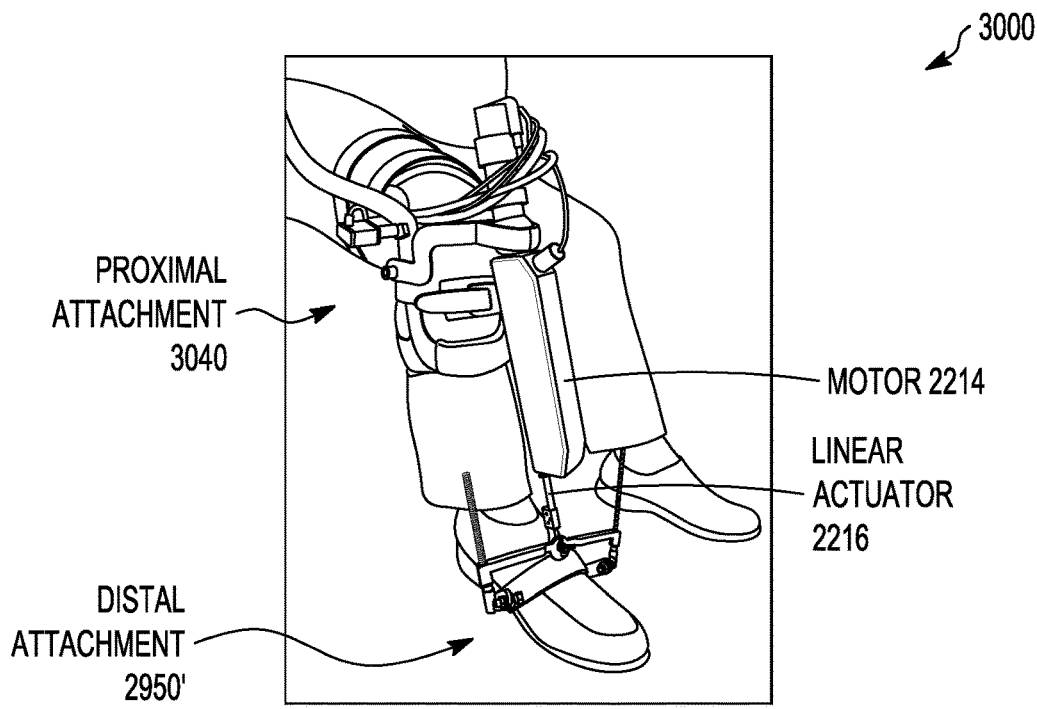
FIG. 30A is a photograph that illustrates an example lightweight portable system for providing deficit-adjusted adaptive assistance during a plurality of movement phases of an impaired ankle joint, according to an embodiment.
Figure 30B:
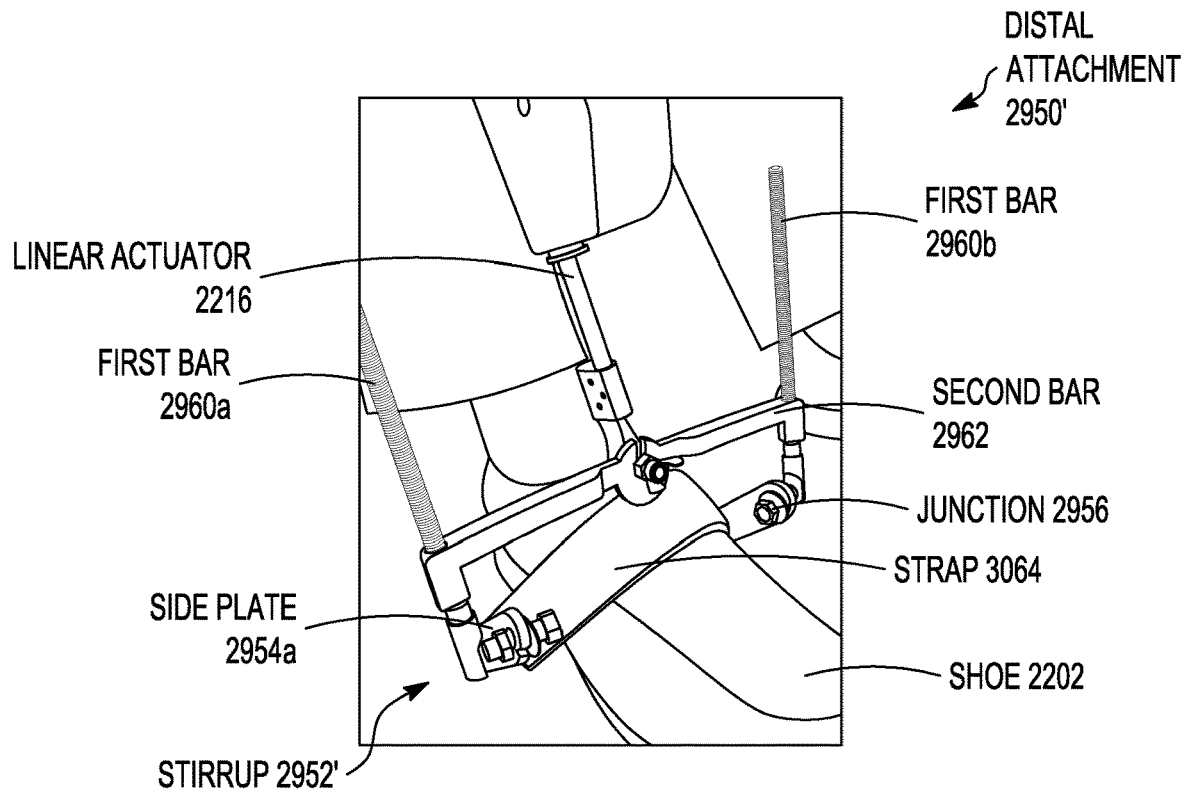
FIG. 30B is a photograph that illustrates an example of a distal attachment used to couple the linear actuator to the foot in the system of FIG. 30A.

FIG. 30A is a photograph that illustrates an example lightweight portable system 3000 for providing deficit-adjusted adaptive assistance during a plurality of movement phases of an impaired ankle joint, according to an embodiment. The system 3000 is similar to the system 2200 discussed above, with the exception of the features discussed herein. FIG. 30B is a photograph that illustrates an example of a distal attachment 2950' used to couple the linear actuator 2216 to the foot in the system 3000 of FIG. 30A. The distal attachment 2950' is similar to the distal attachment 2950 with the exception that the stirrup 2952' is not integral with the shoe 2202. Instead, the distal attachment 2950' includes a strap 3064 that wraps around the shoe 2202, to secure the stirrup 2952' around the perimeter of the shoe 2202 and thus evenly distribute the imparted torque on the shoe 2202 about the junction 2956 in only the PD plane 2220. In an example embodiment, the distal attachment 2950' is configured to accommodate a range of shoe sizes that range from U.S. Women's size 6 (e.g. foot length 22.5 cm) to U.S. Men's size 12 (e.g. foot size 28.6 cm). In this example embodiment, the shoe 2202 is not part of the system 3000 and thus the system 3000 advantageously permits any type of shoe to be used.

Figure 30C:
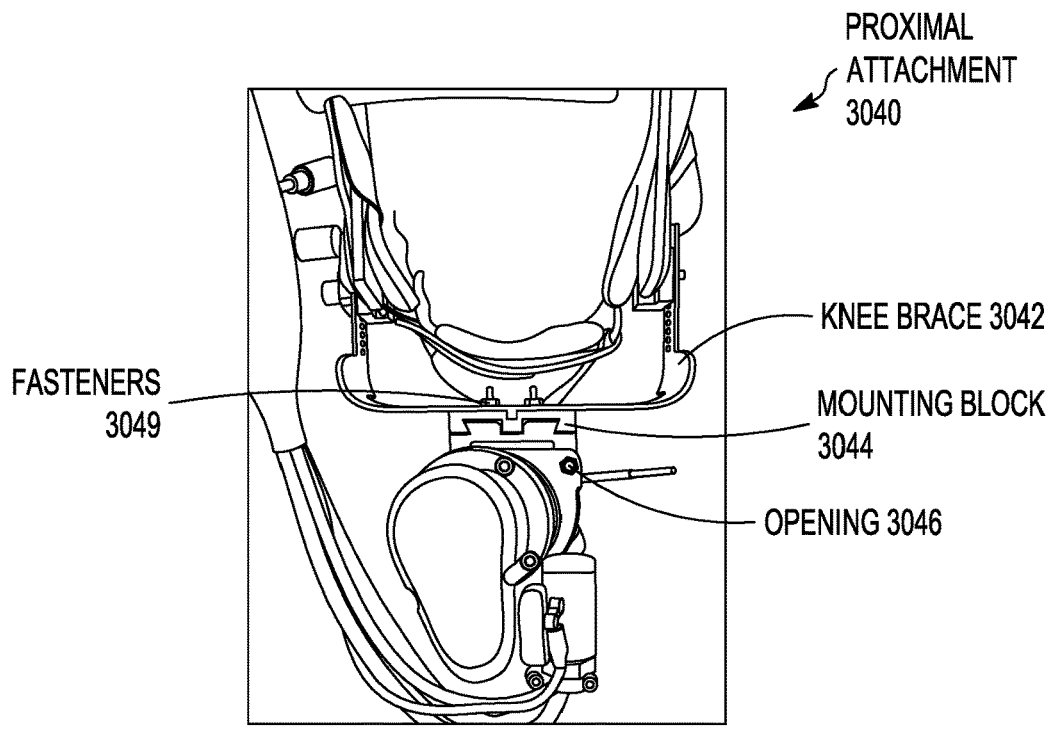
FIGS. 30C-30D are photographs that illustrate an example of a proximal attachment used as a beam to couple the linear actuator to the leg in the system of FIG. 30A.
Figure 30D:
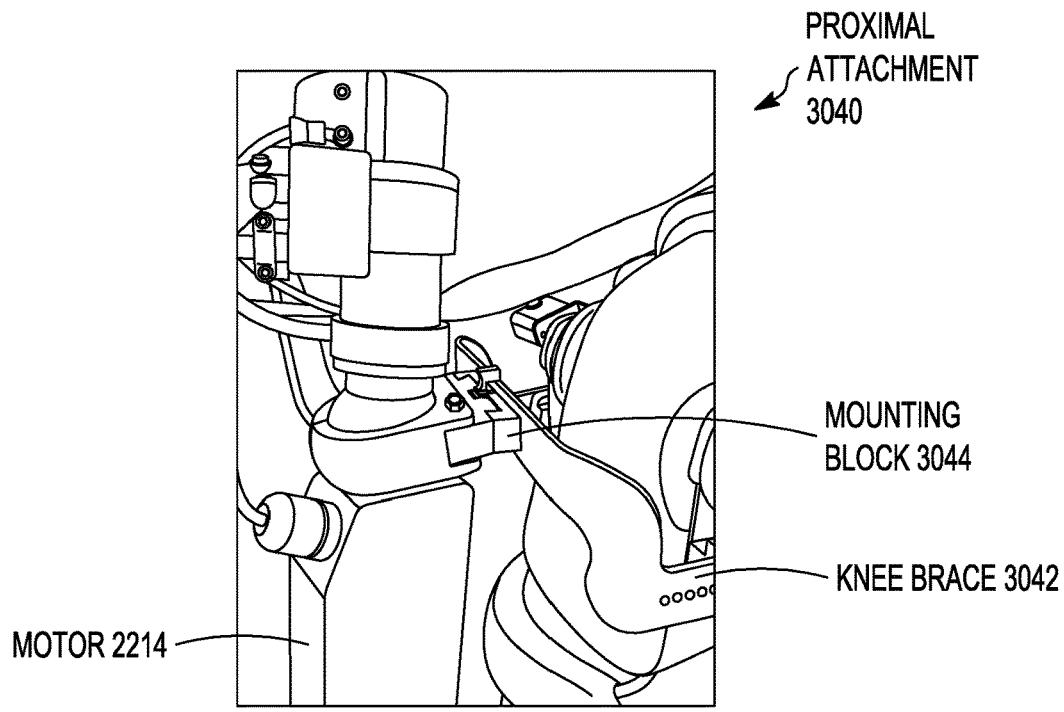

FIGS. 30C-30D are photographs illustrate an example of a proximal attachment 3040 used as a beam to couple the motor 2214 and linear actuator 2216 to the leg in the system 3000 of FIG. 30A. In various example embodiments, the proximal attachment 3040 attaches the motor 2214 and linear actuator 2216 to the leg at the knee and/or above the knee. The proximal attachment 3040 includes a knee brace 3042 secured to the knee, as appreciated by one skilled in the art. In an example embodiment, the proximal attachment 3040 also includes a mounting block 3044 that is secured on one side to the knee brace 3042 and includes one or more openings 3046 on a second side to mount the single motor 2214 and single linear actuator 2216.

Figure 30E:
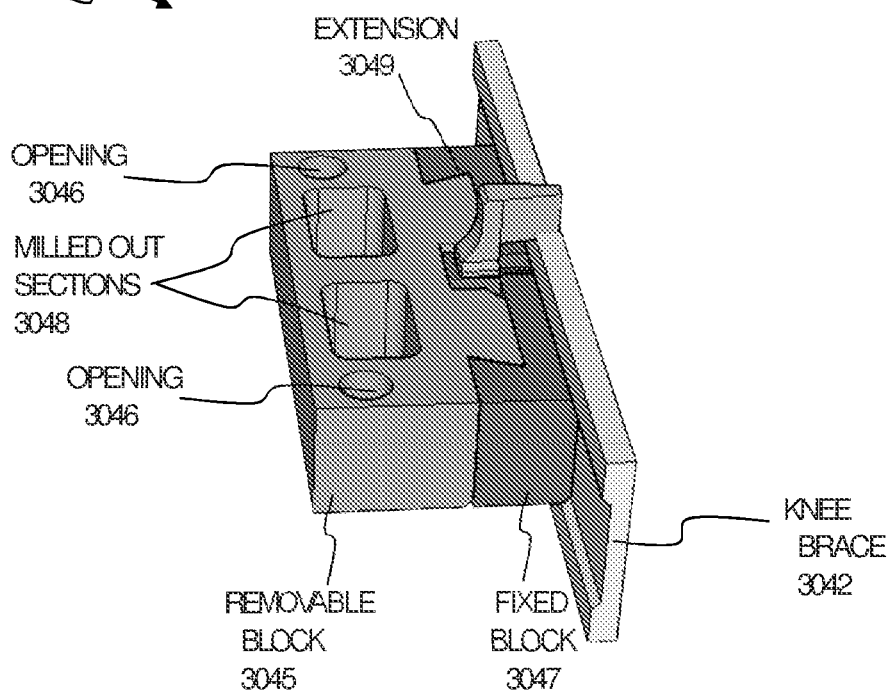
FIG. 30E is a block diagram that illustrates an example of a mounting block used to couple the linear actuator to the leg in the proximal attachment of FIGS. 30C-30D.

FIG. 30E is a block diagram that illustrates an example of a mounting block 3044 used to couple the motor 2214 and linear actuator 2216 to the leg in the proximal attachment 3040 of FIGS. 30C-30D. The mounting block 3044 includes a fixed block 3047 that is secured to the knee brace 3042 using fasteners 3049 (see FIG. 30C). A removable block 3045 is then removably attached to the fixed block 3047 by sliding a pair of arcuate extensions 3049 into corresponding arcuate slots in the fixed block 3047. In an example embodiment, the removable block 3045 includes the openings 3046 to mount the single motor 2214 and single linear actuator 2216. The mounting block 3044 advantageously permits the single motor 2214 and single linear actuator 2216 to be easily removed and reattached to the knee brace 3042. In an example embodiment, the removable block 3045 also includes milled out sections 3048 to reduce a weight of the mounting block 3044 and thus reduce a weight of the system 3000. In the illustrated embodiment, the dimensions of the mounting block 3044 include an approximate length of 60 millimeters (mm), a width of 30 mm and a height of 15 mm. However, in other embodiments, the dimensions of the mounting block 3044 are not limited to any specific numerical dimensions. In some embodiment, where the mounting block 3044 is produced by 3D printing, the mounting block 3044 is made of Acrylonitrile Butadiene Styrene. In some embodiments, where the mounting block 3044 is machined, the mounting block 3044 is made of Aluminum 6061-T6 material. In some embodiments, the dimensions of each milled out section 3048 includes an approximate length of 15 mm and a width of 10 mm.

Figure 30F:
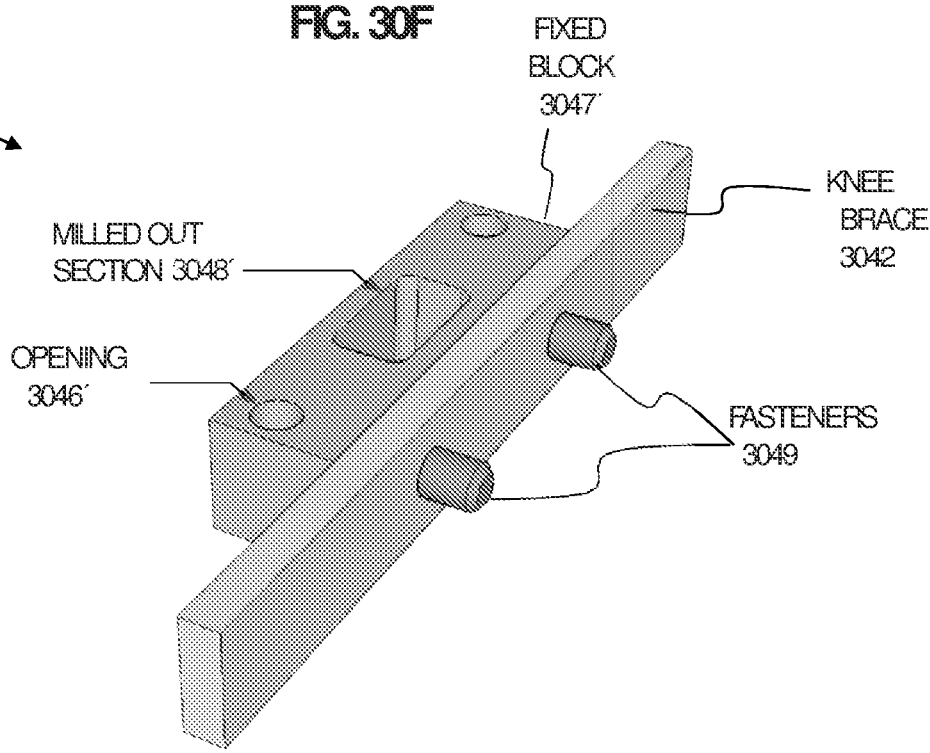
FIG. 30F is a block diagram that illustrates an example of a mounting block used to couple the linear actuator to the leg in the proximal attachment of FIGS. 30C-30D.

FIG. 30F is a block diagram that illustrates an example of a mounting block 3044' used to couple the motor 2214 and linear actuator 2216 to the leg in the proximal attachment 3040 of FIGS. 30C-30D. Unlike the mounting block 3044, where the openings 3046 and milled out sections 3048 are formed in the removable block 3045, the mounting block 3044' does not feature a removable block and instead the fixed block 3047' secured to the knee brace 3042 features the openings 3046' and a milled out section 3048'.

Figure 31A:
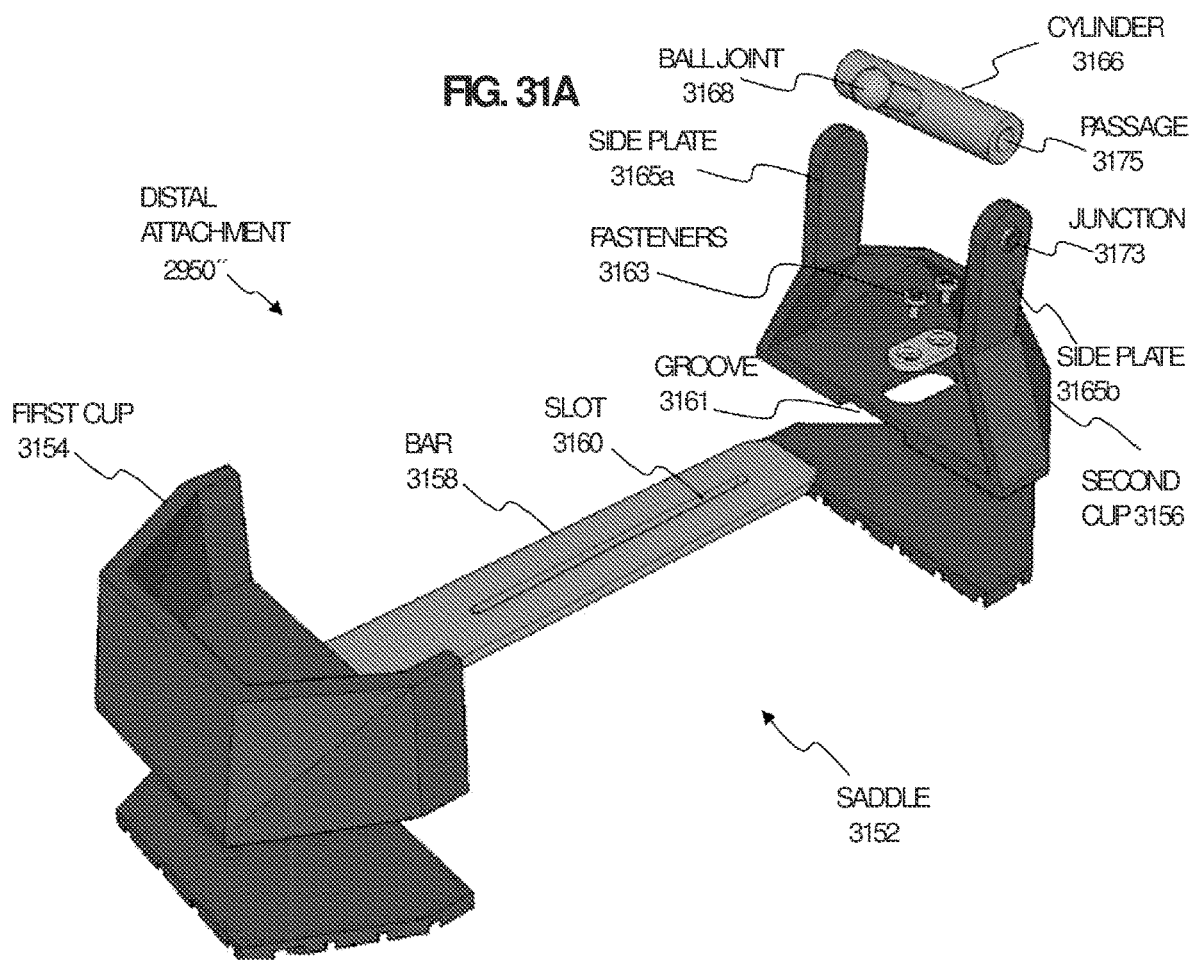
FIGS. 31A-31B are block diagrams that illustrate an example of a distal attachment used as a beam to couple the linear actuator to the foot in the system of FIG. 30A.
Figure 31C:
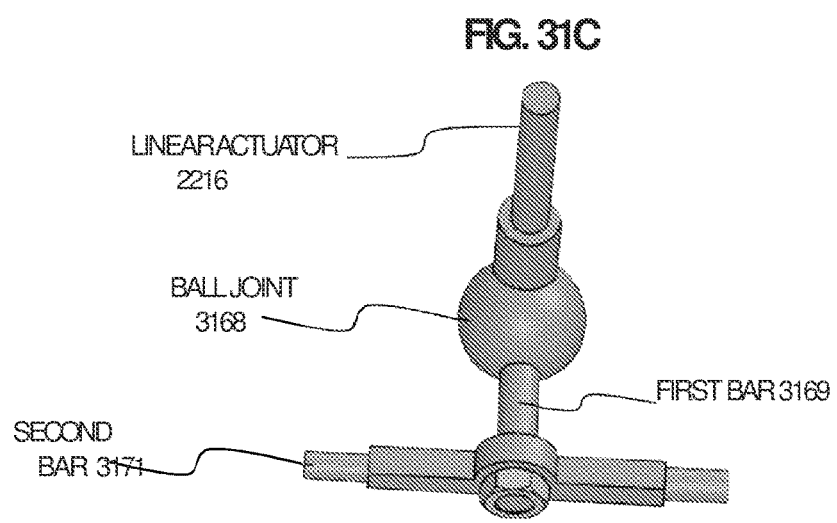
FIG. 31C is a block diagram that illustrates an example of a ball joint used to couple the linear actuator to the foot in the distal attachment of FIGS. 31A-31B.
Figure 31B:
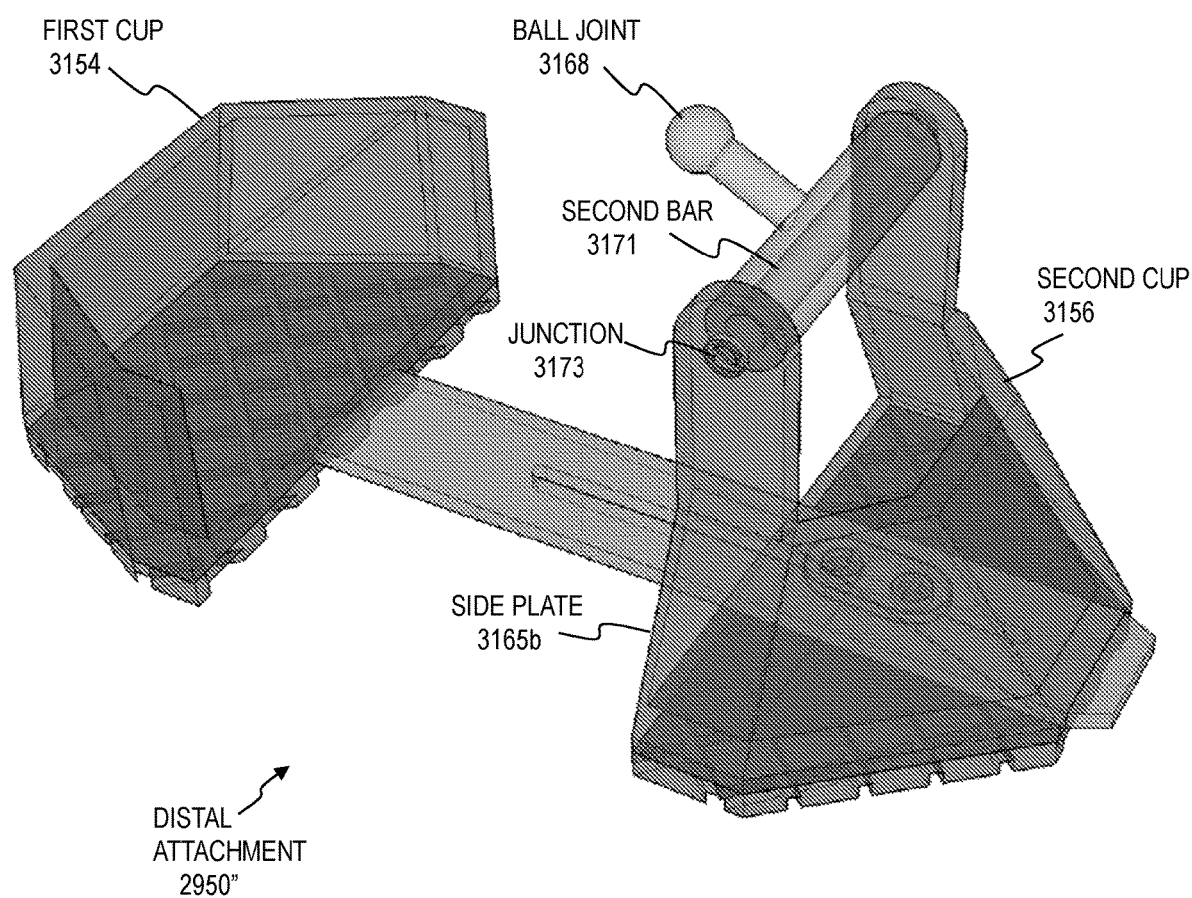

FIGS. 31A-31B are block diagrams that illustrate an example of a distal attachment 2950" used as a beam 112*b* to couple the linear actuator 2216 to the foot in the system 3000 of FIG. 30A. The distal attachment 2950" is an adjustable saddle 3152 to secure around a length of the shoe 2202 that is configured to receive the foot. The saddle 3152 includes a first cup 3154 shaped to receive a heel portion of the shoe 2202 and a second cup 3156 shaped to receive a toe portion of the shoe 2202. A bar 3158 with a slot 3160 has a first end that is secured to the first cup 3154 and has a second end that is slidably received in a groove 3161 of the second cup 3156. However, the distal attachment 2950" is not limited to this structural arrangement and the first end of the bar 3158 can be secured to the second cup 3156 and the second end of the bar 3158 can be slidably received in a groove of the first cup 3154. In an example embodiment, the bar 3158 is slid into the groove 3161 by a selective amount, such that the spacing of the first and second cups 3154, 3156 corresponds to a size of the shoe 2202. Fasteners 3163 in the second cup 3156 are then fastened within the slot 3160, to secure the spacing of the first and second cups 3154, 3156.

In an example embodiment, the second cup 3156 includes side plates 3165*a*, 3165*b* with a junction 3173 (corresponding to pivot 114). In an example embodiment, a cylinder 3166 is connected at the junction 3173 between the side plates 3165*a*, 3165*b*. FIG. 31C is a block diagram that illustrates an example of a ball joint 3168 used to couple the linear actuator 2216 to the foot in the distal attachment 2250" of FIGS. 31A-31B. In an example embodiment, a second bar 3171 is initially positioned within a passage 3175 of the cylinder 3166 after which a first bar 3169 and ball joint 3168 are connected to the second bar 3171 within the passage 3175. The cylinder 3166 is subsequently connected at the junction 3173 between the side plates 3165a, 3165b. The ball joint 3168 is then connected to the linear actuator 2216. As the single motor 2214 moves the single linear actuator 2216 up or down, the ball joint 3168 and first bar 3169 simultaneously impart an upward or downward force at the junction 3173, which in-turn selectively imparts torque on the saddle 3152 (and shoe 2202) about the junction 3173 in only the PD plane 2220 and does not impart torque on the saddle 3152 (and shoe 2202) in the IE plane 2221 such that the foot is unconstrained in the IE plane 2221. In an example embodiment, dorsiflexion torque is imparted on the shoe 2202 in the PD plane 2220 based on upward movement of the linear actuator 2216 and plantarflexion torque is imparted on the shoe 2202 in the PD plane 2220 based on downward movement of the linear actuator 2216.

In an example embodiment, the systems 2200, 2300, 2600, 2900, 3000 need not include the sensors 120, 121, the linear actuators, the shoes, the proximal attachments and/or the distal attachments discussed above. In this example embodiment, the systems 2200, 2300, 2600, 2900, 3000 merely include the single motor 2214 and the controller 140 with the module 150 that is configured to at least perform steps 207, 209, 211, 213 of the method 200. In an example embodiment, the module 150 of the controller 140 obtains the plurality of movement phases based on the subject sensor states (step 201), the robot parameter trace of the normal subject (step 203) and/or the robot parameter trace of the impaired subject (step 205) from an external source. In another example embodiment, the controller 140 includes a sensor input to connect with the sensor communication channels 122 and receive input from the subject sensors 120 and/or the robot sensors 121.

In an example embodiment, during step 209, the controller 140 receives data along the sensor communication channels 122 from one or more subject sensors 120 to determine the current movement phase. In an example embodiment, the subject sensors 120 are the footswitches 425 (FIG. 4B) in the heel and toe region of the shoe to generate the controller input for PD plane 2220 actuation and thus need not include the footswitches 425 in the medial or lateral region of the shoe. In an example embodiment, the subject sensors 120 include the footswitches 425 in the heel region, the toe region, the medial region and the lateral region of the shoe.

In an example embodiment, during steps 203, 205, the controller 140 receives data along the sensor communication channels 122 from one or more robot sensors 121. In an example embodiment, the sensor 121 is only one sensor 313 that measures a linear movement of the linear actuator 2216. In an example embodiment, the sensor 313 is a linear incremental optical encoder. In an example embodiment, the sensor 121 need not include the sensor 312 that measures internal/external rotation outside of the PD plane 2220. In an example embodiment, the sensor 312 is a rotary encoder. In some embodiments, the system 2200, 2300, 2600, 2900, 3000 excludes any sensor 121, such as where steps 203, 205 are not performed by the system but instead are performed by an external system and the robot parameter traces of the normal and impaired subjects are uploaded to the module 150.

Figure 32:
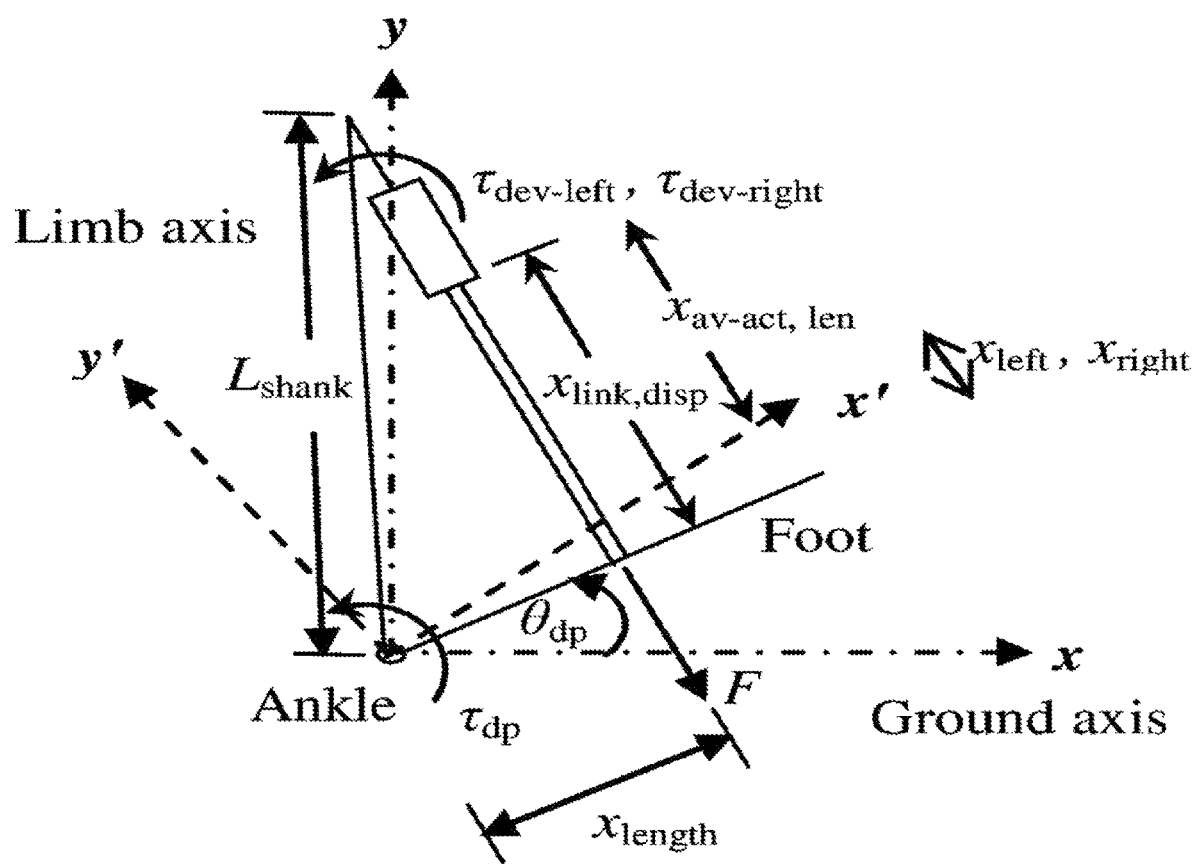
FIG. 32 is a diagram that illustrates example dimensions of a body and a foot wearing the anklebot, according to an embodiment.

In an example embodiment, during steps 203, 205, the sensor 121 is either sensor 312, 313. In another example embodiment, during steps 203, 205, the sensors 121 is both sensors 312, 313, where sensor 313 measures linear movement data of the linear actuator 2216 to estimate robot parameter data including ankle angle data in the PD plane 2220 and sensor 312 is used to commutate the motor 2214. In an example embodiment, the sensor 313 detects linear movement of the linear actuator 2216. In one example embodiment, the sensor 313 transmits linear movement data indicating the linear movement to the module 150 along the sensor communication channels 122 and the module 150 subsequently converts the linear movement data into robot state parameter data, such as position data of the shoe in the PD plane 2220. In another example embodiment, the sensor 313 converts the linear movement data to the robot state parameter data and subsequently transmits the robot state parameter data to the module 150 along the sensor communication channels 122. In an example embodiment, the position data of the shoe in the PD plane 2220 includes an angle of the shoe (relative to a fixed axis) or a speed of the shoe in the PD plane 2220. FIG. 32 is a diagram that illustrates example dimensions of a body and a foot wearing the anklebot, according to an embodiment. The angle $\theta_{dp}$ of the shoe in the PD plane 2220 is obtained by:

$$\theta_{dp} = \sin^{-1}(x) + \theta_{dpoffset} \quad (11)$$

where x is a dimension of the projection along the ground coordinate system (x-y) of the distance between the line of action of actuator force and the point of attachment between the ankle and the anklebot along a ground axis (e.g. x-axis, see FIG. 32); $\theta_{dpoffset}$ is an offset angle of the ankle characterized by the relative orientation of the rotated limb coordinate axis (x'-y') and the ground coordinate axis (x-y) in the PD plane 2220. The value of x is obtained by:

$$x = \frac{x_{tr,len}^2 + L_{shank}^2 - x_{link,disp}^2}{2 x_{length} L_{shank}} \quad (12)$$

where $x_{tr,len}$ is the transmission length defined as the length from the point of rotary encoder 312 mounted on top of the motor 314 to the point of attachment of the linear actuator 2216 on the foot; $L_{shank}$ is a length of the subjects leg (e.g. measured from the ankle to the knee); $x_{link,disp}$ is a displacement length of the linear actuator 2216; and $x_{length}$ is a distance between a line of action of the linear actuator 2216 force and a point of attachment between the ankle and the anklebot in the PD plane 2220. The displacement length $x_{link,disp}$ is obtained using a net linear displacement $x_{right}$ of the linear actuator 2216 that is measured by the sensor 313:

$$x_{link,disp} = \frac{x_{avact} - x}{2} \quad (13)$$

where $x_{avact}$ is the average actuator 2216 length defined as half of the difference between the maximum actuator extension and maximum actuator compression. In an example embodiment, the module 150 receives linear movement data from the sensor 313 including the net displacement x of the linear actuator 2216 and uses equation 13 to calculate the displacement length $x_{link,disp}$ of the linear actuator 2216. The module 150 then uses the calculated displacement length $x_{link,disp}$ along with known values for $L_{shank}$, $x_{tr,len}$ and $x_{length}$ to calculate x using equation 12. The parameter $x_{tr,len}$ is determined by the linear measurement from the top of the rotary encoder mounted on the motor to the current linear displacement of the actuator. The module 150 then uses the calculated x value along with a known value for $\theta_{dpoffset}$ to calculate the angle $\theta_{dp}$ using equation 11. In some embodiments, the offset angle $\theta_{dpoffset}$ value varies with foot mass, intrinsic foot mechanical impedance such as ankle stiffness, and any pathological factors such as ankle spasticity. In an example embodiment, a typical known value of the offset angle $\theta_{dpoffset}$ in the PD plane 2220 is of the order of a few degrees.

In an example embodiment, during step 211, the module 150 determines linear movement data of the linear actuator 2216 that corresponds to the adaptive magnitude of the robot applied torque for the current movement phase. During step 213, the module 150 transmits the linear movement data for the current movement phase to the motor 2214, based on the adaptive timing for the current movement phase from step 209. Upon receiving the linear movement data from the module 150, the motor 2214 imparts linear movement to the linear actuator 2216 in accordance with the linear movement data such that the applied torque with the adaptive magnitude determined in step 211 is imparted on the pivot 114 in only the PD plane 2220. In an example embodiment, during a stance movement phase 404, the module 150 transmits linear movement data to the motor 2214 such that the motor 2214 imparts downward motion on the linear actuator 2216 such that a plantarflexion torque is applied (e.g., to correct the "push off" deficit) with the adaptive magnitude on the pivot 114 in only the PD plane 2220. In an example embodiment, during a swing movement phase 406, the module 150 transmits linear movement data to the motor 2214 such that the motor 2214 imparts upward motion on the linear actuator 2216 such that a dorsiflexion torque is applied (e.g., to correct the "drop foot" deficit) with the adaptive magnitude on the pivot 114 in only the PD plane 2220. In these example embodiments, the pivot 114 is positioned between the ankle and the toe region of the foot.

In an example embodiment, for the systems 2300, 2600 that include two linear actuators 2216, 2318 with one linear actuator on each side of the leg, steps 213 includes moving both linear actuators 2216, 2318 in a same direction such that the robot applied torque at the pivot 114 is only in the PD plane 2220. In an example embodiment, steps 213 includes applying a force of a same magnitude in the same direction to both linear actuators 2216, 2318. In an example embodiment, the connector 2319 facilitates moving both linear actuators 2216, 2318 in the same direction such that the robot applied torque at the pivot 114 is only in the PD plane 2220.

In an example embodiment, the systems 2200, 2300, 2600, 2900, 3000 are portable and self-contained such that the systems can each be carried on the subject 2790. In an example embodiment, the systems are portable and self-contained such that no external control means outside of the system worn by the subject 2790 can be used to monitor or control the operation of the system. In an example embodiment, the controller 140 and module 150 are a microchip such as Arduino Yún® with microprocessor ATmega32U4 or AR9331 Linux, Arduino, Somerville, Mass.

In an example embodiment, during steps 201, 209, in the event that one or more of the footswitches 425 in the shoe fails, the controller 140 and module 150 may not receive sensor states from the footswitches 425 that indicate the current movement phase. In an example embodiment, the system advantageously includes other backup sensors that can be used to provide data to the module 150 that can be used to determine the current movement phase of the impaired foot. In one example embodiment, as previously discussed, footswitches 425 are positioned in a shoe or distal attachment 2950' of the non-impaired foot and these footswitches 425 transmit a collective output to the module 150 that can be used by the module 150 to determine a current movement phase of the impaired foot. In another example embodiment, one or more sensors are positioned on the foot and/or the knee to provide data to the module 150 that can be used to determine the current movement phase of the impaired foot. In an example embodiment, a knee sensor (e.g., 315) is provided that is a single-turn or multi-turn analog potentiometer that can be used to determine current movement phase data of the impaired knee. In this example embodiment, this data is used to map the angular position of the knee joint to that of the ankle joint to provide assistance to the impaired foot. In another example embodiment, as previously discussed, a voltage signal from the motor 2214, based on an imparted torque by the subject on the joint 114 is transmitted to the controller 140 and module 150 and the module 150 uses the voltage signal to determine the current movement phase.

In an example embodiment, before step 205, the method 200 includes a step to determine if the impaired subject has one or more health conditions. In an example embodiment, the deficit parameter in step 207, the adaptive timing in step 209 and/or the adaptive magnitude in step 211 are adjusted, based on the determined health condition(s). In another example embodiment, the number of movement cycles for a therapy session in step 217 and/or the number of physical therapy sessions for physical therapy in step 219 are adjusted, based on the one or more determined health conditions. In another example embodiment, the predicted adaptive magnitude in step 221 is adjusted, based on the one or more determined health conditions.

In an example embodiment, the health conditions include amputation prostheses to replace lost limbs in a patient, where the method 200 is used to help the patient recover mobility and sensory function. In another example embodiment, the health conditions include diabetic neuropathy where the method 200 is used to regulate foot pressure and ground reaction forces. In another example embodiment, the health conditions include health conditions of motor learning where the method 200 is employed to improve outcomes for podiatry, orthopedics, and prosthetics. In another example embodiment, the health conditions include stroke, where the method 200 is used to improve walking and balancing function, by means of increasing contribution of a paretic (e.g. affected) ankle. In another example embodiment, the health conditions include Multiple Sclerosis (MS), Parkinson's disease, or neuropathy or peripheral neuropathy. In an example embodiment, the method 200 is used as a disruptive technology to break gait freeze in subjects with Parkinson's disease. In an example embodiment, the method 200 is used to provide one or more torque bursts during episodes of freeze in subjects with Parkinson's disease during turning, changing directions or gait, to provide sensory cueing and assistive torque in order to break the freeze episode toward continuity of the mobility task and lower falls risk.

In another example embodiment, these health conditions include, but are not limited to, lower extremity orthopedic conditions and trauma, including damage to the peroneal nerve, sciatic nerve, or lumbar 4 and 5 disc compression or other nerve roots, spinal cord, cauda equine, or conus medullaris injuries that alter ankle function to compromise walking and balance. In another example embodiment, these health conditions include neuromuscular and orthopedic conditions including trauma to the tibia creating anterior compartment syndrome with muscle and/or nerve damage that compromises ankle sensorimotor control, and acetabular fracture that alters ankle innervation.

In an example embodiment, the single motor 2214 of the systems 2200, 2300, 2600, 2900, 3000 is selected based on parameters, including one or more of back-drivability, a minimum continuous stall torque in a range of 0.4-0.5 Newton meters (N*m), a minimum peak torque of 1.6 N*m, a minimum torque to mass ratio of 0.639 N*m per kilogram (kg), a maximum weight of 0.78 kg and a maximum cost of $6600. In an example embodiment, the single motor 2214 has all of the above listed parameters.

As previously discussed, the systems 2200, 2300, 2600, 2900, 3000 are similar to the system 300, with one distinction being that the pair of motors 314 is replaced by the single motor 2214. In an example embodiment, in order for the single motor 2214 to apply the same torque as the pair of motors 314, the single motor 2214 is selected, such that the parameters of the single motor 2214 are equivalent to the parameters for the pair of motors 314. In an example embodiment, Table 1 below shows parameters for a Kollmorgen RBE(H) series motor candidates: an RBE(H) 00714 motor (used in an example embodiment for the motor 314), and Kollmorgen RBE(H) 01213 and Kollmorgen RBE(H) 01214 motors (example candidates for the single motor 2214). The choice of Kollmorgen RBE(H) motors as candidates for the single motor 2214 for systems 2200, 2300, 2600, 2900, 3000 is in part, due to the high continuous stall and peak torques, low static friction torque, low mass, high torque-to-mass ratio, and low cost, all relative to other motors in the market.

TABLE 1

Replacing Two Motors with One Comparison

| Spec | Kollmorgen RBE(H) 00714 | Kollmorgen RBE(H) 01213 | Kollmorgen RBE(H) 01214 |
|---|---|---|---|
| Output power @ 25 C. (W) | 168 | 203 | 216 |
| Max Power Input (W) | 191.2 | 357.8 | 416.5 |
| Efficiency | 88% | 57% | 52% |
| Speed at rated power (RPM) | 9750 | 7152 | 6230 |
| Max Mechanical Speed (RPM) | 20000 | 18000 | 18000 |
| Cont. Stall Torque (N-m) | 0.25 | 0.387 | 0.467 |
| Peak Torque (N-m) | 0.802 | 1.57 | 1.99 |
| Static Friction (N-m) | 0.024 | 0.021 | 0.024 |
| Cogging Torque (N-m) | 0.023 | 0.0078 | 0.0097 |
| Inertia (kg-m^2) | $3.18 \times 10^{-6}$ | $1.55 \times 10^{-5}$ | $1.98 \times 10^{-5}$ |
| Weight (kg) | 0.391 | 0.552 | 0.641 |
| Torque-mass ratio | 0.639 | 0.701 | 0.729 |
| Cost | $ 3,300 | $ 3,135 | $ 3,200 |
| Backdriveablity | yes | yes | yes |

According to Table 1, the Kollmorgen 00714 motor has a continuous stall torque of 0.25 Nm, a peak torque of 0.802 Nm, a weight of 0.391 kg, a torque to mass ratio of 0.639 Nm/kg and a $3300 cost. Since the single motor 2214 is replacing a pair of Kollmorgen 00714 motors, the minimum parameters of the single motor 2214 include a continuous stall torque of 0.50 Nm, a peak torque of 1.60 Nm, a weight less than 0.780 kg (to reduce overall weight of the system), a torque to mass ratio greater than 0.639 Nm/kg and a cost of less than $6600 (to reduce the overall cost of the system). In this example embodiment, based on these criteria for the single motor 2214 and the Table 1 data, the Kollmorgen 01214 motor was selected for the single motor 2214 in some embodiments. However, the systems 2200, 2300, 2600 are not limited to any specific motor nor is the selection of the motor 2214 limited to the specific numerical parameter thresholds listed above and include numerical parameter thresholds equal or better to those listed in Table 1 that become available in an ever evolving market. The single motor 2214 of the systems 2200, 2300, 2600, 2900, 3000 can be selected, based on any parameters which ensure that the motor 2214, in step 213, applies the adaptive magnitude of the anklebot applied torque on the shoe 2202 in only the PD plane 2220, for the current movement phase, based on the adaptive timing for the current movement phase, and based on the applications E through F.

As previously discussed, the system 2200, 2900, 3000 is similar to the system 300, where another distinction is that the pair of linear actuators 316 are replaced by the single linear actuator 2216. Additionally, as discussed above, the pair of motors 314 is replaced by the single motor 2214. As a result, the system 2200, 2900, 3000 results in a reduction in weight of the system 300 by the difference between the pair of motors 314 and the single motor 2214, as well as the weight of one linear actuator 314 (and its casing). Additionally, the system 2200, 2900, 3000 results in a reduction in cost of the system 300 by the difference in cost between the pair of motors 314 and the single motor 2214, as well as the cost of one linear actuator 314 (and its casing). Additionally, in an example embodiment, the system 2200, 2900, 3000 need not include the medial and lateral footswitches 425, nor the sensors 312, 313 (correspond to robot sensors 121). In an example embodiment, Table 2 below shows the resulting savings in cost and reduction in weight of the system 2200, 2900, 3000, as compared to the system 300. The systems 2200, 2300, 2600, 2900, 3000 are not limited by the choice of actuator in the system 300. In an example embodiment, Roh'Lix actuators were selected for the linear actuator 314 of system 300 as they are threadless, linear screw actuators providing high back-drivability and in an example embodiment, back-drivability is a parameter of the linear actuators used in systems 300, 2200, 2300, 2600, 2900, 3000. However, the systems 300, 2200, 2300, 2600, 2900, 3000 are not limited to any specific linear actuator, and flexibility of choice of other actuators in the same class (threadless, liner screw) or another class is retained in case actuators with equal or better characteristics as Roh'Lix, become available in an ever-evolving market.

TABLE 2

| COMPONENT | Ind. Weight (kg) | QTY | TOTAL (kg) | COST ($) |
|---|---|---|---|---|
| ORIGINAL DESIGN | | | | |
| Roh'Lix Actuator | 0.226 | 2 | 0.452 | $ 150.00 |
| Casing | 1.6 | 2 | 3.2 | |
| Kollmorgen 00714 | 0.391 | 2 | 0.782 | $6,600.00 |
| TOTAL | | | 4.4340 | $6,750.00 |
| 1 DOF DESIGN | | | | |
| Roh'Lix Actuator | 0.226 | 1 | 0.226 | $ 75.00 |
| Casing | 1.6 | 1 | 1.6 | |
| Kollmorgen 01214 | 0.641 | 1 | 0.641 | $3,200.00 |
| TOTAL | | | 2.460 | $3,275.00 |
| POTENTIAL SAVINGS | | | 1.967 | $3,475.00 |

As depicted in Table 2, in an example embodiment, the system 2200, 2900, 3000 has a lightweight of approximately 2.47 kg and an affordable cost of $3275 for the actuator-casing-motor assembly. The resulting reduction in weight and savings in cost of the system will translate into a lightweight and affordable anklebot that the subject can take home. The subject can then engage the anklebot over many more gait cycles than would have been possible on an anklebot during scheduled training sessions at a medical facility. As a result, the subject can experience more rapid and continued improvements in the deficit parameters of each movement phase.

3. Computational Hardware Overview

Figure 19:
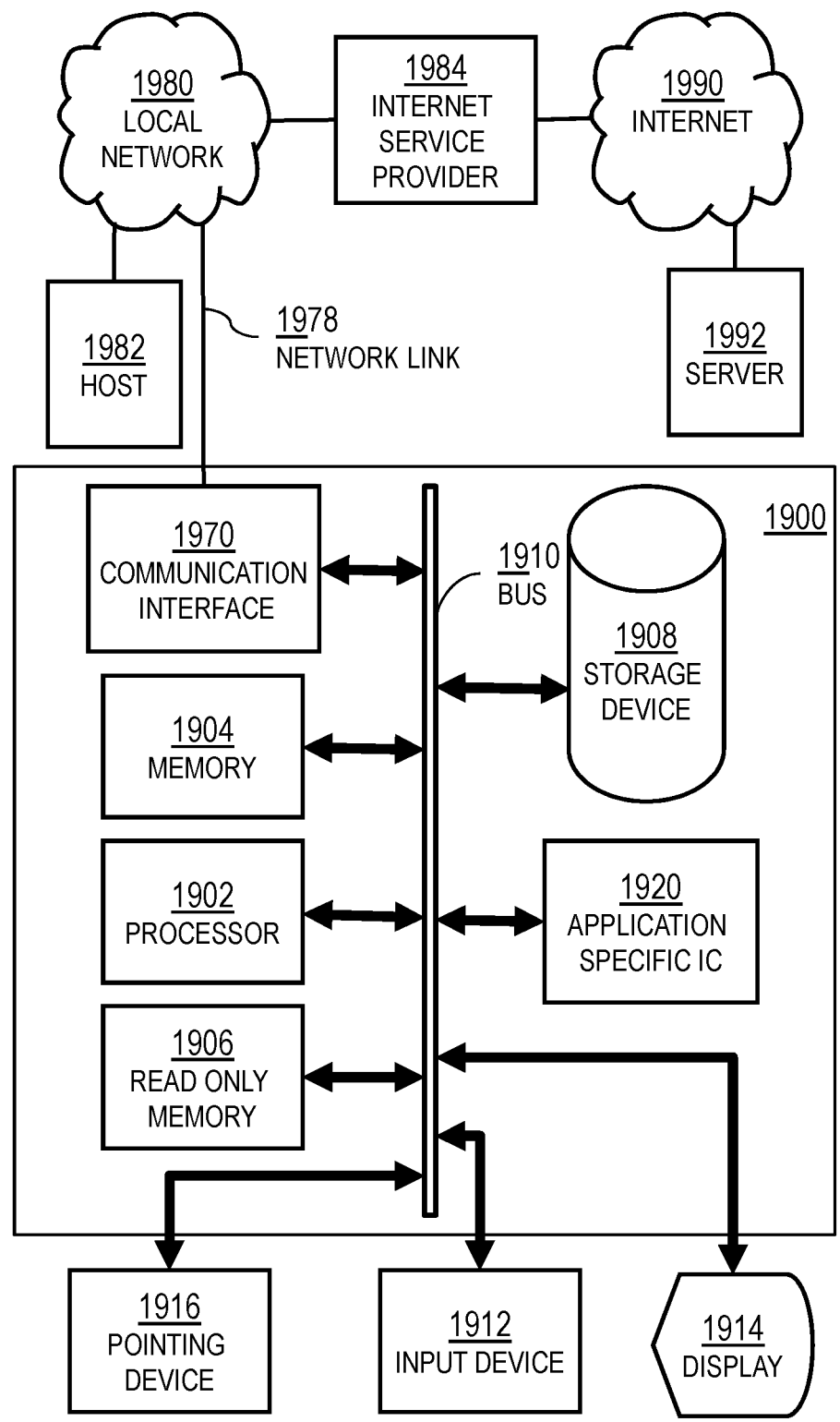
FIG. 19 is a block diagram that illustrates a computer system upon which an embodiment of the invention may be implemented.

FIG. 19 is a block diagram that illustrates a computer system 1900 upon which an embodiment of the invention may be implemented. Computer system 1900 includes a communication mechanism such as a bus 1910 for passing information between other internal and external components of the computer system 1900. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1900, or a portion thereof, constitutes a means for performing one or more steps of one or more methods described herein.

A sequence of binary digits constitutes digital data that is used to represent a number or code for a character. A bus 1910 includes many parallel conductors of information so that information is transferred quickly among devices coupled to the bus 1910. One or more processors 1902 for processing information are coupled with the bus 1910. A processor 1902 performs a set of operations on information. The set of operations include bringing information in from the bus 1910 and placing information on the bus 1910. The set of operations also typically include comparing two or more units of information, shifting positions of units of information, and combining two or more units of information, such as by addition or multiplication. A sequence of operations to be executed by the processor 1902 constitutes computer instructions.

Computer system 1900 also includes a memory 1904 coupled to bus 1910. The memory 1904, such as a random access memory (RAM) or other dynamic storage device, stores information including computer instructions. Dynamic memory allows information stored therein to be changed by the computer system 1900. RAM allows a unit of information stored at a location called a memory address to be stored and retrieved independently of information at neighboring addresses. The memory 1904 is also used by the processor 1902 to store temporary values during execution of computer instructions. The computer system 1900 also includes a read only memory (ROM) 1906 or other static storage device coupled to the bus 1910 for storing static information, including instructions, that is not changed by the computer system 1900. Also coupled to bus 1910 is a non-volatile (persistent) storage device 1908, such as a magnetic disk or optical disk, for storing information, including instructions, that persists even when the computer system 1900 is turned off or otherwise loses power.

Information, including instructions, is provided to the bus 1910 for use by the processor from an external input device 1912, such as a keyboard containing alphanumeric keys operated by a human user, or a sensor. A sensor detects conditions in its vicinity and transforms those detections into signals compatible with the signals used to represent information in computer system 1900. Other external devices coupled to bus 1910, used primarily for interacting with humans, include a display device 1914, such as a cathode ray tube (CRT) or a liquid crystal display (LCD), for presenting images, and a pointing device 1916, such as a mouse or a trackball or cursor direction keys, for controlling a position of a small cursor image presented on the display 1914 and issuing commands associated with graphical elements presented on the display 1914.

In the illustrated embodiment, special purpose hardware, such as an application specific integrated circuit (IC) 1920, is coupled to bus 1910. The special purpose hardware is configured to perform operations not performed by processor 1902 quickly enough for special purposes. Examples of application specific ICs include graphics accelerator cards for generating images for display 1914, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1900 also includes one or more instances of a communications interface 1970 coupled to bus 1910. Communication interface 1970 provides a two-way communication coupling to a variety of external devices that operate with their own processors, such as printers, scanners and external disks. In general the coupling is with a network link 1978 that is connected to a local network 1980 to which a variety of external devices with their own processors are connected. For example, communication interface 1970 may be a parallel port or a serial port or a universal serial bus (USB) port on a personal computer. In some embodiments, communications interface 1970 is an integrated services digital network (ISDN) card or a digital subscriber line (DSL) card or a telephone modem that provides an information communication connection to a corresponding type of telephone line. In some embodiments, a communication interface 1970 is a cable modem that converts signals on bus 1910 into signals for a communication connection over a coaxial cable or into optical signals for a communication connection over a fiber optic cable. As another example, communications interface 1970 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1970 sends and receives electrical, acoustic or electromagnetic signals, including infrared and optical signals that carry information streams, such as digital data.

The term computer-readable medium is used herein to refer to any medium that participates in providing information to processor 1902, including instructions for execution. Such a medium may take many forms, including, but not limited to, non-volatile media, volatile media and transmission media. Non-volatile media include, for example, optical or magnetic disks, such as storage device 1908. Volatile media include, for example, dynamic memory 1904. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1902, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1902, except for carrier waves and other signals.

Logic encoded in one or more tangible media includes one or both of processor instructions on a computer-readable storage media and special purpose hardware, such as ASIC *1920.

Network link 1978 typically provides information communication through one or more networks to other devices that use or process the information. For example, network link 1978 may provide a connection through local network 1980 to a host computer 1982 or to equipment 1984 operated by an Internet Service Provider (ISP). ISP equipment 1984 in turn provides data communication services through the public, worldwide packet-switching communication network of networks now commonly referred to as the Internet 1990. A computer called a server 1992 connected to the Internet provides a service in response to information received over the Internet. For example, server 1992 provides information representing video data for presentation at display 1914.

The invention is related to the use of computer system 1900 for implementing the techniques described herein. According to one embodiment of the invention, those techniques are performed by computer system 1900 in response to processor 1902 executing one or more sequences of one or more instructions contained in memory 1904. Such instructions, also called software and program code, may be read into memory 1904 from another computer-readable medium such as storage device 1908. Execution of the sequences of instructions contained in memory 1904 causes processor 1902 to perform the method steps described herein. In alternative embodiments, hardware, such as application specific integrated circuit 1920, may be used in place of or in combination with software to implement the invention. Thus, embodiments of the invention are not limited to any specific combination of hardware and software.

The signals transmitted over network link 1978 and other networks through communications interface 1970, carry information to and from computer system 1900. Computer system 1900 can send and receive information, including program code, through the networks 1980, 1990 among others, through network link 1978 and communications interface 1970. In an example using the Internet 1990, a server 1992 transmits program code for a particular application, requested by a message sent from computer 1900, through Internet 1990, ISP equipment 1984, local network 1980 and communications interface 1970. The received code may be executed by processor 1902 as it is received, or may be stored in storage device 1908 or other non-volatile storage for later execution, or both. In this manner, computer system 1900 may obtain application program code in the form of a signal on a carrier wave.

Various forms of computer readable media may be involved in carrying one or more sequence of instructions or data or both to processor 1902 for execution. For example, instructions and data may initially be carried on a magnetic disk of a remote computer such as host 1982. The remote computer loads the instructions and data into its dynamic memory and sends the instructions and data over a telephone line using a modem. A modem local to the computer system 1900 receives the instructions and data on a telephone line and uses an infrared transmitter to convert the instructions and data to a signal on an infrared a carrier wave serving as the network link 1978. An infrared detector serving as communications interface 1970 receives the instructions and data carried in the infrared signal and places information representing the instructions and data onto bus 1910. Bus 1910 carries the information to memory 1904 from which processor 1902 retrieves and executes the instructions using some of the data sent with the instructions. The instructions and data received in memory 1904 may optionally be stored on storage device 1908, either before or after execution by the processor 1902.

Figure 20:
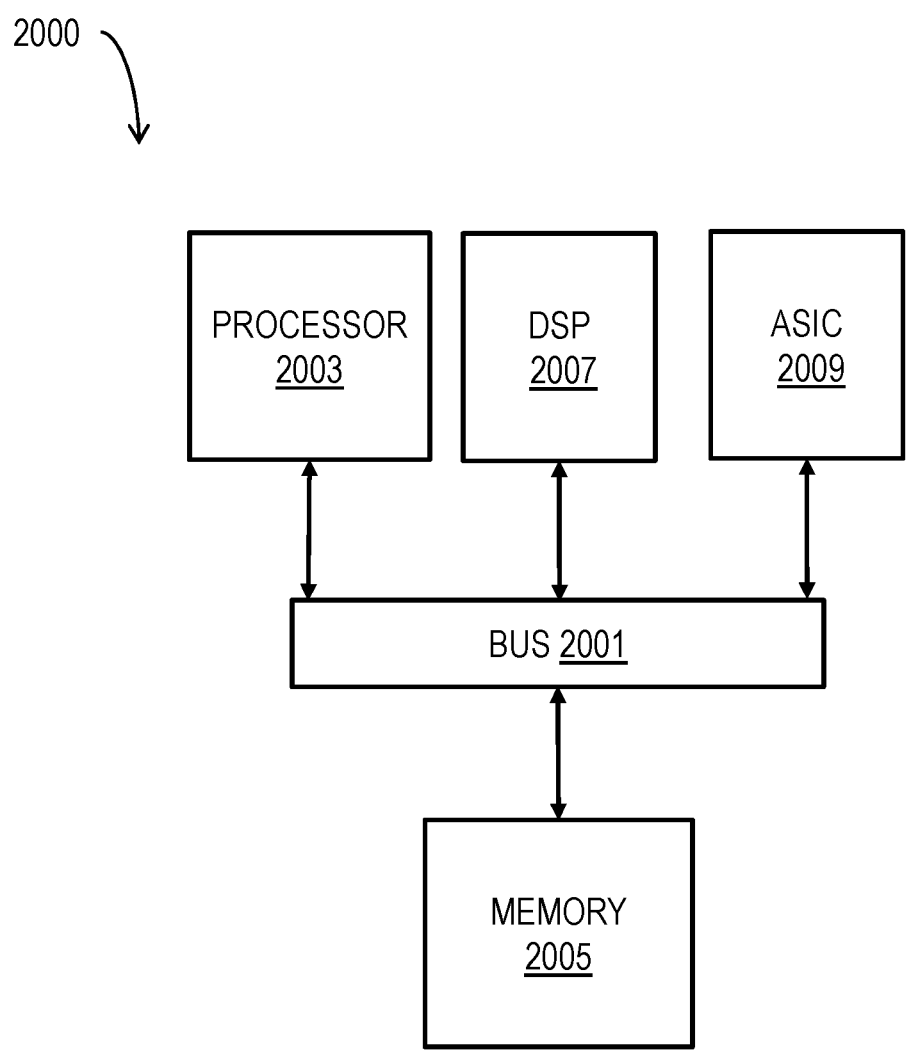
FIG. 20 is a block diagram that illustrates a chip set upon which an embodiment of the invention may be implemented.

FIG. 20 illustrates a chip set 2000 upon which an embodiment of the invention may be implemented. Chip set 2000 is programmed to perform one or more steps of a method described herein and includes, for instance, the processor and memory components described with respect to FIG. 20 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 2000, or a portion thereof, constitutes a means for performing one or more steps of a method described herein.

In one embodiment, the chip set 2000 includes a communication mechanism such as a bus 2001 for passing information among the components of the chip set 2000. A processor 2003 has connectivity to the bus 2001 to execute instructions and process information stored in, for example, a memory 2005. The processor 2003 may include one or more processing cores with each core configured to perform independently. A multi-core processor enables multiprocessing within a single physical package. Examples of a multi-core processor include two, four, eight, or greater numbers of processing cores. Alternatively or in addition, the processor 2003 may include one or more microprocessors configured in tandem via the bus 2001 to enable independent execution of instructions, pipelining, and multithreading. The processor 2003 may also be accompanied with one or more specialized components to perform certain processing functions and tasks such as one or more digital signal processors (DSP) 2007, or one or more application-specific integrated circuits (ASIC) 2009. A DSP 2007 typically is configured to process real-world signals (e.g., sound) in real time independently of the processor 2003. Similarly, an ASIC 2009 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 2003 and accompanying components have connectivity to the memory 2005 via the bus 2001. The memory 2005 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 2005 also stores the data associated with or generated by the execution of one or more steps of the methods described herein.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

What is claimed is:

1. An apparatus comprising:
   a variable torque motor configured to be connected to an exo-skeletal ankle robot comprising a pair of beams connected to a pivot, the pair of beams configured to be coupled to, respectively, a first limb and a second limb of a subject separated by an ankle of the subject and wherein the variable torque motor is configured to impart a robot applied torque about the pivot in only a first plane;
   at least one processor with a sensor input configured to receive first data from at least one first sensor during a plurality of movement phases of a gait cycle;
   at least one memory including one or more sequence of instructions;
   the at least one memory and the one or more sequence of instructions configured to, with the at least one processor, cause the apparatus to perform at least the following;
      determine a deficit parameter for each movement phase based on a respective robot state parameter of the exo-skeletal ankle robot of a normal subject and of an impaired subject;
      determine an adaptive timing for the robot applied torque based on a current movement phase based on current first data of the at least one first sensor; and
      determine an adaptive magnitude for the robot-applied torque based on the deficit parameter for the current movement phase;
   wherein
      the variable torque motor is in communication with the at least one memory to receive the adaptive magnitude and the adaptive timing and is configured to impart the robot applied torque at the adaptive magnitude in only the first plane to the pivot during the current movement phase based on the adaptive timing, wherein the variable torque motor is configured to impart the robot applied torque over the plurality of movement phases, wherein the torque is imparted in the same, first plane over the plurality of movement phases of the gait cycle; and
   the apparatus is portable such that the apparatus is configured to be carried by the subject.

2. The apparatus of claim 1, further comprising:
   the at least one first sensor;
   at least one second sensor wherein the sensor input is further configured to receive second data from the at least one second sensor of the respective robot state parameter of the exo-skeletal robot ankle during each movement phase; and
   the exo-skeletal ankle robot comprising a proximal attachment configured to attach to the first limb of the subject above the ankle of the subject and a distal attachment configured to attach to the second limb of the subject below the ankle;
   wherein the first plane is a plantar-dorsiflexion (PD) plane.

3. The apparatus of claim 2, wherein one of the beams is a linear actuator, wherein the first limb is a leg and wherein the proximal attachment is configured to attach the linear actuator to the leg above a knee.

4. The apparatus of claim 3, wherein the proximal attachment comprises a knee brace and a mounting block secured to the knee brace, wherein the mounting block includes at least one opening to mount the linear actuator to the knee brace and a milled out section other than the opening to reduce a weight of the mounting block.

5. The apparatus of claim 2, wherein one of the beams is a linear actuator, wherein the first limb is a leg and wherein the proximal attachment is configured to attach the linear actuator to the leg below a knee.

6. The apparatus of claim 5, wherein the proximal attachment comprises a strap secured around the leg below the knee and a block on the strap that is configured to removably attach the linear actuator to the strap.

7. The apparatus of claim 2, wherein one of the beams is a linear actuator, wherein the second limb is a foot and the distal attachment comprises a stirrup configured to be secured around the foot, said stirrup including side plates rotatably coupled at the pivot to the linear actuator.

8. The apparatus of claim 7, wherein the distal attachment further comprises a shoe configured to receive the foot and wherein the stirrup is integral with a sole of the shoe.

9. The apparatus of claim 7, wherein the distal attachment further comprises a strap to secure the stirrup around a shoe configured to receive the foot.

10. The apparatus of claim 7, wherein the beam comprises only one linear actuator and wherein the distal attachment further comprises at least one first bar secured to the side plates at the pivot and a second bar connecting the at least one first bar, wherein the linear actuator is connected to the second bar such that the at least one first bar and second bar are configured to impart the robot applied torque about the pivot in only the PD plane based on linear movement of the linear actuator.

11. The apparatus of claim 7, wherein the beam comprises only one linear actuator and wherein the distal attachment further comprises a block secured to the side plates at the pivot and a link to connect the block to the linear actuator, wherein the linear actuator is connected to the link such that the block and the link are configured to impart the robot applied torque about t the pivot in only the PD plane based on linear movement of the linear actuator.

12. The apparatus of claim 2, wherein one of the beams is a linear actuator, wherein the second limb is a foot and the distal attachment comprises an adjustable saddle configured to secure around a length of a shoe configured to receive the foot and wherein the pivot is a ball joint connector that connects the saddle to the linear actuator.

13. The apparatus of claim 2, wherein the second limb is a foot and wherein the at least one first sensor comprises a pressure sensor positioned in a heel region and a toe region of a shoe configured to receive the foot, and wherein the current first data is a collective output from the pressure sensors.

14. The apparatus of claim 2, wherein one of the beams is only one linear actuator, wherein the at least one second sensor comprises only one sensor configured to measure linear movement of the linear actuator during each movement phase and wherein the second data is linear movement data of the linear actuator or robot state parameter data based on the linear movement data.

15. The apparatus of claim 1, wherein the first limb is a leg and the second limb is a foot, wherein the beam coupled to the foot is a shoe to receive the foot, wherein the beam coupled to the leg is a linear actuator, and wherein the variable torque motor and linear actuator are configured to be mounted to a front side of the leg.

16. The apparatus of claim 1, further comprising a toggle switch to select a desired movement phase among the plurality of movement phases such that the adaptive timing is determined based on whether the current movement phase is the desired movement phase.

17. A method comprising:
(a) determining, on a processor, a value for a deficit parameter for each movement phase of a gait cycle based on a difference between a parameter trace for an exo-skeletal ankle robot for a normal subject and a parameter trace for an impaired subject at each movement phase;
(b) determining, on the processor, an adaptive timing for a robot applied torque based on a current movement phase based on a current sensor state from sensor data;
(c) determining, on the processor, an adaptive magnitude for the robot applied torque based on the value of the deficit parameter of the current movement phase; and
(d) applying, to the exo-skeletal ankle robot, the adaptive magnitude for the robot applied torque in only a first plane for the current movement phase, based on the adaptive timing, wherein a variable torque motor is configured to impart the robot applied torque over a plurality of movement phases, wherein the torque is imparted in the same, first plane over the plurality of movement phases of the gait cycle.

18. The method of claim 17, further comprising:
receiving, on the processor, robot state parameter data that indicates a robot state parameter of the exo-skeletal ankle robot as a function of time for each movement phase of a plurality of movement phases for the compound ankle function for an ankle based on the sensor data;
and wherein the first plane is a plantar-dorsiflexion (PD) plane.

19. The method of claim 18 further comprising:
determining, on the processor, a robot state parameter trace for each movement phase in the normal subject based on the robot state parameter data and the sensor data from the normal subject.

20. The method of claim 18 further comprising:
determining, on the processor, a robot state parameter trace for each movement phase in the impaired subject based on the robot state parameter data and the sensor data from the impaired subject.

21. The method of claim 18 wherein the receiving, on the processor, comprises receiving sensor data indicating variation of the robot state parameter in only the PD plane.

22. The method of claim 18, wherein the robot state parameter data comprises position data that indicates a position of the exo-skeletal ankle robot as a function of time in only the PD plane.

23. The method of claim 22, wherein the position data comprises at least one of angle data that indicates an angle of the exo-skeletal ankle robot relative to a fixed axis in the PD plane and speed data that indicates a speed of the exo-skeletal ankle robot in the PD plane.

24. The method of claim 22, wherein the receiving, on the processor, position data comprises receiving, on the processor, linear movement data that indicates linear movement of an actuator of the exo-skeletal ankle robot or the position data based on the linear movement data.

25. The method of claim 17, wherein step (d) comprises moving at least two linear actuators positioned on opposite sides of the exo-skeletal ankle robot in a same direction such that the robot applied torque is applied to the exo-skeletal ankle robot in only the PD plane.

26. The method of claim 17, wherein the determining of the adaptive timing comprises:
determining, on the processor, the current movement phase based on the current sensor state;
comparing the value for the deficit parameter for the current movement phase with a robot state parameter threshold;
comparing the current movement phase with a desired movement phase as determined by a toggle switch; and
transmitting an applied torque signal to a variable torque motor to apply the robot applied torque during the current movement phase if the value of the deficit parameter is greater than the robot state parameter threshold and if the current movement phase is the desired movement phase.

27. The method of claim 17, further comprising:
determining if the impaired subject has one or more health conditions prior to step (a); and
adjusting at least one of the adaptive timing or the adaptive magnitude based on the determined health condition of the impaired subject.

* * * * *